United States Patent
Perni et al.

(10) Patent No.: US 11,939,300 B2
(45) Date of Patent: Mar. 26, 2024

(54) COMPOUNDS AND METHODS FOR TREATING AUTOIMMUNE DISORDERS BY TARGETING HLA-DQ2

(71) Applicant: ImmunoMolecular Therapeutics, Inc., Woburn, MA (US)

(72) Inventors: Robert B. Perni, Marlborough, MA (US); Ryan Schutte, Gainesville, FL (US); James M. Siedlecki, Burlington, MA (US); Asha Ghevde, Andover, MA (US)

(73) Assignee: ImmunoMolecular Therapeutics, Inc., Woburn, MA (US)

( * ) Notice: Subject to any disclaimer, the term of this patent is extended or adjusted under 35 U.S.C. 154(b) by 54 days.

(21) Appl. No.: 17/407,565

(22) Filed: Aug. 20, 2021

(65) Prior Publication Data
US 2022/0055994 A1     Feb. 24, 2022

Related U.S. Application Data

(60) Provisional application No. 63/068,631, filed on Aug. 21, 2020.

(51) Int. Cl.
| | | |
|---|---|---|
| *C07D 307/33* | (2006.01) | |
| *A61F 9/00* | (2006.01) | |
| *A61K 31/502* | (2006.01) | |
| *A61P 3/00* | (2006.01) | |
| *A61P 25/00* | (2006.01) | |
| *C07D 237/08* | (2006.01) | |
| *C07D 237/28* | (2006.01) | |
| *C07D 307/94* | (2006.01) | |
| *C07D 403/08* | (2006.01) | |
| *C07D 405/04* | (2006.01) | |
| *C07D 405/06* | (2006.01) | |

(52) U.S. Cl.
CPC ......... *C07D 237/28* (2013.01); *C07D 403/08* (2013.01); *C07D 405/04* (2013.01)

(58) Field of Classification Search
CPC .. C07D 307/33; C07D 307/94; C07D 405/06; C07D 237/38; C07D 403/08; C07D 405/04; C07D 237/08; A61K 31/502; A61P 25/00; A61P 31/00; A61P 9/00
See application file for complete search history.

(56) References Cited

PUBLICATIONS

PubChem SID 255340075, https://pubchem.ncbi.nlm.nih.gov/substance/255340075, Nov. 28, 2015.
PubChem SID 310905153, https://pubchem.ncbi.nlm.nih.gov/substance/310905153, Feb. 18, 2016.
PubChem SID 310905170, https://pubchem.ncbi.nlm.nih.gov/substance/310905170, Feb. 18, 2016.
SciFinder Search Results (pp. 1-8), Dec. 27, 2019.
SciFinder Search Results (pp. 1-50), Dec. 27, 2019.

*Primary Examiner* — Bruck Kifle
(74) *Attorney, Agent, or Firm* — Elmore Patent Law Group, P.C.; Edgar W. Harlan; Carolyn S. Elmore

(57) ABSTRACT

Compounds and compositions useful in methods of treating, ameliorating, or inhibiting the development of an autoimmune disease by modulating the T cell response to antigenic peptide or fragments of antigenic peptides presented by the major histocompatibility (MHC) class II molecule, DQ2.

17 Claims, No Drawings

COMPOUNDS AND METHODS FOR TREATING AUTOIMMUNE DISORDERS BY TARGETING HLA-DQ2

RELATED APPLICATION

This application claims the benefit of U.S. Provisional Application No. 63/068,631, filed on Aug. 21, 2020. The entire teachings of the above application are incorporated herein by reference.

TECHNICAL FIELD

The invention relates to the use of small organic molecules in the prevention or treatment of autoimmune diseases, such as Celiac disease and Type 1 Diabetes.

BACKGROUND

Autoimmune disorders are diseases caused by the body producing an inappropriate immune response against its' own tissues, in which the immune system, T lymphocytes and autoantibodies, attack one's own cells, tissues, and/or organs. The major genetic risk factor for developing an autoimmune disease resides within human leukocyte antigen (HLA) gene complex located on chromosome 6. The HLA complex is divided into three regions: class I, II, and III. Alleles of the class II genes, DQ and DR (and to a lesser extent DP), are the most important determinants for developing an autoimmune disease. The HLA class II genes are polymorphic and encode major histocompatibility complex (MEW) II proteins. These MHC class II molecules are expressed on antigen presenting cells (e.g., B cells, dendritic cells, and macrophages) and function to present antigens to CD4 T-cells. In the case of autoimmunity, self-peptides presented by MHC class II molecules activate T cells to target one's own cells or tissues. Researchers have identified 80-100 different autoimmune diseases and suspect at least 40 additional diseases have an autoimmune basis.

Celiac disease is one of the most common autoimmune disorders, with a reported prevalence of 0.5-1% of the general population, with the exception of areas showing low frequency of celiac disease-predisposing genes and low gluten consumption (e.g., sub-Saharan Africa and Japan). Studies have shown that most celiac disease cases remain undetected in the absence of serological screening due to heterogeneous symptoms and/or poor disease awareness. Celiac disease prevalence is increasing in Western countries. Between the years 1975 and 2000, celiac disease prevalence increased 5-fold in the US, for reasons that are currently unknown. The prevalence of celiac disease is higher in first-degree celiac disease relatives (10-15%) and in other at-risk groups, particularly patients with Down syndrome, type 1 diabetes, or IgA deficiency. Celiac disease is diagnosed more frequently in women with a female-to-male ratio ranging from 2:1 to 3:1. The disease can occur at any age from early childhood to the elderly, with two peaks of onset—one shortly after weaning with gluten in the first 2 years of life, and the other in the second or third decades of life. The diagnosis of celiac disease can be challenging because symptoms can vary significantly from patient to patient.

Celiac disease is a unique autoimmune disease in that its key genetic elements (human leukocyte antigen (HLA)-DQ2 and HLA-DQ8), the auto-antigen involved (tissue transglutaminase (tTG)), and the environmental trigger (gluten) are all well-defined. DQ2 and DQ8 alleles are the predominant HLA alleles in Celiac disease, being present in about 99% of patients with DQ2 being predominant at about 90%. The majority of individuals with Celiac disease carry one of the DQ2 subtypes defined as: DQ2.5cis (DQA1*05:01-DQB1*02:01), DQ2.5trans (present with the genotype of DQA1*02:01-DQB1*02:02+DQA1*05:05-DQB1*03:01), DQ2.2 (DQA1*02:01-DQB1*02:02), and DQ2.3 (DQA1*03:01-DQB1*02:01). DQ8 (DQA1*03:01-DQB1*03:02) is the other risk allele for celiac disease. Gliadin, one of the two principle protein components of gluten, contains a number of well-studied T cell epitopes. Deamidation of gliadin peptides by tissue transglutaminase (TTG) type 2 converts glutamine into glutamic acid, resulting in immunogenic T cell epitopes. A major drawback in celiac disease research has been the lack of a reliable and reproducible animal model, with the possible exception of the Irish setter dog, which may develop a gluten-related disease. Nevertheless, new technologies pertinent to human gut biology and immunology are opening unprecedented opportunities for major research breakthroughs.

As with any other autoimmune disease, celiac disease has a strong hereditary component as evidenced by its high familial recurrence (10-15%) and the high concordance of the disease among monozygotic twins (75-80%). Also common to other autoimmune diseases is the relevant role of HLA class II heterodimers, specifically DQ2 and DQ8, in the heritability of celiac disease. HLA-DQ2 homozygosis confers a much higher risk (25-30%) of developing early-onset celiac disease in infants with a first-degree family member affected by the disease. Currently, the only effective treatment available for celiac disease is a strict gluten free diet for life because it leads to the resolution of intestinal and extraintestinal symptoms, negativity of autoantibodies, and the regrowth of the intestinal villi. In addition, the diet offers a partial protective effect towards several complications. However, these crucial advantages are accompanied by disadvantages, including a negative impact on quality of life, psychological problems, fear of involuntary/inadvertent contamination with gluten (as demonstrated in multicenter GIP studies), possible vitamin and mineral deficiencies, metabolic syndrome, an increased cardiovascular risk, and often severe constipation. Due to the relevant burden induced by gluten withdrawal with consequent worsening of quality of life, about 40% of celiac disease patients are unsatisfied with their alimentary regimen and they would be keen to explore alternative treatments.

Type 1 diabetes (T1D), the immune mediated form of diabetes, is a chronic autoimmune disorder resulting in the destruction of insulin-producing beta cells within the pancreatic islets requiring lifelong daily insulin treatment. Autoantibodies directed toward insulin (IAA) and beta cell-specific antigens, glutamic acid decarboxylase 65 (GAD65), insulinoma-associated antigen 2 (IA-2) and zinc transporter 8 (ZnT8) are considered diagnostic and predictive of T1D. An association between T1D and CD has been recognized and intensely studied. The prevalence of CD ranges from 1% to 10% in patients with T1D, compared with 1% in the general population. In most subjects, the onset of T1D precedes the diagnosis of CD or the two diseases are diagnosed simultaneously. Shared susceptibility genes in the HLA region contribute to the coexistence of T1D and CD with HLA-DR3-DQ2 and HLA-DR4-DQ8 haplotypes being the strongest genetic risk factors for T1D and CD. For example, the DR3-DQ2 haplotype is found in about 90% of CD and 55% of T1D patients. The co-occurrence of T1D and CD is highly associated with the high-risk genotypes DR3-DQ2/DR3-DQ2 and DR3-DQ2/DR4-DQ8. Independent of the co-occurrence of celiac disease and type 1 diabetes, the DR3-DQ2 haplotype confers significant disease risk for the development of type 1 diabetes.

Stiff-person syndrome (SPS) is a rare neurological disorder characterized by fluctuating muscle rigidity in the trunk and limbs and a heightened sensitivity to stimuli such as noise, touch, and emotional distress, which can set off muscle spasms. Abnormal postures, often hunched over and stiffened, are characteristic of the disorder, and people with SPS can be too disabled to walk or move. SPS affects twice as many women as men and is frequently associated with other autoimmune diseases such as diabetes, thyroiditis, vitiligo, and pernicious anemia. The cause of SPS is not fully understood, but research indicates that it is the result of an autoimmune response in the brain and spinal cord. The disorder is often misdiagnosed as Parkinson's disease, multiple sclerosis, fibromyalgia, psychosomatic illness, or anxiety and phobia. A definitive diagnosis can be made with a blood test that measures the level of glutamic acid decarboxylase (GAD) antibodies in the patient's blood. SPS patients respond to high doses of diazepam and anti-convulsants, gabapentin, tiagabine, and intravenous immunoglobulin (IVIg) treatment has been shown to reduce stiffness and lower sensitivity to noise, touch, and stress. Although these treatments will improve the symptoms of SPS, there is currently no cure for the disorder, and most SPS patients have frequent falls which can result in severe injuries because they lack the normal defensive reflexes. SPS is correlated with the HLA DQ2 DQB1*02:01 allele (present in approximately 70% of patients with SPS).

Addison's disease (AD) is a disorder that occurs when the adrenal glands don't make enough cortisol and aldosterone, resulting in fatigue, muscle weakness, loss of appetite, weight loss, dehydration, hypotension, and abdominal pain. The primary cause of Addison's disease is an autoimmune disorder this is treated by replacing these hormones as well as high-sodium diets, and calcium and vitamin D supplementation. Addison's disease is highly correlated with the DR3-DQ2/DR4-DQ8 genotype.

Schmidt syndrome (SS) refers to the combination of autoimmune adrenal insufficiency (Addison's disease) with autoimmune hypothyroidism and/or type 1 diabetes mellitus (T1DM) and is part of a larger syndrome known as autoimmune polyendocrine syndrome type II or polyglandular autoimmune syndrome type II (PAS II; the term Schmidt syndrome is used interchangeably with PAS II). Schmidt Syndrome is a rare disorder with a prevalence of 1:20,000 in the general population, with 3:1 ratio of females to males affected, with peak incidence in the 3rd-4th decade of life. Diagnosis and treatment of Schmidt syndrome is the same as the underlying disorders (i.e., diagnosis and treatment of Addison's disease, autoimmune hypothyroidism, and/or T1DM). Among patients with T1DM, <1% of patients have Addison's disease, whereas 2-5% have autoimmune thyroid disease (mainly hypothyroidism) and up to 5% have celiac disease. Up to 33% may have thyroid autoantibodies and 12% have transglutaminase autoantibodies. In addition to the DR3-DQ2/DR4DQ8 genotype associated with Addison's disease, the DR3-DQ2/DR4-DQ8 is recognized as a susceptibility genotype in Schmidt syndrome patients that have type 1 diabetes and autoimmune thyroid disease but without Addison's disease.

Myasthenia gravis (MG) is an autoimmune disorder of the nervous system that affects the neuromuscular junctions, leading to muscle weakness and fatigue that worsens after periods of activity and improves after periods of rest. Antibodies against the acetylcholine receptor are detected in the majority (85-90%) of MG patients and are highly specific and pathogenic. MG affects both men and women and occurs across all racial and ethnic groups. It most commonly impacts young adult women (under 40) and older men (over 60), but it can occur at any age, including childhood. Treatments for MG include thymectomy, eculizumab, anticholinesterase and immunosuppressive medications. MHC Allele associations with MG seem to differ from population to population, and their contribution to the pathogenesis remains unclear, but human genotyping studies of MG patients has associated MG with HLA-DRB1*09, HLA-DRB1*14, DRB1*15, and HLA-DQB1*02 (DQ2) alleles.

Thus, there exists a need in the art for safer and more effective methods for treating or slowing the progression or development of autoimmune disorders, such as those associated with MHC class II, DQ2 alleles. The invention addresses these needs by providing molecules and formulations useful in the treatment and prevention of autoimmune diseases while achieving other advantages discussed more fully below.

SUMMARY OF THE INVENTION

The present invention provides compounds that can be used to prevent or reduce T cell activation through the presentation of antigens that bind MHC class II molecules on the surface of antigen presenting cells, as well as therapeutic uses of a compound of the invention and pharmaceutical compositions comprising a compound of the invention to prevent or slow the formation of autoimmune diseases in an individual.

Blocking allele-specific MHC class II antigen presentation by inhibiting DQ2-mediated T cell responses has been identified as a target for treating celiac disease (ref). DQ2 confers significant disease risk by presenting epitopes of antigens (for example, gluten and/or insulin antigens, or fragments or antigenic components thereof) to effector CD4+ T cells. Gliadins, key components of gluten, are complex proteins unusually rich in prolines and glutamines and are not completely digestible by intestinal enzymes. Partial digestion of gliadins results in a mix of peptides that can trigger host responses (increased gut permeability and innate and adaptive immune response). The present inventors have surprisingly found that the compounds of the invention block or reduce gliadin peptide presentation to T cells. Without intending to be bound by theory, it is believed that the compounds disclosed herein occupy a pocket along the DQ2 peptide binding groove, thereby blocking major histocompatibility complex class II HLA-DQ2/8-antigen restricted T cells responses in vitro, and inhibiting DQ2/8-antigen presentation in vivo. Blocking HLA-DQ2 antigen presentation in this way may decrease autoimmune T cell activation thereby preventing and/or treating and/or slowing the development of autoimmune disorders. For example, blocking HLA-DQ2 gliadin presentation to CD4+ T cells may help preserve intestinal mucosal and epithelial barrier in new onset celiac disease and may also prevent or delay celiac disease onset.

In one embodiment, the present invention provides compounds of Formula (I),

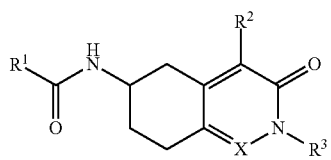

and pharmaceutically acceptable salts thereof, wherein
$R^1$ is H, optionally substituted $C_1$-$C_6$-alkyl; optionally substituted aryl; optionally substituted $C_3$-$C_7$-cycloalkyl; optionally substituted heterocyclyl, or optionally substituted heteroaryl; preferably $R^1$ is optionally substituted $C_1$-$C_4$-alkyl; optionally substituted phenyl, optionally substituted naphthyl, or optionally substituted quinolyl;

$R^2$ is H, optionally substituted $C_{1-6}$ alkyl, or $OR^4$ wherein $R^4$ is H or optionally substituted $C_{1-6}$ alkyl;

$R^3$ is H or optionally substituted $C_1$-$C_6$-alkyl; or $R^3$ is H; optionally substituted $C_1$-$C_6$-alkyl; optionally substituted $C_3$-$C_8$-cycloalkyl; optionally substituted aryl; optionally substituted heteroaryl; optionally substituted 3 to 8 membered heterocyclyl; or —(CH$_2$)$_n$—Y, where n is 1-4 and Y is optionally substituted $C_3$-$C_8$-cycloalkyl; optionally substituted 3 to 8 membered heterocyclyl; optionally substituted aryl; optionally substituted heteroaryl, optionally substituted $C_1$-$C_6$-alkoxy; —C(O)OH or —C(O)N(R$^8$)$_2$; preferably $R_3$ is H or optionally substituted methyl;

each $R^8$ is independently H or $C_1$-$C_6$-alkyl; and
X is N or CR$^5$; wherein $R^5$ is H or optionally substituted $C_{1-6}$ alkyl; preferably X is N.

The present further provides methods of treating or slowing the progression or development of an autoimmune disease in a subject suffering from, or at risk of developing, the autoimmune disease, comprising administering the subject a therapeutically effective amount of one or more compounds of the invention. The autoimmune disease can be, for example, celiac disease, type 1 diabetes (T1D), Stiff-person Syndrome (SPS), Addison's disease (AD), Schmidt Syndrome (SS), or Myasthenia Gravis (MG). The present invention further provides pharmaceutical compositions comprising a compound of the invention and a pharmaceutically acceptable carrier or excipient.

These compounds of the invention are believed to inhibit the binding of an antigenic peptide to the DQ2 MHC class II molecule for presentation to CD4+ T cells, and are useful for slowing the development or progression of an autoimmune disease. The inhibition of the binding of an antigenic peptide to a DQ2 MHC class II molecule may result from a distortion of the spatial orientation of the complex so that the DQ2 MHC class II molecule-antigen complex is not properly presented to T cells, such that the trimolecular complex between 1) the MHC class II molecule on the surface of an antigen presenting cell, 2) the antigenic peptide, and 3) the CD4+ T cell, is not formed.

In another embodiment, the invention provides a method of treating an autoimmune disease in a subject, including selecting a subject for treatment with one or more compounds of the invention on the basis of the subject having at least one of the diagnostic criteria of the autoimmune disease. Such diagnostic criteria may include, for celiac disease, mucosal changes detected by duodenal biopsy and positivity of serological tests (anti-transglutaminase antibodies (tTG), anti-endomysium antibodies (EmA), and/or deamidated gliadin peptide (DGP) antibodies). For T1D, such diagnostic criteria may include the detection of autoantibodies directed toward insulin (IAA) and beta cell-specific antigens, glutamic acid decarboxylase 65 (GAD65), insulinoma-associated antigen 2 (IA-2) and zinc transporter 8 (ZnT8), and/or a previous diagnosis of celiac disease. For Stiff-person syndrome, such diagnostic criteria may include the detection of autoantibodies directed toward glutamic acid decarboxylase (GAD). For Addison's disease, such diagnostic criteria may include the finding of low blood levels of sodium or high levels of potassium, positive ACTH stimulation test, insulin-induced hypoglycemia test, and/or x-ray examination. For Schmidt syndrome, such diagnostic criteria may include the diagnosis of two or more of Addison's disease, autoimmune hypothyroidism, and/or T1DM. For Myasthenia Gravis, such diagnostic criteria may include detection of autoantibodies directed toward the acetylcholine receptor. Upon detection of one or more of these criteria diagnostic of a specific autoimmune disease, the subject is selectively administered a compound of the invention.

In certain embodiments of the methods of the invention, the subject has been tested for the presence of antibodies directed to an antigen selected from a gliadin peptide, insulin (IAA), a beta cell-specific antigen, glutamic acid decarboxylase (GAD), insulinoma-associated antigen 2 (IA-2), zinc transporter 8 (ZnT8), and the acetylcholine receptor, wherein the presence of such antibodies in the subject is indicative of the presence or likely development of an autoimmune disease. Thus, a related aspect of the invention provides methods of treating a subject found to have such autoantibodies by administering a compound of the invention to the subject.

Another aspect of the invention provides methods of monitoring and adjusting the dosage of a compound of the invention administered to a subject suffering from, or at risk of developing, an autoimmune disease, including receiving a blood sample from a subject suffering from, or at risk of developing, the autoimmune disease who has been administered a compound of the invention and determining the DQ2-stimulated response of ICD4+ T cells in the blood sample. The DQ2-stimulated response of CD4+ T cells in the blood sample is compared to a control level of DQ2-stimulated response of CD4+ T cells in blood samples from at least one of a patient suffering from the autoimmune disease and a control or 'wild type' subject known to be free of the autoimmune disease. The dosage and/or the frequency of the compound of the invention administered to the subject is increased if the DQ2-stimulated response of CD4+ T cells in the blood sample from the subject is statistically similar to the DQ2-stimulated response of CD4+ T cells from the baseline level in the celiac disease patient.

Other aspects of the invention will be set forth in the accompanying description of embodiments, which follows and will be apparent from the description. However, the following Detailed Description is given by way of illustration only, as various changes and modifications within the spirit and scope of the invention will become apparent to those skilled in the art and are encompassed within the scope of the invention.

DETAILED DESCRIPTION OF THE INVENTION

The present invention relates to compounds of Formula (I) and methods of use thereof for treating or slowing the progression or development of an autoimmune disease.

In certain embodiments, the compounds of Formula (I) have the stereochemistry set forth in Formula (Ia) or Formula (Ib),

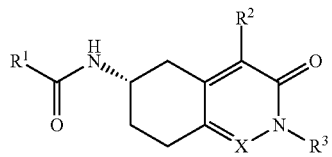
(Ia)

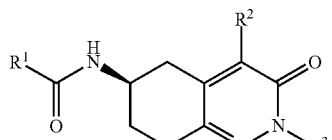
(Ib)

where X, Y, R¹, R² and R³ are as defined above. A composition of the invention, such as a pharmaceutical composition, can comprise a compound of the invention as a racemic mixture of Formula (Ia) and Formula (Ib), a pure enantiomer of either Formula (Ia) or Formula (Ib), or an excess of one enantiomer over the other. For example, the composition can comprise the compound in an enantiomeric excess of at least 5, 10, 20, 30, 40, 50, 60, 70, 80 or 90% of Formula (Ia) or Formula (Ib). In one embodiment, the enantiomeric excess is at least 95%. In compounds of the invention having two or more chiral atoms, such compounds can be present in a composition, such as a pharmaceutical composition, as a pure stereoisomer or a mixture of stereoisomers, such as a racemic mixture or a mixture of diastereomers. In one embodiment, a composition of the invention comprises a racemic mixture, a single stereoisomer or enantiomers with an enantiomeric excess of at least 5, 10, 20, 30, 40, 50, 60, 70, 80, 90 or 95% of one enantiomer.

In certain embodiments, the invention provides compounds of Formula (I), as described above, and pharmaceutically acceptable salts thereof. In certain embodiments, the compounds of Formula (I) do not include the compounds set forth below.

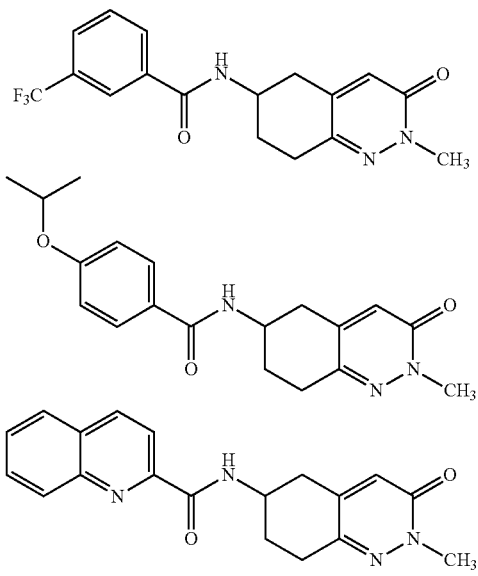

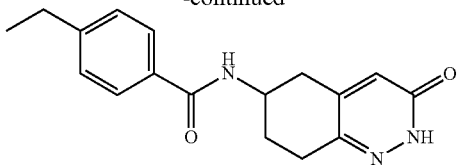

In certain embodiments of the compounds of Formula (I), $R^1$ is H; $C_1$-$C_4$-alkyl, preferably methyl, ethyl, n-propyl, isopropyl, n-butyl, sec-butyl; halo-$C_1$-$C_4$-alkoxy, $C_{3-7}$ cycloalkyl; or

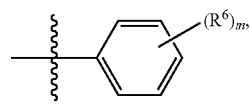

wherein m is 0 to 5, preferably 0 to 2 or 1; each $R^6$ is independently $C_1$-$C_4$-alkyl, preferably methyl, ethyl, n-propyl, isopropyl, n-butyl, sec-butyl; halo-$C_1$-$C_4$-alkyl, $C_1$-$C_4$-alkoxy, halo-$C_1$-$C_4$-alkoxy, or $C_{3-7}$ cycloalkyl; in certain embodiments, $R^1$ is

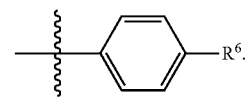

In certain embodiments of the compounds of Formula (I), $R^1$ is methyl, ethyl, n-propyl, isopropyl, n-butyl, sec-butyl, t-butyl, naphthyl, quinolyl, cyclopropyl, cyclohexyl; or

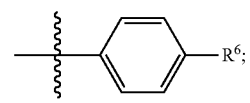

where $R^6$ is halogen; trifluoromethyl, methyl, ethyl, n-propyl, isopropyl, n-butyl, sec-butyl, t-butyl or cyclohexyl;

In certain embodiments of the compounds of Formula (I), $R^2$ is H, $C_{1-4}$ alkyl, or $OR^4$, wherein $R^4$ is H, or $C_{1-4}$ alkyl. Preferably $R^1$ is H.

In certain embodiments of the compounds of Formula (I), $R^3$ is H, $CH_3$, $CH_2CH_3$, $CH_2CH_2CH_3$, or $CH(CH_3)_2$; or $R^3$ is H; $CH_3$; $CH_2CH_3$; $CH_2CH_2CH_3$; $CH(CH_3)_2$; $CH_2CH(CH_3)_2$; $C_3$-$C_6$-cycloalkyl; saturated 5-6-membered heterocyclyl, preferably tetrahydropyranyl, such as 4-tetrahydropyranyl; or —$(CH_2)_n$—Y, where n is 1-4, preferably 1 or 2; and Y is optionally substituted phenyl; $C_3$-$C_6$-cycloalkyl; saturated 5-6-membered heterocyclyl, preferably tetrahydropyranyl, such as 4-tetrahydropyranyl; C(O)OH or C(O)(NR⁸)₂, where each $R^8$ is as defined above; preferably, each $R^8$ is independently H or methyl.

In certain embodiments of the compounds of Formula (I), X is N or $CR^5$, wherein $R^5$ is H or $C_{1-4}$ alkyl. Preferably X is N.

In certain embodiments of the compounds of Formula (I), $R^1$ is H; $C_1$-$C_4$-alkyl, preferably methyl, ethyl, n-propyl, isopropyl, n-butyl or sec-butyl; halo-$C_1$-$C_4$-alkoxy, $C_{3-7}$ cycloalkyl; or $R^1$ is methyl, ethyl, n-propyl, isopropyl, n-butyl, sec-butyl, t-butyl, naphthyl, quinolyl, cyclopropyl, cyclohexyl; or $R^1$

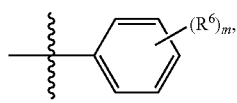

wherein m is 0 to 5, preferably 0 to 2 or 1; each $R^6$ is independently halogen; preferably chloro or fluoro; $C_1$-$C_4$-alkyl, preferably methyl, ethyl, n-propyl, isopropyl, n-butyl or sec-butyl; halo-$C_1$-$C_4$-alkyl, $C_1$-$C_4$-alkoxy, halo-$C_1$-$C_4$-alkoxy, or $C_{3-7}$ cycloalkyl; or each $R^6$ is independently halogen; preferably chloro or fluoro; $C_1$-$C_4$-alkyl, preferably methyl, ethyl, n-propyl, isopropyl, n-butyl, sec-butyl or t-butyl; halo-$C_1$-$C_4$-alkyl, such as trifluoromethyl; $C_1$-$C_4$-alkoxy, halo-$C_1$-$C_4$-alkoxy, or $C_{3-7}$ cycloalkyl, such as cyclohexyl; in certain embodiments, $R^1$ is

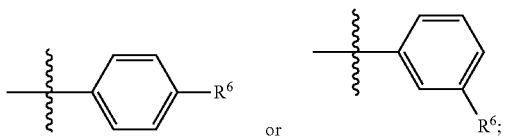

$R^2$ is H, $C_{1-4}$ alkyl, or $OR^4$, wherein $R^4$ is H, or $C_{1-4}$ alkyl; preferably $R^2$ is hydrogen; $R^3$ is H, $CH_3$, $CH_2CH_3$, $CH_2CH_2CH_3$, or $CH(CH_3)_2$; or $R^3$ is H; $CH_3$; $CH_2CH_3$; $CH_2CH_2CH_3$; $CH(CH_3)_2$; $CH_2CH(CH_3)_2$; $C_3$-$C_6$-cycloalkyl; saturated 5-6-membered heterocyclyl, such as tetrahydropyranyl, including 4-tetrahydropyranyl; or —$(CH_2)_n$—Y, where n is 1-4, preferably 1 or 2; and Y is optionally substituted phenyl; $C_3$-$C_6$-cycloalkyl; saturated 5-6-membered heterocyclyl, preferably tetrahydropyranyl, such as 4-tetrahydropyranyl; C(O)OH or C(O)$(NR^8)_2$, where each $R^8$ is as defined above; preferably, each $R^8$ is independently H or methyl; and X is N or $CR^5$, wherein $R^5$ is H or $C_{1-4}$ alkyl. Preferably X is N.

In another embodiment, the invention provides compounds of Formula (II),

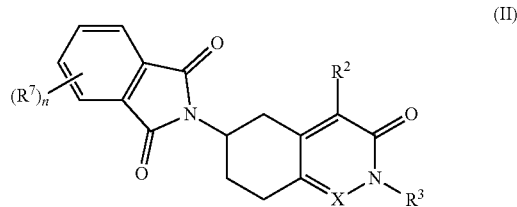

and pharmaceutically acceptable salts thereof,
wherein $R^2$, $R^3$ and X are as defined above, $R^7$ is halo, hydroxyl, $C_1$-$C_4$-alkyl, halo-$C_1$-$C_4$-alkyl, $C_1$-$C_4$-alkoxy, or halo-$C_1$-$C_4$-alkoxy and n is 0 to 4.

Protected derivatives of the compounds of the invention also are contemplated. In general, protecting groups are removed under conditions which will not affect the remaining portion of the molecule. These methods are well known in the art and include acid hydrolysis, hydrogenolysis, and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known, and suitable protecting groups can be selected by those of skill in the art in consultation with Greene and Wuts, Protective Groups in Organic Synthesis; 3rd Ed.; John Wiley & Sons, New York, 1999. When an acid moiety, such as a phosphonic acid moiety is unveiled, the compound may be isolated as the acid compound or as a salt thereof.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can be synthesized using methods known in the art, for example by employing deuterated starting materials. Unless stated to the contrary, the isotopically labelled compounds are pharmaceutically acceptable.

Definitions

The singular terms "a," "an," and "the" include plural referents unless context clearly indicates otherwise. Similarly, the word "or" is intended to include "and" unless the context clearly indicates otherwise. The term "comprises" means "includes." Also, "comprising A or B" means including A or B, or A and B, unless the context clearly indicates otherwise. It is to be further understood that all molecular weight or molecular mass values given for compounds are approximate and are provided for description. Although methods and materials similar or equivalent to those described herein can be used in the practice or testing of the invention, suitable methods and materials are described below. In addition, the materials, methods, and examples are illustrative only and not intended to be limiting.

"Administration of" and "administering a" compound or agent should be understood to mean providing a compound or agent, a prodrug of a compound or agent, or a pharmaceutical composition as described herein. The compound, agent or composition can be administered by another person to the subject (e.g., intravenously) or it can be self-administered by the subject (e.g., tablets or capsules). Where two or more compounds are administered, co-administration is typically preferred with the co-administration being either via a combination formulation, or via parallel or subsequent administration of the two compounds. More typically, sequential co-administration will be performed such that the first compound is present in the patient's body in measurable quantities when the second compound is administered.

The term "solvate" refers to a solid crystalline form of a compound which includes molecules of a solvent within the crystal lattice. Suitable solvates include those with pharmaceutically acceptable solvents, such as ethanolates and hydrates, including monohydrates and hemi-hydrates.

The term "gluten peptide" or "gliadin peptide" is used to denote a peptide fragment of a gluten protein. Although the fragment is typically a subset of the amino acid sequence of a gluten protein, a gluten peptide may contain the entire amino acid sequence of a naturally occurring gluten protein.

The terms "individual" and "subject" are used interchangeably herein and refer to an animal, such as a mammal, including a non-primate (e.g., a cow, pig, horse, cat, dog, rat, and mouse), a nonhuman primate (e.g., a monkey such as a cynomolgus monkey, a chimpanzee), and a human. In certain embodiments, the subject is refractory or non-responsive to current treatments for an autoimmune disease, such as celiac disease, T1D, SPS, AD, SS, and MG.

"Tissue" means any biological sample taken from any individual, preferably a human. Tissues include blood, saliva, urine, biopsy samples, skin or buccal scrapings, and hair.

Persons of skill in the art will appreciate that blood plasma drug concentrations obtained from individual subjects will vary due to inter-patient variability in the many parameters affecting drug absorption, distribution, metabolism, and excretion. For this reason, unless otherwise indicated, when a drug plasma concentration is listed, the value listed is the calculated mean value based on values obtained from a group of subjects tested.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

Pharmaceutically acceptable salts are well known in the art. For example, S. M. Berge, et al. describe pharmaceutically acceptable salts in detail in J. Pharmaceutical Sciences, 66: 2-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphor sulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The term "therapeutically-effective amount" of compounds of the invention means an amount effective to modulate the formation or progression of autoimmune diseases celiac disease in an individual.

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "alkyl" as used herein, refers to saturated, straight- or branched-chain hydrocarbon radicals. Exemplary alkyl groups include "$C_1$-$C_4$ alkyl," "$C_1$-$C_6$ alkyl," "$C_1$-$C_8$ alkyl," "$C_1$-$C_{12}$ alkyl," "$C_2$-$C_4$ alkyl," or "$C_3$-$C_6$ alkyl," which refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. Exemplary alkenyl groups include "$C_2$-$C_8$ alkenyl," "$C_2$-$C_{12}$ alkenyl," "$C_2$-$C_4$ alkenyl," "$C_3$-$C_4$ alkenyl," or "$C_3$-$C_6$ alkenyl," which refer to alkenyl groups containing from two to eight, two to twelve, two to four, three to four or three to six carbon atoms respectively. Alkenyl groups include, but are not limited to, for example, ethenyl, propenyl, butenyl, 2-methyl-2-buten-2-yl, heptenyl, octenyl, and the like.

The term "alkynyl" as used herein, refers to straight- or branched-chain hydrocarbon radicals having at least one carbon-carbon triple bond by the removal of a single hydrogen atom. Exemplary alkynyl groups include "$C_2$-$C_8$ alkynyl," "$C_2$-$C_{12}$ alkynyl," "$C_2$-$C_4$ alkynyl," "$C_3$-$C_4$ alkynyl," or "$C_3$-$C_6$ alkynyl," which refer to alkynyl groups containing from two to eight, two to twelve, two to four, three to four or three to six carbon atoms respectively. Representative alkynyl groups include, but are not limited to, for example, ethynyl, 2-propynyl, 2-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-2-enyl, bicyclo[4.2.1]non-3-en-12-yl, and the like.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 2-propoxy, 2-propoxy (isopropoxy) and the higher homologs and isomers. Preferred alkoxy are ($C_2$-$C_3$) alkoxy.

The terms "heterocyclyl" and "heterocycloalkyl" can be used interchangeably and refer to a non-aromatic ring, for example, a 3- to 12 membered ring, or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 2-oxa-7-azaspiro[4.4]nonanyl, 7-oxooxepan-4-yl, and tetrahydrofuryl. Such heterocyclyl groups may be further substituted. Heteroaryl or heterocyclyl groups can be C-attached or N-attached (where possible).

It is understood that any alkyl, alkenyl, alkynyl, alicyclic, cycloalkyl, cycloalkenyl, aryl, heteroaryl, heterocyclyl, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —$NO_2$, —$N_3$, —CN, —$NH_2$, protected amino, oxo, thioxo, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)— heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH— heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$-aryl, $CO_2$-heteroaryl, $CO_2$-heterocyloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2$NH—$C_1$-$C_{12}$-alkyl, —$SO_2$NH—$C_2$-$C_8$-alkenyl, —$SO_2$NH—$C_2$-$C_8$-alkynyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S-aryl, —S-heteroaryl, —S-heterocycloalkyl, or methylthio-methyl. In certain embodiments, the substituents are independently selected from halo, preferably Cl and F; C$_1$-C$_4$-alkyl, preferably methyl and ethyl; halo-C$_1$-C$_4$-alkyl, such as fluoromethyl, difluoromethyl, and trifluoromethyl; C$_2$-C$_4$-alkenyl; halo-C$_2$-C$_4$-alkenyl; C$_3$-C$_6$-cycloalkyl, such as cyclopropyl; C$_1$-C$_4$-alkoxy, such as methoxy and ethoxy; halo-C$_1$-C$_4$-alkoxy, such as fluoromethoxy, difluoromethoxy, and trifluoromethoxy; —CN; —OH; NH$_2$; C$_1$-C$_4$-alkylamino; di(C$_1$-C$_4$-alkyl)amino; and NO$_2$. It is understood that the aryls, heteroaryls, alkyls, and the like can be further substituted. In some cases, each substituent in a substituted moiety is additionally optionally substituted with one or more groups, each group being independently selected from C$_1$-C$_4$-alkyl; —CF$_3$, —OCH$_3$, —OCF$_3$, —F, —Cl, —Br, —I, —OH, —NO$_2$, —CN, and —NH$_2$. Preferably, a substituted alkyl group is substituted with one or more halogen atoms, more preferably one or more fluorine or chlorine atoms.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydroxyl activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, Protective Groups in Organic Synthesis, 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, Prodrugs, Topical and Ocular Drug Delivery, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, Protective Groups in Organic Synthesis, 3rd edition, John Wiley & Sons, New York (1999). Examples of amino protecting groups include, but are not limited to, methoxycarbonyl, t-butoxycarbonyl, 12-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: Organic Solvents Physical Properties and Methods of Purification, 4th ed., edited by John A. Riddick et al., Vol. II, in the Techniques of Chemistry Series, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

Pharmaceutical Compositions

The pharmaceutical compositions of the present invention comprise a therapeutically effective amount of a compound of the present invention Formulated together with one or more pharmaceutically acceptable carriers. As used herein, the term "pharmaceutically acceptable carrier" means a non-toxic, inert, solid, semi-solid or liquid filler, diluent, encapsulating material or Formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols, such as propylene glycol; esters, such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the Formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the Formulation may be adjusted with pharmaceutically acceptable acids, bases or buffers to enhance the stability of the Formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable Formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical Formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic Formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The methods provided herein encompass administering pharmaceutical compositions containing compounds of this disclosure, if appropriate in the salt form, either alone or in the form of a combination with one or more compatible and pharmaceutically acceptable carriers, such as diluents or adjuvants, or with another therapeutic agent. The second or additional therapeutic agent can be formulated or packaged with a compound of the invention. The second agent will only be formulated with a compound of the invention according to the judgment of those of skill in the art, as such co-formulation should not interfere with the activity of either agent or the method of administration. The compound of the invention and the second agent may be formulated separately. They may also be packaged together, or packaged separately, for the convenience of the medical practitioner.

A preferred formulation of the invention is a mono-phasic pharmaceutical composition suitable for oral administration for the treatment, prophylaxis, or for slowing the progression or for delaying the onset of an autoimmune disease, consisting essentially of a therapeutically-effective amount of a compound of the invention, and a pharmaceutically acceptable carrier.

Methods of Use

Provided herein are methods for the treatment and/or prophylaxis of an autoimmune disease in a subject. These methods include the treating a subject suffering from an autoimmune disease by the administration of an effective amount of a compound of the invention. In these methods, the autoimmune disease may be associated with the occurrence of certain DQ2 alleles. In these methods, the autoimmune disease can be, but is not limited to, one or more of celiac disease, T1D, SPS, AD, SS, and MG. These methods may encompass the step of administering to the individual in need of such treatment an amount of a compound of the invention effective for treating or delaying the development or progression of the autoimmune disease. The compounds of the invention that may be administered to an individual in these methods may be in the form of a pharmaceutical composition or single unit dosage form, as described above.

The invention includes methods of treating or slowing the progression or development of an autoimmune disease by reducing or preventing the binding of WIC class II molecules to antigenic peptides or fragments of antigenic peptides of the autoimmune disease by the administration of a compound of the invention to individuals suffering from, or at risk of developing, the autoimmune disease.

A specific method includes treating celiac disease in an individual comprising administering an effective amount of a compound of the invention to an individual in need of such treatment.

Another method provided herein includes treating an individual at risk of developing an autoimmune disease by administering an effective amount of a compound of the invention to the individual. Thus, the invention provides for the use of a compound of the invention in the manufacture of a medicament for the treatment of an autoimmune disease. In this use, the autoimmune disease may be one or more of celiac disease, T1D, SPS, AD, SS, and MG. The invention also provides a compound of the invention for use in the treatment of an autoimmune disease selected from one or more of celiac disease, T1D, SPS, AD, SS, and MG.

In these methods, a compound of the invention can be administered orally to the subject. The compound of the invention may be administered to an individual once daily, or more frequently. The compound of the invention can be administered to a subject as a pharmaceutically acceptable salt, solvate, or hydrate thereof. The compound of the invention, or a pharmaceutically acceptable salt thereof, may be administered to a subject as a pharmaceutical composition, as described above.

In the methods of treating or slowing the progression or development of an autoimmune disease of the invention, a compound of the invention or a pharmaceutically acceptable salt thereof, is administered to a subject suspected of suffering from, or at risk of developing the autoimmune disease. Preferably, the administration to a subject diagnosed with the autoimmune disease commences within 5 years of the initial diagnosis of the autoimmune disease in the subject, or more preferably, within 1 year of the initial diagnosis of the autoimmune disease in the subject, or more preferably, within 6 months of the initial diagnosis of the autoimmune disease in the subject, or more preferably, within 1 month of the initial diagnosis of the autoimmune disease in the subject.

In any of these methods, the subject may be administered a dosage of a compound of the invention, or a pharmaceutically acceptable salt, solvate, or hydrate thereof, that is therapeutically effective to treat or delay the development or progression of the autoimmune disease in the subject.

Another aspect of these methods includes an initial determination of which patients may benefit from the administration of a compound of the invention, prior to administration of a compound of the invention to the subject determined to be in need of such treatment. As described above, DQ2 alleles confer significant risk of several autoimmune diseases. Thus, subjects with certain known DQ2 alleles are subjects at risk of developing an autoimmune disease. Additionally, subjects with anti-transglutaminase antibodies, EmA anti-endomysium antibodies, and/or antibodies against deamidated gliadin peptides, or autoantibodies that recognize an WIC class II molecule bound to a gliadin peptide, or to gliadin peptide fragment(s), wherein the presence of such antibodies in the subject is indicative of the presence or likely development of celiac disease in that subject. Such subject therefore may benefit from the administration of a compound of the invention, as described above.

The determination of which DQ2 alleles are present in a subject may enable a clinician to establish the subject's risk of developing an autoimmune disease. For example, the finding of a heterozygote of a high risk DQ2 genotype in the subject may be used to modify the dosage and/or dosing regimen of a compound of the invention to the subject, which may include reducing the dose or frequency of administration of a compound of the invention to the subject. Alternatively, if the genotyping methods of the invention reveal homozygous wild type HLA alleles, in a nucleic acid sample obtained from the subject, then the clinician may rule out an elevated risk of developing an autoimmune disease in the subject and consider different treatments or diagnoses for that subject.

A number of methods are available for analyzing and determining the DQ2 and/or DQ8 genotype in a subject, which can be applied to a nucleic acid sample obtained from a subject. Assays for detection of polymorphisms or mutations fall into several categories, including but not limited to, direct sequencing assays, fragment polymorphism assays, hybridization assays, and computer-based data analysis. Protocols and kits or services for performing these general methods are commercially available and well known to those of skill in the art. In some embodiments, assays are performed in combination or in hybrid (e.g., different reagents or technologies from several assays are combined to yield one assay). Thus, the presence or absence of DQ8 and/or DQ2 alleles may be determined using direct sequencing. Alternatively or additionally, the DQ8 and/or DQ2 alleles may be determined using a PCR-based assay using oligonucleotide primers to amplify a DNA fragment containing the DQ8 and/or DQ2 polymorphism of interest. Alternatively or additionally, the DQ8 and/or DQ2 alleles may be determined using a fragment length polymorphism assay, such as a restriction fragment length polymorphism assay (RFLP), to detect a unique DNA banding pattern indicative of an DQ8 and/or DQ2 genotype based on cleaving the DNA at a series of positions is generated using an enzyme (e.g., a restriction endonuclease). Alternatively or additionally, the DQ8 and/or DQ2 alleles may be determined using a hybridization assay, wherein the genotype is determined based on the ability of the DNA from the sample to hybridize to a complementary DNA molecule (e.g., an oligonucleotide probe). The DQ8 and/or DQ2 polymorphisms of interest may be detected using a DNA chip hybridization assay, in which a series of oligonucleotide probes, designed to be unique to a given single nucleotide polymorphism, are affixed to a solid support, and the nucleic acid sample from the subject is contacted with the DNA "chip" and hybridization is detected. Alternatively or additionally, the DQ8 and/or DQ2 alleles may be determined using a "bead array" (such as those described in PCT Publications WO99/67641 and WO00/39587, each of which is herein incorporated by reference). Alternatively or additionally, the DQ8 and/or DQ2 alleles may be determined using an assay that detects hybridization by enzymatic cleavage of specific structures (such as those assays described in U.S. Pat. No. 6,001,567, and Olivier, M., The Invader assay for SNP Genotyping, 2005 Mutat. Res. 573 (1-2):103-10, both of which are incorporated herein by reference).

Any known method of analyzing a sample for an analyte can be used to practice the present invention, so long as the method detects the presence, absence, or amount of autoimmune disease-associated antibodies, such as anti-gluten protein antibodies, anti-transglutaminase antibodies, antibodies against deamidated gliadin peptides, acetylcholine receptor antibodies, and/or anti-endomysium antibodies. Examples of such methods include, but are not limited to, immunological detection assays and non-immunological methods (e.g., enzymatic detection assays). Alternatively or additionally, a binding compound is immobilized on a substrate, such as a microtiter dish well, a dipstick, an immunodot strip, or a lateral flow apparatus. A sample collected from a subject is applied to the substrate and incubated under conditions suitable to allow the formation of a complex between the binding compound and any antibody present in the sample. Once formed, the complex is then detected. Complex formation, or selective binding, between an antibody and a binding compound can be measured (i.e., detected, determined) using a variety of methods standard in the art including, but not limited to, an enzyme-linked immunoassay, a competitive enzyme-linked immunoassay, a radioimmunoassay, a fluorescence immunoassay, a chemiluminescent assay, a lateral flow assay, a flow-through assay, an agglutination assay, a particulate-based assay (e.g., using particulates such as, but not limited to, magnetic particles or plastic polymers, such as latex or polystyrene beads), an immunoprecipitation assay, a BIA-CORE™ assay (e.g., using colloidal gold), an immunodot assay (e.g., CMG's Immunodot System, Fribourg, Switzerland), and an immunoblot assay (e.g., a western blot), an phosphorescence assay, a flow-through assay, a chromatography assay, a PAGE-based assay, a surface plasmon resonance assay, a spectrophotometric assay, a particulate-based assay, and an electronic sensory assay. The assays may be used to give qualitative or quantitative results. The assay results can be based on detecting the entire antibody or fragments, or degradation products. Some assays, such as agglutination, particulate separation, and immunoprecipitation, can be observed visually (e.g., either by eye or by a machine, such as a densitometer or spectrophotometer) without the need for a detectable marker. A detectable marker can be conjugated to the compound or reagent at a site that does not interfere with the ability of the compound to bind antibodies. Methods of conjugation are known to those of skill in the art. Examples of detectable markers include, but are not limited to, a radioactive label, a fluorescent label, a chemiluminescent label, a chromophoric label, an enzyme label, a phosphorescent label, an electronic label, a metal sol label, a colored bead, a physical label, or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or IMMUNOPURE™ NeutrAvidin). Means of detecting such markers are well known to those of skill in the art.

For example, a tri-molecular complex between a gliadin antigen, an MHC molecule, and T cell receptor can be detected by contacting a biological sample from a subject with an antibody specific for the complex, wherein the antibody is conjugated to a detectable marker. A detectable marker can also be conjugated to a tri-molecular complex between a gliadin antigen, an MHC molecule, and T cell receptor such that contact of the labeled complex with a biological sample from a subject can detect the presence of antibodies to the complex present in the subject tested. Detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or IMMUNOPURE™ NeutrAvidin).

A tri-molecular complex may be detected by contacting the complex with an indicator molecule. Suitable indicator molecules include molecules that can bind to the tri-molecular binding molecule complex. As such, an indicator molecule can comprise, for example, an antibody. Preferred indicator molecules that are antibodies include, for example, antibodies reactive with the antibodies from animals in which the antibodies are produced. An indicator molecule itself can be attached to a detectable marker of the present invention. For example, an antibody can be conjugated to biotin, horseradish peroxidase, alkaline phosphatase or fluorescein. One or more layers and/or types of secondary molecules or other binding molecules capable of detecting the presence of an indicator molecule may be used. For example, an untagged (i.e., not conjugated to a detectable marker) secondary antibody that selectively binds to an indicator molecule can be bound to a tagged (i.e., conjugated to a detectable marker) tertiary antibody that selectively binds to the secondary antibody. Suitable secondary antibodies, tertiary antibodies and other secondary or tertiary molecules can be readily selected by those skilled in the art. Preferred tertiary molecules can also be selected by those skilled in the art based upon the characteristics of the secondary molecule. The same strategy can be applied for subsequent layers.

A lateral flow assay may be used for detection, examples of which are described in U.S. Pat. Nos. 5,424,193; 5,415,994; WO 94/29696; and WO 94/01775 (all of which are incorporated by reference herein).

Once a biological sample from a subject has been analyzed to determine which DQ2 allele is present, the subject can be selected, or identified, as likely or unlikely to develop, or at higher or lower risk of developing, an autoimmune disease. Such a selection is made using the results from the analysis step of the disclosed methods. Those subjects selected as likely or at higher risk of developing an autoimmune disease may be treated with one or more compounds of the invention to treat or slow the development of the autoimmune disease in the subject.

Each publication or patent cited herein is incorporated herein by reference in its entirety. Additional objects, advantages, and novel features of the invention will become apparent to those skilled in the art upon examination of the following examples, which are not intended to be limiting.

EXAMPLES

Example 1 Synthesis and Characterization of Exemplary Compounds

Compounds of Formulas I and II were synthesized using the general methods described below.

Synthesis of Inhibitors

Scheme 1: Synthesis of intermediate 7-amino-2-methyl-5,6,7,8-tetrahydrocinnolin-3-one, IV

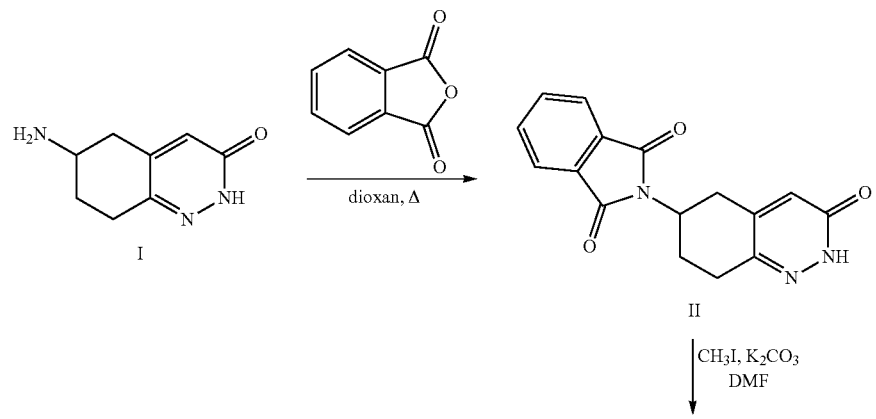

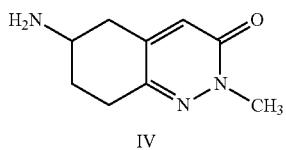
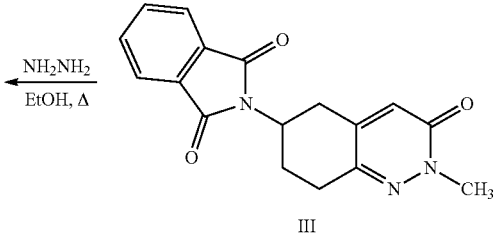
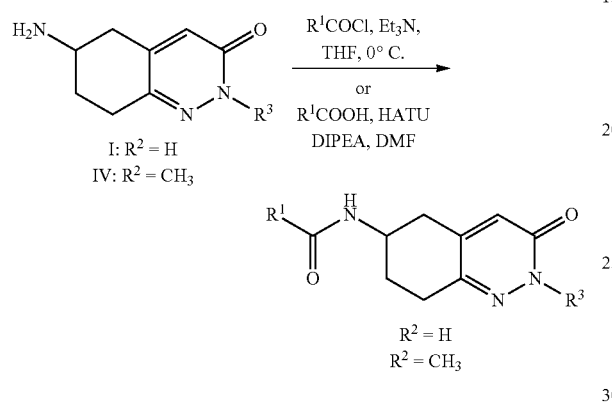
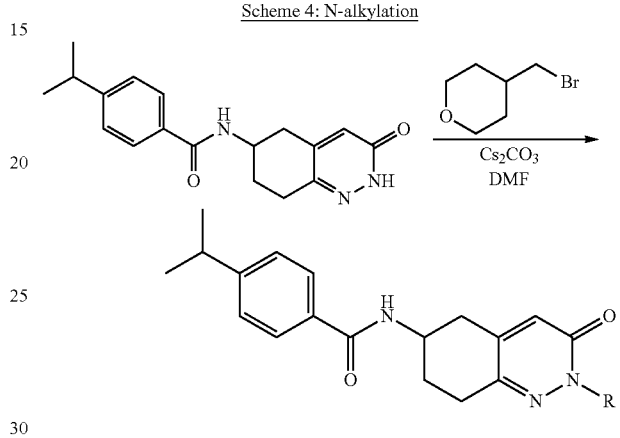
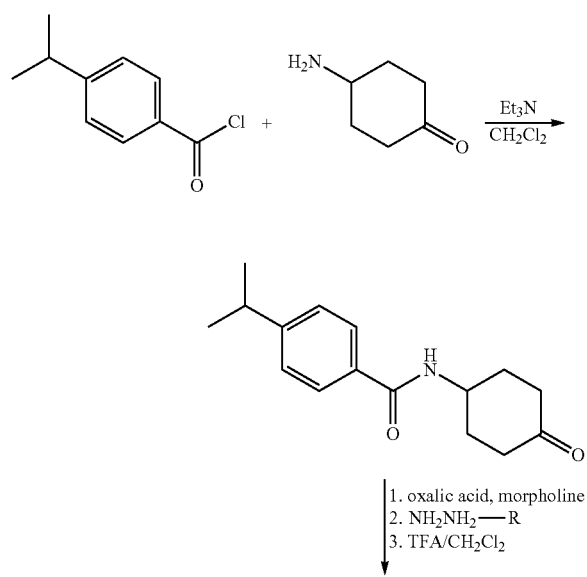

Step 1 Scheme 1

2-(3-oxo-5,6,7,8-tetrahydro-2H-cinnolin-7-yl)isoindoline-1,3-dione, (II and 26)

To a stirred suspension of commercially available 7-amino-5,6,7,8-tetrahydro-2H-cinnolin-3-one dihydrochloride, 1 (0.40 g, 1.67 mmol) in anhydrous dioxane (4 mL) was added triethylamine (1.2 mL, 8.60 mmol. 5 equiv.), dropwise at 0° C. The reaction mixture was warmed to RT and stirred for an additional 10 min. Phthalic anhydride (0.28 g, 1.67 mmol, 1.0 equiv.) was added in one portion at RT. After 10 min., the reaction mixture was heated to 100° C. for 3 h. After cooling to room temperature, the mixture was concentrated to one fourth of its volume and filtered. The crude solid was washed with minimum cold methylene chloride and dried in vacuo to afford 2-(3-oxo-5,6,7,8-tetrahydro-2H-cinnolin-7-yl)isoindoline-1,3-dione, (II), as an off-white solid (0.43 g, 86%). $^1$H NMR (300 MHz, CDCl$_3$): δ 2.10 (m, 1H), 2.6~3.1 (set of m, 4H), 3.60 (dd, J=17, 5.4 Hz, 1H), 4.60 (m, 1H), 6.75 (s, 1H), 7.75 and 7.85 (two m, 4H): LC/MS (C$_{16}$H$_{13}$N$_3$O$_{33}$): RT 3.45 min: m/z 296.1 (M+1); m/z 296 (M+1).

Step 2 Scheme 1

2-(2-methyl-3-oxo-5,6,7,8-tetrahydrocinnolin-7-yl) isoindoline-1,3-dione, (III and 27)

To solution of 2-(3-oxo-5,6,7,8-tetrahydro-2H-cinnolin-7-yl)isoindoline-1,3-dione, 2 (0.60 g, 2.0 mmol) in anhydrous DMF (5 mL), was treated with anhydrous potassium carbonate (0.42 g, 3.04 mmol, 1.5 equiv.). After stirring for 10 min, the mixture was cooled to 0° C. followed by addition of iodomethane (1.5 mL of 10% solution in DMF, 2.42 mmol, 1.2 equiv.) dropwise. Upon completion of the addition, the reaction mixture was allowed to warm to room temperature and stirred for 14 h. The reaction was cooled to 0° C., quenched with water (5 mL) and extracted in DCM. The combined organic layers were dried ($Na_2SO_4$) and the solvent was removed in vacuo. The product was purified by column chromatography (24 g silica, 0-10% MeOH/$CH_2Cl_2$) to afford 2-(2-methyl-3-oxo-5,6,7,8-tetrahydrocinnolin-7-yl)isoindoline-1,3-dione (III), as a white solid (0.53 g, 84%). $^1$H NMR (300 MHz, $CDCl_3$): δ 2.05 (m, 1H), 2.6~3.0 (set of m, 4H), 3.55 (dd, J=17, 5.4 Hz, 1H), 3.75 (s, 3H), 4.50 (m, 1H), 6.65 (s, 1H), 7.75 and 7.85 (two d, 4H). $^{13}$C NMR (300 MHz, $CDCl_3$): δ 26.7, 28.9, 31.3, 40.0, 46.1, 123.6, 127.0, 131.9, 134.5, 141.7, 143.7, 160.5, 168.3. LC/MS: ($C_{17}H_{15}N_3O_3$): RT 3.62 min; m/z 310 (M+1).

Step 3 Scheme 1

7-amino-2-methyl-5,6,7,8-tetrahydrocinnolin-3-one, (IV)

To a solution of 2-(2-methyl-3-oxo-5,6,7,8-tetrahydrocinnolin-7-yl)isoindoline-1,3-dione, 3 (0.50 g, 1.61 mmol) in ethanol (4 mL) was treated with hydrazine (1100 μL, excess) and then heated to 70° C. for 1 h. The reaction was cooled to room temperature and concentrated. The oil was passed through a Silica SPE column with 40% methanol/methylene chloride and the eluent was concentrated in vacuo. The product was purified by reverse phase chromatography (55 g C18 AQ, 0-100% acetonitrile/water with 0.1% formic acid), to afford after lyophilization 7-amino-2-methyl-5,6,7,8-tetrahydrocinnolin-3-one (IV) as a white solid (0.25 g, 86%). LC/MS ($C_9H_{13}N_3O$): RT 0.94 min; m/z 180 (M+1).

Scheme 2: Acid Chloride Method: Compound 16

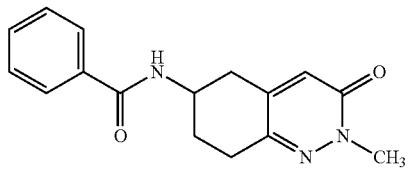 [SMILES: Cn1nc2c(cc1=O)CC(NC(=O)c1ccccc1)CC2]

N-(2-methyl-3-oxo-5,6,7,8-tetrahydrocinnolin-6-yl)benzamide (16)

To a 40 mL vial was added IV (40 mg, 0.21 mmol) and anhydrous THF (1 mL) under $N_2$ atmosphere. The resulting solution was then treated with Hunig's base (120 μL; 6.73 mmol, 3 eq.) and cooled to 0° C. After 10 min, the reaction mixture was treated with benzoyl chloride (38 mg, 0.027 mmol, 1.2 equiv.) dropwise under $N_2$ atm. Upon completion of the addition, the reaction mixture was allowed to warm to RT. The reaction mixture was diluted with saturated aqueous sodium chloride and extracted with methylene chloride (2×5 mL). The combined extracts were dried ($Na_2SO_4$) then concentrated in vacuo. The product was purified by reverse phase chromatography (55 g C18 AQ, 0-100% acetonitrile/water with 0.1% formic acid), to afford after lyophilization N-(2-methyl-3-oxo-5,6,7,8-tetrahydrocinnolin-6-yl)benzamide as a white solid (38 mg, 65%). $^1$H NMR (300 MHz, CD3OD): δ 1.92 (m, 1H), 2.19 (m, 1H), 2.86 (set of m, 3H), 3.17 (dd, J=17, 5.4 Hz, 1H), 3.73 (s, 3H), 4.31 (m, 1H), 6.74 (s, 1H), 7.50 (m, 3H, aromatics), 7.80 (dd, J=2.7, 8 Hz, 2H, aromatics); LC/MS: RT 3.30 min: m/z 284.2 (M+1).

Scheme 2: Carboxylic Acid Method: Compound 5

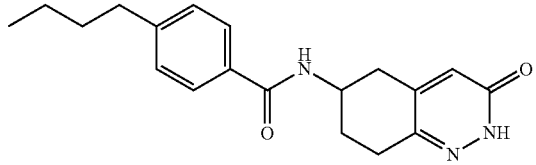 [SMILES: CCCCc1ccc(C(=O)NC2CCc3n[nH]c(=O)cc3C2)cc1]

4-n-butyl-N-(3-oxo-5,6,7,8-tetrahydrocinnolin-6-yl)benzamide (5)

A solution of n-4-butylbenzoic acid (45 mg, 0.25 mmol, 1.5 equiv.) in DMF (1 mL) was successively treated with diisopropylethylamine (90 μL, 0.52 mmol, 3.1 equiv) and HATU (89 mg, 0.23 mmol, 1.4 equiv). After 20 min, the reaction mixture was treated with 7-amino-5,6,7,8-tetrahydro-2H-cinnolin-3-one dihydrochloride, I (40 mg, 0.167 mmol) and left stirring overnight. The mixture was concentrated in vacuo and the residue was purified by reverse phase chromatography (55 g C18 AQ, 0-100% acetonitrile/water with 0.1% formic acid), to afford after lyophilization 4-butyl-N-(3-hydroxy-5,6,7,8-tetrahydrocinnolin-6-yl)benzamide (5) as an off-white solid (16 mg, 29%). $^1$H NMR (300 MHz, DMSO-d6): δ 0.87 (t, J=7 Hz, 3H), 1.28 (m, 2H), 1.53 (m, 2H), 1.7~2.1 (m, 2H), 2.5~2.75 (set of m, 5H), 3.00 (dd, J=17, 5.1 Hz, 1H), 4.15 (m, 1H), 6.60 (s, 1H), 7.26 (A of ABq, J=8 Hz, 2H), 7.76 (B of ABq, 2H, J=8 Hz, 2H), 8.40 (br d, J=7.2 Hz, NH); LC/MS: RT 3.29 min: m/z 326.2 (M+1).

Scheme 3: Synthesis of 4-isopropyl-N-(4-oxocyclohexyl)benzamide

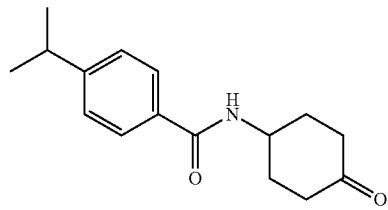 [SMILES: CC(C)c1ccc(C(=O)NC2CCC(=O)CC2)cc1]

A solution of 4-aminocyclohexan-1-one (2.1 g, 18.5 mmol) in DCM (75 mL) was cooled to 0° C. and then treated with triethylamine (2.8 g, 55.5 mmol, 3 equiv.) and dropwise 4-isopropylbenzoyl chloride (4.0 g, 22.2 mmol, 1.2 equiv.). After stirring for 1 h, the reaction was permitted to warm to room temperature. After stirring overnight, LC/MS analysis showed clean conversion to the desired product. The reaction mixture was poured onto satd. NaCl (200 mL) and extracted with ethyl acetate (3×150 mL). The combined organic extracts were dried ($Na_2SO_4$) and the solvent removed in vacuo. The residual solid was purified by flash chromatography (40 g silica, 0-100% ethyl acetate/hexanes) to afford 4-isopropyl-N-(4-oxocyclohexyl)benzamide (2.8 g, 60% yield) as an off-white solid.

4-isopropyl-N-(3-oxo-2-(2,2,2-trifluoroethyl)-2,3,5,6,7,8-hexahydrocinnolin-6-yl)benzamide, 57

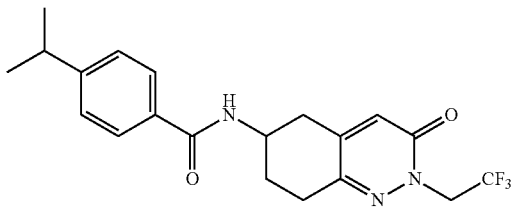 [SMILES: CC(C)c1ccc(C(=O)NC2CCc3nn(CC(F)(F)F)c(=O)cc3C2)cc1]

A solution of glyoxylic acid (22 mg, 0.31 mmol, 1.0 equiv.) in anhydrous ethanol (1 mL) was cooled to 0° C. morpholine (53 mL, 0.62 mmol, 2.0 equiv.) was added dropwise. After 1 hour the solution turned a faint yellow color and the reaction mixture was treated with 4-isopropyl-N-(4-oxocyclohexyl)benzamide (79 mg, 0.31 mmol) and left to slowly warm to room temperature. After stirring overnight, the reaction mixture was treated with (2,2,2-trifluoroethyl)hydrazine (39 mg, 0.34 mmol, 1.1 equiv.). LC/MS analysis showed an inseparable mixture of desired product mixed with the morpholine adduct. The product mixture was purified by reverse phase HPLC (C18, 0-80% water/acetonitrile w/0.1% formic acid). The combined freeze-dried fractions were then subjected to a solution of 50% TFA in dichloromethane (1.2 mL) and let stir at room temperature for 2.5 h. LC/MS shows complete conversion to the product. The solvent was removed in vacuo and the residual solid purified by reverse phase HPLC (C18, 3-80% water/acetonitrile w/0.1% formic acid) to afford 4-isopropyl-N-(3-oxo-2-(2,2,2-trifluoroethyl)-2,3,5,6,7,8-hexahydrocinnolin-6-yl)benzamide, 57 (52 mg, 42% yield) as an off-white solid. $^1$H NMR (CDCl$_3$, 400 MHz) δ 1.26 (d, 6H), 1.89 (set of m, 1H), 2.28 (m, 1H), 2.70 (two dd, J=1, 4, 8 Hz, 1H), 2.8~3.0 (set of m, 2H+1H), 3.25 (two d, J=4, 16 Hz, 1H), 4.40 (m, 1H), 4.75 (two m, 2H), 6.02 (d, J=8 Hz, 1H, NH), 6.72 (s, 1H), 7.30 (A of ABq, J=8 Hz, 2H), 7.68 (B of ABq, J=8 Hz, 2H); LC/MS (C$_{20}$H$_{22}$N$_3$O$_2$): Rt 5.40 min: m/z 394.10 (M+1); HPLC: RT 4.98 min, 99%

Scheme 4: Synthesis of 4-isopropyl-N-(3-oxo-2-((tetrahydro-2H-pyran-4-yl)methyl)-2,3,5,6,7,8-hexahydrocinnolin-6-yl)benzamide, 52

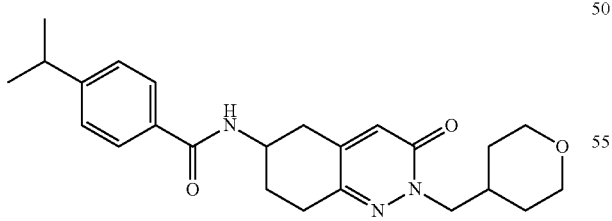

A solution of 4-isopropyl-N-(3-oxo-2,3,5,6,7,8-hexahydrocinnolin-6-yl) benzamide (90 mg, 0.29 mmol) in DMF (1 mL) was successively subjected to cesium carbonate (140 mg, 0.43 mmol, 1.5 equiv.) and 4-(bromomethyl)tetrahydro-2H-pyran (62 mg, 0.35 mmol, 1.2 equiv.). After stirring overnight, LC/MS showed clean conversion to the desired product. The reaction mixture was purified reverse phase by RP-HPLC (C18, 3-80% water/acetonitrile w/0.1% formic acid) to afford 4-isopropyl-N-(3-oxo-2-((tetrahydro-2H-pyran-4-yl)methyl)-2,3,5,6,7,8-hexahydrocinnolin-6-yl)benzamide, 52 (70 mg, 58% yield) as an off-white solid. $^1$H NMR (CDCl$_3$, 400 MHz) d 1.27 (d, 6H), 1.45 (m, 2H), 1.5~1.6 (set of m, overlapped 2H), 1.90 (m, 1H), 2.25 (m, 1H+1H), 2.67 (dd, 1H), 2.8~3.0 (set of m, 1H+2H), 3.20 (d of d, 1H), 3.34 (t, 2H), 3.96 (d, 2H), 4.06 (quintet, 2H), 4.42 (m, 1H), 6.04 (br, 1H, NH), 6.67 (s, 1H), 7.30 (A of ABq, J=8 Hz, 2H), 7.69 (B of ABq, J=8 Hz, 2H); LC/MS (C$_{24}$H$_{31}$N$_3$O$_3$): Rt 5.13 min: m/z 410.35 (M+1); HPLC: RT 4.58 min, >99%.

The following compounds were synthesized using the general methods described above.

Compound 1

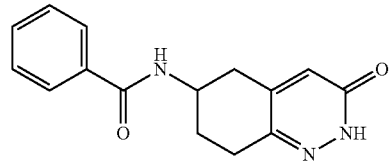 [SMILES: O=C(NC1CCc2n[nH]c(=O)cc2C1)c1ccccc1]

$^1$H NMR (300 MHz, DMSO-d6): δ 1.90 (m, 1H), 2.10 (m, 1H), 2.70 (m, 3H), 3.00 (dd, J=5.4 Hz, 17 Hz, 1H), 4.21 (m, 1H), 6.6 (s, 1H), 7.50 (m, 3H, aromatics), 7.80 (dd, 2.7, 8 Hz, 2H, aromatics), 8.5 (brd, 1H, NH): LC/MS (C$_{15}$H$_{15}$N$_3$O$_2$): RT 1.0 min C$_{16}$H$_{13}$N$_3$O$_{33}$: m/z 270.2 (M+1).

Compound 2

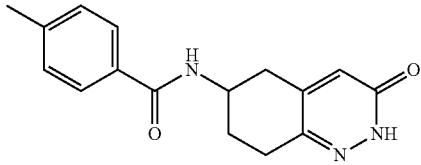 [SMILES: Cc1ccc(C(=O)NC2CCc3n[nH]c(=O)cc3C2)cc1]

$^1$H NMR (300 MHz, DMSO-d6): δ 1.95 (m, 1H), 2.25 (m, 1H), 2.3 (s, 3H), 2.75 (m, 3H), 3.00 (dd, J=17, 5.4 Hz, 1H), 4.20 (m, 1H), 6.60 (s, 1H), 7.25 (A of ABq, J=8 Hz, 2H), 7.75 (B of ABq, 2H, J=8 Hz, 2H), 8.40 (br, 1H, NH): LC/MS (C$_{16}$H$_{17}$N$_3$O$_2$). RT 1.57 min: m/z 284.2 (M+1).

Compound 3

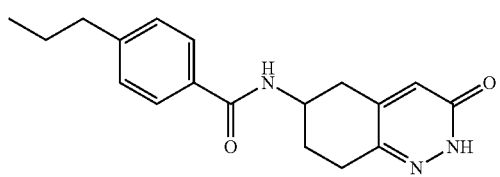 [SMILES: CCCc1ccc(C(=O)NC2CCc3n[nH]c(=O)cc3C2)cc1]

$^1$H NMR (300 MHz, DMSO-d6): δ 0.86 (t, J=7.5 Hz, 3H), 1.58 (q, J=7.2 Hz, 2H), 1.8~2.0 (set of m, 4H), 2.8~3.0 (m, 2H), 4.1 (m, 1H), 6.20 (br, 1H), 7.25 (A of ABq, J=8.1 Hz, 2H), 7.62 (B of ABq, J=8.1 Hz, 2H), 8.38 (brd, 1H, J=8.1 Hz, NH) LC/MS (C$_{18}$H$_{21}$N$_3$O$_2$): RT 2.88 min: m/z 312.3 (M+1).

Compound 4

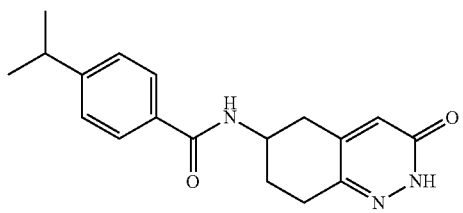

¹H NMR (300 MHz, DMSO-d6): δ 0.86 (t, J=7.5 Hz, 3H), 1.58 (q, J=7.2 Hz, 2H), 1.8~2.0 (set of m, 4H), 2.8~3.0 (m, 2H), 4.1 (m, 1H), 6.20 (br, 1H), 7.25 (A of ABq, J=8.1 Hz, 2H), 7.62 (B of ABq, J=8.1 Hz, 2H), 8.38 (brd, 1H, J=8.1 Hz, NH) LC/MS (C₁₈H₂₁N₃O₂): RT 2.63 min: in/z 312.3 (M+1).

Compound 6

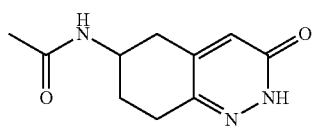

¹H NMR (300 MHz, CD₃OD): δ 1.80 (m, 1H), 1.95 (s, 3H), 2.08 (br, 1H), 2.6~2.9 (set of m, 3H), 3.05 (dd, J=17, 5.4 Hz, 1H), 4.10 (m, 1H), 6.70 (s, 1H); LC/MS (C₁₀H₁₃N₃O₂): RT 0.94 min: m/z 208.2 (M+1)

Compound 7

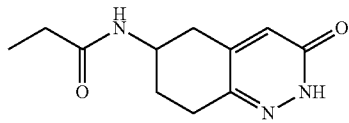 [SMILES: CCC(=O)NC1CCc2n[nH]c(=O)cc2C1]

¹H NMR (300 MHz, CD₃OD): δ 1.25 (t, J=7.5 Hz, 3H), 1.80 (m, 1H), 2.08 (br, 1H), 2.20 (q, 2H), 2.6~2.9 (set of m, 3H), 3.05 (dd, J=17, 5.4 Hz, 1H), 4.10 (m, 1H), 6.70 (s, 1H): LC/MS (C₁₁H₁₅N₃O₂): RT 0.88 min: m/z 222.1 (M+1).

Compound 8

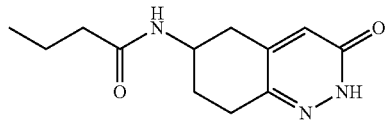 [SMILES: CCCC(=O)NC1CCc2n[nH]c(=O)cc2C1]

¹H NMR (300 MHz, CD₃OD): δ 0.90 (m, 3H), 1.65 (m, 2H), 1.70 (m, 1H), 2.08 (br, 1H), 2.20 (m, 2H), 2.6~2.9 (set of m, 3H), 3.05 (dd, J=17, 5.4 Hz, 1H), 4.10 (m, 1H), 6.70 (s, 1H): LC/MS (C₁₂H₁₇N₃O₂): RT 0.97 min: m/z 236.2 (M+1)

Compound 9

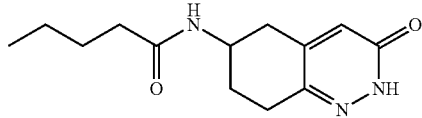 [SMILES: CCCCC(=O)NC1CCc2n[nH]c(=O)cc2C1]

¹H NMR (300 MHz, CD₃OD): δ 0.95 (t, J=7.5 Hz, 3H), 1.35 (m, 2H), 1.60 (m, 2H), 1.80 (m, 1H), 2.08 (m, 1H), 2.20 (t, 2H), 2.6-2.9 (set of m, 3H), 3.05 (dd, J=17, 5.4 Hz, 1H), 4.10 (m, 1H), 6.70 (s, 1H); LC/MS (C₁₃H₁₉N₃O₂): RT 1.02 min: m/z 250.2 (M+1).

Compound 10

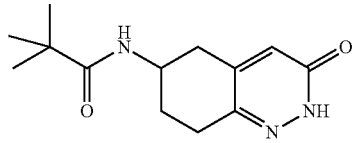 [SMILES: CC(C)(C)C(=O)NC1CCc2n[nH]c(=O)cc2C1]

¹H NMR (300 MHz, CD₃OD): δ 1.28 (s, 9H), 1.80 (m, 1H), 2.05 (br, 1H), 2.6~2.9 (set of m, 3H), 3.05 (dd, J=17, 5.4 Hz, 1H), 4.10 (m, 1H), 6.70 (s, 1H): LC/MS (C₁₃H₁₉N₃O₂): RT 1.13 min: m/z 250.3 (M+1).

Compound 11

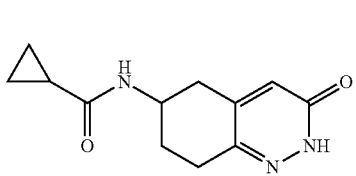 [SMILES: O=C(NC1CCc2n[nH]c(=O)cc2C1)C1CC1]

¹H NMR (300 MHz, DMSO-d6): δ 0.65 (two d, J=4.5 Hz, 4H), 1.53 (m, 1H), 1.72 (m, 1H), 1.92 (m, 1H), 2.6~2.9 (set of m, 3H), 2.90 (dd, J=17, 5.4 Hz, 1H), 4.94 (m, 1H), 6.60 (s, 1H), 8.15 (d, J=7.2 Hz, 1H): LC/MS (C₁₂H₁₅N₃O₂): RT 2.02 min: m/z 234.2 (M+1).

Compound 12

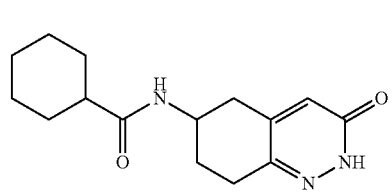 [SMILES: O=C(NC1CCc2n[nH]c(=O)cc2C1)C1CCCCC1]

¹H NMR (300 MHz, DMSO-d6): δ 1.0~1.5 (set of m, 5H), 1.66 (set of m, 5H), 1.86 (m, 1H), 2.06 (m, 1H), 2.68 (set of m, overlapped with solvent, 3H+1H), 2.87 (dd, J=17, 5.4 Hz, 1H), 3.89 (m, 1H), 6.59 (s, 1H), 7.79 (d, J=7 Hz, 1H, NH): LC/MS (C₁₂H₁₅N₃O₂): RT 1.15 min: m/z 276.2 (M+1).

Compound 13

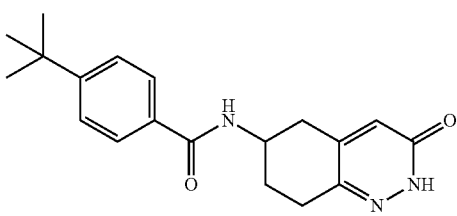 [SMILES: CC(C)(C)c1ccc(C(=O)NC2CCc3n[nH]c(=O)cc3C2)cc1]

¹H NMR (300 MHz, DMSO-d6): δ 1.25 (s, 9H), 1.85 (m, 1H), 2.05 (m, 1H), 2.75 (set of m, 3H), 3.00 (dd, J=17, 5.4 Hz, 1H), 4.20 (m, 1H), 6.60 (s, 1H), 7.45 (A of ABq, J=8 Hz, 2H), 7.80 (B of ABq, 2H, J=8 Hz, 2H), 8.40 (brd, 1H, NH); LC/MS (C₁₉H₂₃N₃O₂): RT 3.55 min: m/z 326.2 (M+1).

Compound 14

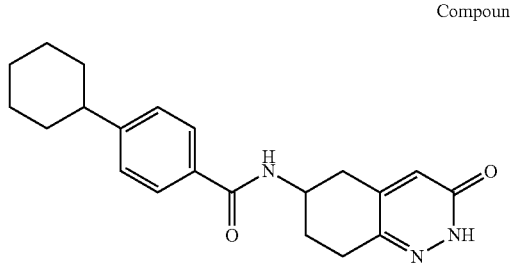

¹H NMR (300 DMSO-d6): δ 1.0~1.5 (set of m, 5H), 1.66 (set of m, 5H), 1.86 (m, 1H), 2.06 (m, 1H), 2.68 (set of m, overlapped, 3H+1H), 3.00 (dd, J=17, 5.4 Hz, 1H), 4.15 (m, 1H), 6.62 (s, 1H), 7.28 (A of ABq, J=8 Hz, 2H), 7.74 (B of ABq, 2H, J=8 Hz, 2H), 8.33 (br d, J=7.2 Hz, NH); LC/MS ($C_{21}H_{25}O_2$): RT 3.23 min: m/z 352.2 (M+1).

Compound 15

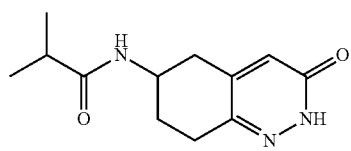 [SMILES: CC(C)C(=O)NC1CCc2n[nH]c(=O)cc2C1]

¹H NMR (300 MHz, $CD_3OD$): δ 1.11 (d, J=7 Hz, 6H), 1.80 (m, 1H), 2.10 (m, 1H), 2.44 (m, J=7.0 Hz, 1H), 2.6~2.9 (set of m, 3H, 3.04 (dd, J=17, 3 Hz, 1H), 4.06 (m, 1H), 6.80 (s, 1H)): IC/MS ($C_{12}H_{17}N_3O_2$): RT 0.94 min: m/z 236.1 (M+1).

Compound 17

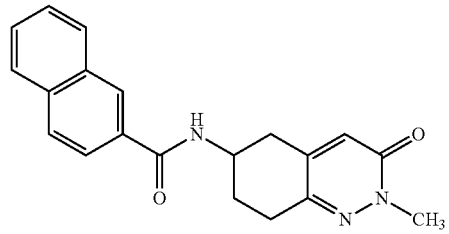 [SMILES: Cn1nc2c(cc1=O)CC(NC(=O)c1ccc3ccccc3c1)CC2]

¹H NMR (300 MHz, $CDCl_3$): δ 1.95 (m, 1H), 2.25 (m, 1H), 2.70 (dd, J=17, 7.5 Hz, 1H), 2.90 (m, 2H), 3.18 (dd, J=17, 5.4 Hz, 1H), 3.70 (s, 3H), 4.45 (m, 1H), 6.55 (s, 1H), 6.80 (brd, 1H, NH), 7.50 (m, 3H, aromatics), 7.80 (set of m, 4H, aromatics), 8.60 (s, 1H): LC/MS ($C_{20}H_{19}N_3O_2$): RT 3.65 min: m/z 334.4 (M+1)

Compound 18

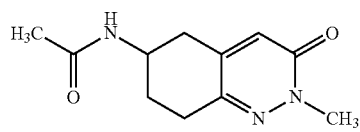

¹H NMR (300 MHz, CDCl3): δ 1.90 (m, 1H), 2.0 (s, 3H), 2.10 (m, 1H), 2.60 (dd, J=17 Hz, 1H), 2.80 (m, 2H), 3.10 (dd, J=17, 5.4 Hz, 1H), 3.75 (s, 3H), 4.20 (m, 1H), 5.70 (brd, 1H, NH), 6.60 (s, 1H): LC/MS ($C_{11}H_{15}N_3O_2$): RT 3.0 min: m/z 222.0 (M+1)

Compound 19

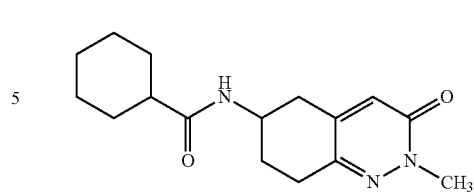

¹H NMR (300 MHz, $CDCl_3$): δ 1.2~2.0 (set of m, 11H), 2.15 (m, 2H), 2.60 (dd, J=17, 7.5 Hz, 1H), 2.80 (set of m, 2H), 3.10 (dd, J=17, 5.4 Hz, 1H), 3.80 (s, 3H), 4.20 (m, 1H), 5.60 (brd, NH), 6.60 (s, 1H): LC/MS ($C_{16}H_{23}N_3O_2$): RT 3.48 min: m/z 290.1 (M+1)

Compound 20

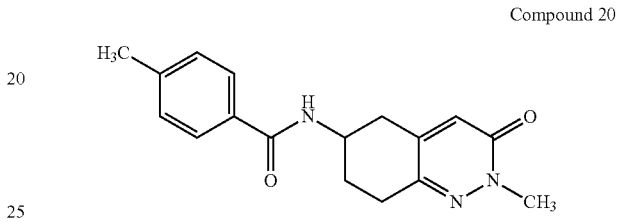

¹H NMR (300 MHz, $CDCl_3$): δ 1.95 (m, 1H), 2.25 (m, 1H), 2.42 (s, 3H), 2.75 (dd, J=17, 7.5 Hz, 1H), 2.90 (m, 2H), 3.20 (dd, J=17, 5.4 Hz, 1H), 3.80 (s, 3H), 4.45 (m, 1H), 6.20 (br, 1H), 6.70 (s, 1H), 7.30 (A of ABq, J=8 Hz, 2H), 7.70 (B of ABq, J=8 Hz, 2H): LC/MS ($C_{16}H_{17}N_3O_2$): RT 3.45 min: m/z 298.1 (M+1)

Compound 21

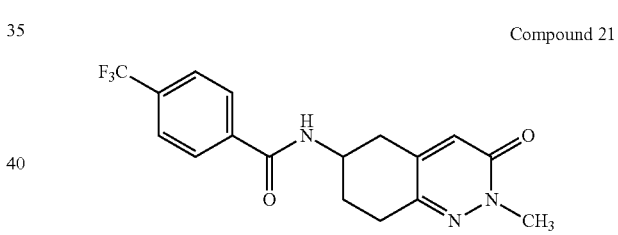

¹H NMR (300 MHz, $CDCl_3$): δ 2.00 (m, 1H), 2.21 (m, 1H), 2.72 (dd, J=17, 7.5 Hz, 1H), 2.91 (set of m, 2H) 3.20 (dd, J=17, 5.4 Hz, 1H), 3.72 (s, 3H), 4.48 (m, 1H), 6.61 (s, 1H), 7.70 (A of ABq, J=8 Hz, 2H), 7.90 (B of ABq, J=8 Hz, 2H); LC/MS ($C_{17}H_{16}F_3N_3O_2$): RT 3.85 min: m/z 352.3 (M+1)

Compound 22

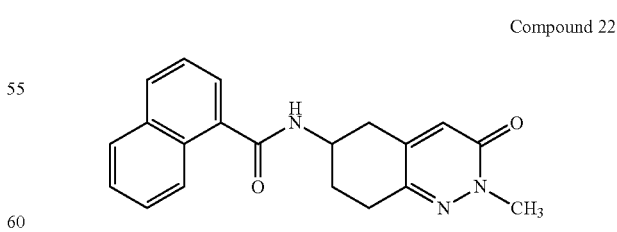

¹H NMR (300 MHz, $CDCl_3$): δ 1.95 (m, 1H), 2.35 (m, 1H), 2.75 (dd, J=17 Hz, 1H), 2.90 (m, 2H), 3.20 (dd, J=17, 5.4 Hz, 1H), 3.70 (s, 3H), 4.45 (m, 1H), 6.25 (brd, 1H, NH), 6.60 (s, 1H), 7.4~7.6 (set of m, 4H, aromatics), 7.90 (set of m, 3H, aromatics), 8.60 (s, 1H): LC/MS ($C_{20}H_{19}N_3O_2$): RT 3.60 min: m/z 334.4 (M+1)

Compound 23

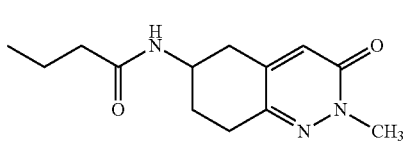 [SMILES: CCCC(=O)NC1CCc2nn(C)c(=O)cc2C1]

¹H NMR (300 MHz, CDCl₃): δ 1.0 (t, J=7.5 Hz, 3H), 1.8~2.0 (set of m, 2H+1H), 2.20 (set of m, 2H+1H), 2.55 (dd, J=17 Hz, 1H), 2.60 (set of m, 2H), 3.10 (dd, J=17, 5.4 Hz, 1H), 3.75 (s, 3H), 4.20 (m, 1H), 5.70 (brd, 1H, NH), 6.60 (s, 1H); LC/MS ($C_{11}H_{15}N_3O_2$): RT 3.0 min: m/z 250.1 (M+1)

Compound 24

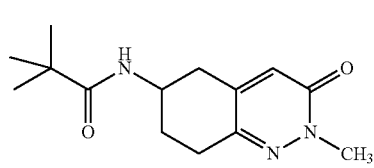

¹H NMR (300 MHz, CDCl₃): δ 1.20 (s, 9H, t-Bu), 1.78 (m, 1H), 2.15 (m, 1H), 2.55 (dd, J=17 Hz, 1H), 2.80 (m, 2H), 3.10 (dd, J=17, 5.4 Hz, 1H), 3.75 (s, 3H), 4.15 (m, 1H), 5.60 (brd, 1H, NH), 6.60 (s, 1H): LC/MS ($C_{14}H_{21}N_3O_2$): RT 3.18 min: m/z 264.1 (M+1)

Compound 25

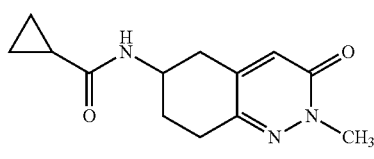 [SMILES: Cn1nc2c(cc1=O)CC(NC(=O)C1CC1)CC2]

¹H NMR (300 MHz, CDCl₃): δ 0.75 (m, J=7.5 Hz, 2H), 0.98 (m, 2H), 1.40 (m, 1H), 1.8~2.2 (set of m, 2H), 2.60 (dd, J=17 Hz, 1H), 2.80 (set of m, 2H), 3.05 (dd, J=17, 5.4 Hz, 1H), 3.70 (s, 3H), 4.30 (m, 1H), 6.30 (brd, 1H, NH), 6.60 (s, 1H): LC/MS ($C_{13}H_{17}N_3O_2$): RT 2.85 min: m/z 248.2 (M+1)

Compound 26 (Compound II Scheme 1)

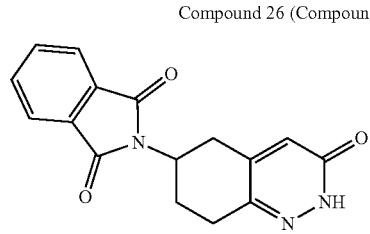

¹H NMR (300 MHz, CDCl₃): δ 2.10 (m, 1H), 2.6~3.1 (set of m, 4H), 3.60 (dd, J=17, 5.4 Hz, 1H), 4.60 (m, 1H), 6.75 (s, 1H), 7.75 and 7.85 (two m, 4H): LC/MS ($C_{16}H_{13}N_3O_3$): RT 3.45 min: m/z 296.1 (M+1)

Compound 27 (Compound III Scheme 1)

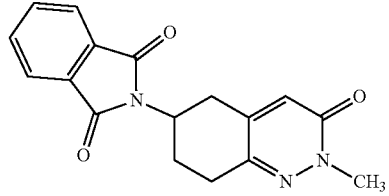

¹H NMR (300 MHz, CDCl₃): δ 2.05 (m, 1H), 2.6~3.0 (set of m, 4H), 3.55 (dd, J=17, 5.4 Hz, 1H), 3.75 (s, 3H), 4.50 (m, 1H), 6.65 (s, 1H), 7.75 and 7.85 (two d, 4H). ¹³C NMR (300 MHz, CDCl₃): δ 26.7, 28.9, 31.3, 40.0, 46.1, 123.6, 127.0, 131.9, 134.5, 141.7, 143.7, 160.5, 168.3. LC/MS ($C_{16}H_{13}N_3O_3$): RT 3.62 min: m/z 310.1 (M+1)

Compound 28

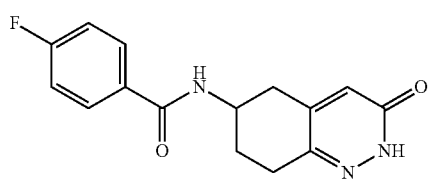 [SMILES: O=C(NC1CCc2n[nH]c(=O)cc2C1)c1ccc(F)cc1]

¹H NMR (300 MHz, DMSO-d6): δ 1.82 (m, 1H), 2.05 (m, 1H), 2.70 (set of m, 3H), 3.00 (dd, J=17, 5 Hz, 1H), 4.18 (m, 1H), 6.62 (s, 1H), 7.30 (dd, A of ABq, J=9, 2 Hz, 2H), 7.90 (two d, B of ABq, J=9 Hz, 2H), 8.48 (brd, 1H, NH). LC/MS ($C_{15}H_{14}FN_3O_2$): RT 3.47 min: m/z 288.3 (M+1). HPLC: RT 3.07 min, 96%

Compound 29

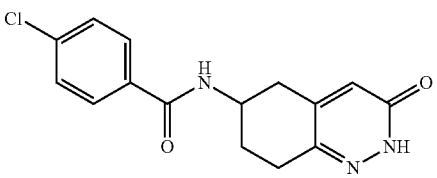 [SMILES: O=C(NC1CCc2n[nH]c(=O)cc2C1)c1ccc(Cl)cc1]

¹H NMR (300 MHz, DMSO-d6): δ 1.83 (m, 1H), 2.00 (m, 1H), 2.72 (set of m, 3H), 3.00 (dd, J=17, 5. Hz, 1H), 4.17 (m, 1H), 6.62 (s, 1H), 7.52 (A of ABq, J=8.4 Hz, 2H), 7.85 (B of ABq, J=8.4 Hz, 2H), 8.53 (brd, 1H, NH). LC/MS ($C_{15}H_{14}ClN_3O_2$): RT 3.70 min, m/z 304.2 (M+1). HPLC: RT 3.38 min, 97%

Compound 30

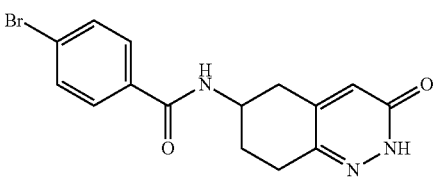

¹H NMR (300 MHz, CD₃OD): δ 1.93 (m, 1H), 2.20 (m, 1H), 2.86 (set of m, 3H), 3.18 (dd, J=17, 5 Hz, 1H), 4.30 (m, 1H), 6.73 (s, 1H), 7.61 (A of ABq, J=8.7 Hz, 2H), 7.73 (B of ABq, J=8.4 Hz, 2H), 7.83 (s, 1H); LC/MS ($C_{15}H_{14}BrN_3O_2$): RT 3.78 min, m/z 350.8 (M+1). HPLC: RT 3.48 min, 97%

Compound 31

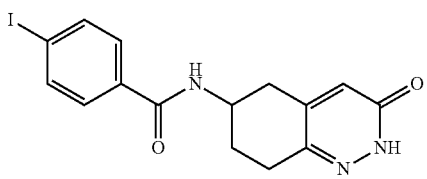 [SMILES: O=C(NC1CCc2n[nH]c(=O)cc2C1)c1ccc(I)cc1]

¹H NMR (300 MHz, DMSO-d6): δ 1.82 (m, 1H), 1.99 (m, 1H), 2.70 (set of m, 3H), 3.00 (dd, J=17, 5 Hz, 1H), 4.16 (m, 1H), 6.62 (s, 1H), 7.62 (A of ABq, J=8.7 Hz, 2H), 7.83 (B of ABq, J=8.4 Hz, 2H), 8.53 (d, J=10.5 Hz, 1H); LC/MS ($C_{15}H_{14}IN_3O_2$): Rt 4.00 min, m/z 396.2 (M+1). HPLC: RT 3.66 min, 99%.

Compound 32

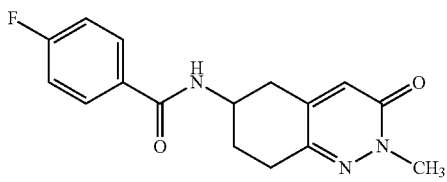

¹H NMR (300 MHz, CDCl₃): δ 1.95 (m, 1H), 2.20 (m, 1H), 2.70 (dd, J=17 Hz, 1H) 2.90 (set of m, 2H), 3.15 (dd, J=17, 5 Hz, 1H), 3.71 (s, 3H), 4.44 (m, 1H), 6.40 (br, NH), 6.61 (s, 1H), 7.10 (dd, A of ABq, J=9 Hz, 2H), 7.81 (two d, B of ABq, J=9 Hz, 2H); LC/MS ($C_{16}H_{16}FN_3O_2$): RT 3.11 min, m/z 302.1 (M+1). HPLC: RT 3.50 min, 99%.

Compound 33

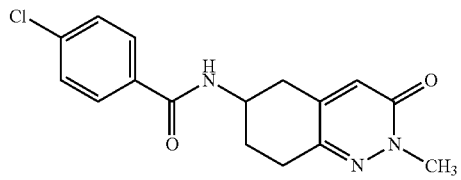

¹H NMR (300 MHz, CDCl₃): δ 1.97 (m, 1H), 2.21 (m, 1H), 2.68 (dd, J=17 Hz, 1H) 2.88 (set of m, 2H), 3.18 (dd, J=17, 5 Hz, 1H), 3.73 (s, 3H), 4.44 (m, 1H), 6.42 (brd, NH, 1H), 6.62 (s, 1H), 7.56 (d, A of ABq, J=9 Hz, 2H), 7.66 (d, B of ABq, J=9 Hz, 2H); LC/MS ($C_{16}H_{16}C_1N_3O_2$): RT 3.77 min, m/z 318.1 (M+1). HPLC: RT 3.71 min, >97%.

Compound 34

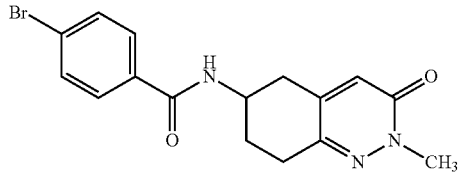 [SMILES: Cn1nc2c(cc1=O)CC(NC(=O)c1ccc(Cl)cc1)CC2]

¹H NMR (300 MHz, CDCl₃): δ 1.94 (m, 1H), 2.17 (m, 1H), 2.70 (dd, J=17 Hz, 1H) 2.88 (set of m, 2H), 3.13 (dd, J=17, 5 Hz, 1H), 3.69 (s, 3H), 4.44 (m, 1H), 6.64 (s, 1H), 6.79 (brd, 1H, NH), 7.37 (d, A of ABq, J=9 Hz, 2H), 7.76 (d, B of ABq, J=9 Hz, 2H); LC/MS ($C_{16}H_{16}BrN_3O_2$): RT 4.10 min, m/z 363.2 (M+1). HPLC: RT 3.94 min, >99%.

Compound 35

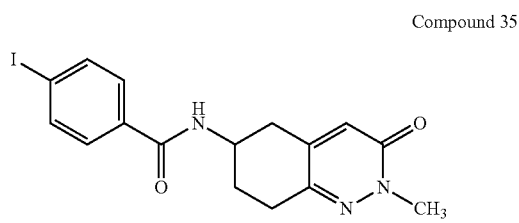

¹H NMR (300 MHz, CDCl₃): δ 1.93 (m, 1H), 2.22 (m, 1H), 2.68 (dd, J=17, 9 Hz, 1H) 2.88 (set of m, 2H), 3.18 (dd, J=17, 5 Hz, 1H), 3.73 (s, 3H), 4.41 (m, 1H), 6.29 (brd, 1H, NH), 6.63 (s, 1H), 7.49 (d, A of ABq, J=9 Hz, 2H), 7.78 (d, B of ABq, J=9 Hz, 2H); LC/MS ($C_{16}H_{16}IN_3O_2$): RT 4.17 min, m/z 410.2 (M+1). HPLC: >99.

Compound 36

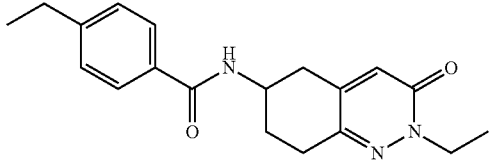 [SMILES: CCc1ccc(C(=O)NC2CCc3nn(CC)c(=O)cc3C2)cc1]

¹H NMR (300 MHz, CDCl₃): δ 1.18 (t, J=7.7 Hz, 3H), 1.35 (t, J=7.7 Hz, 3H), 1.85 (m, 1H), 2.20 (m, 1H), 2.60 (set of m, J=7.8 Hz, 2H+1H), 2.86 (set of m, 2H), 3.15 (dd, J=17, 5 Hz, 1H), 4.15 (q, 2H), 4.35 (m, 1H), 6.05 (m, 1H), 6.60 (s, 1H), 7.21 (A of ABq, J=8.7 Hz, 2H), 7.60 (B of ABq, J=8.4 Hz, 2H), 7.95 (d, NH, 1H): LC/MS ($C_{18}H_{23}N_3O_2$): RT 4.17 min, m/z 326.3 (M+1). HPLC: 99%

Compound 37

¹H NMR (300 MHz, CDCl₃): δ 0.94 (t, J=7.5 Hz, 3H), 1.24 (t, J=7.5 Hz, 3H), 1.80 (q, J=7.5 Hz, 2H), 1.90 (m, 1H), 2.23 (m, 1H), 2.70 (q and m, J=7.5 Hz, 2H+1H), 2.90 (m, 2H), 3.19 (dd, J=17, 5 Hz, 1H), 4.05 (two t, J=7.5 Hz, 2H), 4.40 (m, 1H), 6.31 (br, NH), 6.63 (s, 1H), 7.25 (A of ABq, J=7.8 Hz, 2H), 7.69 (B of ABq, J=7.8 Hz, 2H); LC/MS (C20H25N3O2): RT 4.90 min: m/z 340.1 (M+1); HPLC: RT 4.36 min, 97%

Compound 38

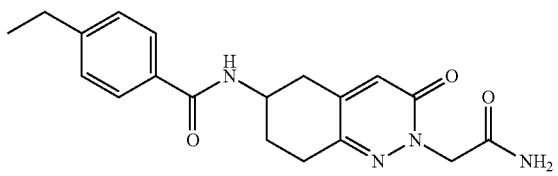 [SMILES: CCc1ccc(C(=O)NC2CCc3nn(CC(N)=O)c(=O)cc3C2)cc1]

¹H NMR (CD₃OD, 400 MHz) δ 1.27 (t, 3H), 1.95 (m, 1H), 2.20 (m, 1H), 2.70 (q, 2H), 2.8~3.1 (set of m, 2H+1H), 3.15 (d of m, 1H), 4.35 (m, 1H), 4.75 (ABq, overlapped, 2H), 6.77 (s, 1H), 7.31 (A of ABq, J=8 Hz, 2H), 7.76 (B of ABq, J=8 Hz, 2H): LC/MS ($C_{19}H_{22}N_4O_3$): RT 4.38 min: m/z 355.10 (M+1); HPLC: RT 3.38 min, >99%

Compound 39

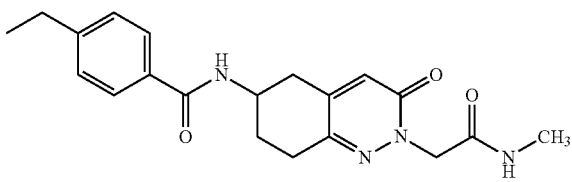 [SMILES: CCc1ccc(C(=O)NC2CCc3nn(CC(=O)NC)c(=O)cc3C2)cc1]

¹H NMR (CD₃OD, 400 MHz) δ 1.27 (t, 3H), 1.95 (m, 1H), 2.25 (m, 1H), 2.70 (q, 2H), 2.77 (s, 3H), 2.8-3.0 (set of m, 2H+1H), 3.15 (d of m, 1H), 4.32 (m, 1H), 4.75 (ABq, 2H), 6.77 (s, 1H), 7.30 (A of ABq, J=8 Hz, 2H), 7.76 (B of ABq, J=8 Hz, 2H); LC/MS ($C_{20}H_{24}N_4O_3$): Rt 4.38 min: m/z 369.09 (M+1); HPLC: RT 3.49 min, >99%

Compound 40

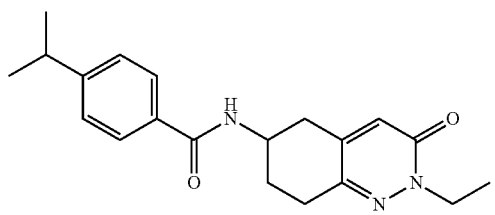 [SMILES: CCn1nc2c(cc1=O)CC(NC(=O)c1ccc(C(C)C)cc1)CC2]

¹H NMR (300 MHz, CDCl₃) δ 1.26 (d, J=7 Hz, 6H), 1.36 (t, J=7.7 Hz, 3H), 1.94 (m, 1H), 2.23 (m, 1H), 2.68 (dd, J=17 Hz, 1H) 2.94 (set of m, 2H), 3.30 (dd, J=17, 5 Hz, 1H), 4.18 (q, J=7.2 Hz, 2H), 4.41 (m, 1H), 6.16 (brd, NH, 1H), 6.75 (s, 1H), 7.27 (d, A of ABq, J=9 Hz, 2H), 7.69 (d, B of ABq, J=9 Hz, 2H). LC/MS ($C_{20}H_{25}N_3O_2$): RT 4.35 min, m/z 340.4 (M+1). HPLC: 93%.

Compound 41

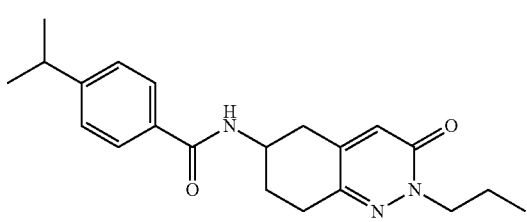

¹H NMR (300 MHz, CDCl₃): δ 0.95 (t, J=7 Hz, 3H), 1.26 (d, J=7 Hz, 6H), 1.80 (m, 2H), 1.94 (m, 1H), 2.23 (m, 1H), 2.70 (dd, J=17 Hz, 1H) 2.95 (set of m, 2H+1H), 3.15 (dd, J=17, 5 Hz, 1H), 4.05 (q, J=7.2 Hz, 2H), 4.40 (m, 1H), 6.16-6.75 (s and m, overlapped 1H+1H), 7.30 (d, A of ABq, J=9 Hz, 2H), 7.70 (d, B of ABq, J=9 Hz, 2H). LC/MS ($C_{21}H_{27}N_3O_2$): RT 4.58 min, m/z 354.4 (M+1). HPLC: 95%.

Compound 42

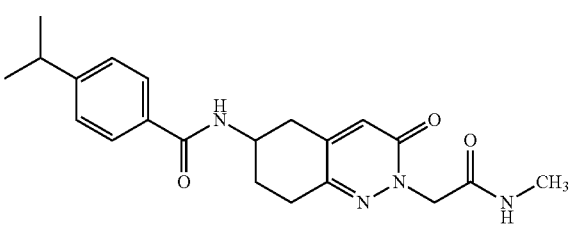 [SMILES: CNC(=O)Cn1nc2c(cc1=O)CC(NC(=O)c1ccc(C(C)C)cc1)CC2]

¹H NMR (CD₃OD, 400 MHz) δ 1.26 (d, 6H), 1.95 (m, 1H), 2.25 (m, 1H), 2.75 (s, overlapped, 3H), 2.8~3.0 (set of m, 1H+1H+2H), 3.18 (d of m, 1H), 4.32 (m, 1H), 4.75 (ABq, 2H), 6.77 (s, 1H), 7.35 (A of ABq, J=8 Hz, 2H), 7.77 (B of ABq, J=8 Hz, 2H); LC/MS ($C_{21}H_{26}N_4O_3$): RT 4.68 min: m/z 383.26 (M+1); HPLC: RT 3.74 min, 99%

Compound 43

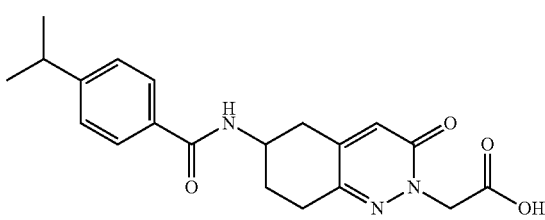 [SMILES: CC(C)c1ccc(C(=O)NC2CCc3nn(CC(=O)O)c(=O)cc3C2)cc1]

¹H NMR (CD₃OD, 400 MHz) δ 1.26 (d, 6H), 1.95 (m, 1H), 2.20 (m, 1H), 2.8~3.0 (set of m, 1H+1H+2H), 3.17 (d of m, 1H), 4.35 (m, 1H), 4.78 (two d, overlapped solvent, 2H), 6.77 (s, 1H), 7.33 (A of ABq, J=8 Hz, 2H), 7.77 (B of ABq, J=8 Hz, 2H); LC/MS ($C_{20}H_{23}N_3O_4$): RT 4.78 min: m/z 370.28 (M+1); HPLC: RT 3.90 min, >99%

Compound 44

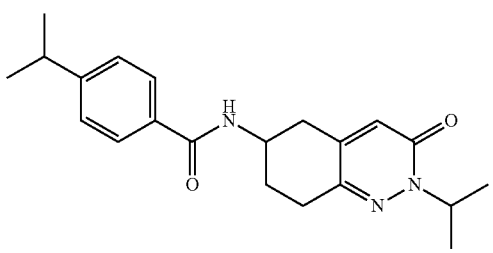 [SMILES: CC(C)c1ccc(C(=O)NC2CCc3nn(C(C)C)c(=O)cc3C2)cc1]

¹H NMR (DMSO-d6, 400 MHz) δ 1.1~1.4 (set of d, 12H), 1.7~2.2 (set of m, 3H, 3H), 2.70 (set of m, 1.5H, 1H), 2.94 (set of m, 1.5H, 2H), 4.17 and 4.07 (two m, 1H), 4.37 (m, 0.5H), 4.88 (m, 0.5H), 5.12 (m, 0.5H, NH?), 6.66 and 6.71 (two s, 1H), 7.33 (dd, A of ABq, 2H), 7.82 (dd, B of ABq, 2H); LC/MS ($C_{21}H_{27}N_3O_2$): RT 5.43 min: m/z 354.09 (M+1); HPLC: RT 4.96 min, >99%

Compound 45

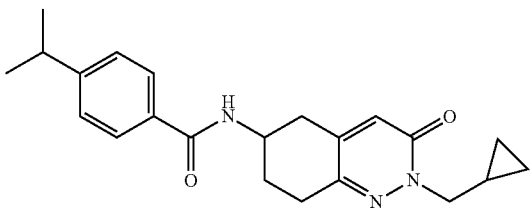

¹H NMR (DMSO-d6, 400 MHz) δ 0.36 (m, 2H), 0.45 (m, 2H), 1.21 (overalpped d and m, 6H+1H), 1.85 (m, 1H), 2.01 (m, 1H), 2.75 (set of m, 2H+1H), 2.93 (m, 1H), 3.00 (two d, 1H), 3.86 (m, 2H), 4.19 (m, 1H), 6.69 (s, 1H), 7.33 (A of ABq, J=12 Hz, 2H), 7.77 (B of ABq, J=8 Hz, 2H), 8.37 (d, 1H, NH); LC/MS ($C_{22}H_{27}N_3O_2$): RT 5.40 min: m/z 366.00 (M+1); HPLC: RT 4.95 min, >99%

Compound 46

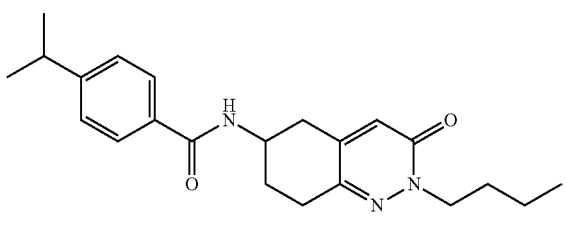

¹H NMR (CDCl₃, 500 MHz) δ 0.97 (t, J=7.5 Hz, 3H), 1.26 (d, J=7.5 Hz, 6H), 1.41 (m, 2H), 1.78 (m, 2H), 1.95 (m, 1H), 2.23 (m, 1H), 2.83 (set of m, 2H), 2.96 (set of m, 2H), 3.16 (two dt, 1H), 4.13 (dt, 2H), 4.32 (m, 1H), 6.73 (s, 1H), 7.34 (A of ABq, 2H), 7.76 (B of ABq, 2H); LC/MS ($C_{22}H_{29}N_3O_2$); RT 4.55 min: m/z 368.29 (M+1); HPLC: RT 5.05 min, 99%

Compound 47

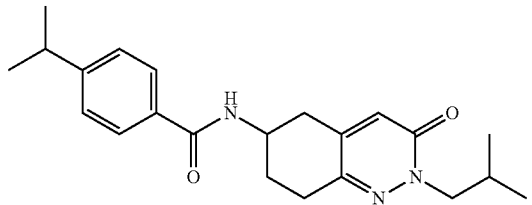

¹H NMR (CDCl₃, 400 MHz) δ 0.95 (d, J=8 Hz, 6H), 1.27 (d J=8 Hz, 6H), 1.90 (m, 1H), 2.28 (m, 1H+1H), 2.70 (two dd, J=1, 4, 8 Hz, 1H), 2.8~3.0 (set of m, 2H+1H), 3.20 (two d, J=4, 16 Hz, 1H), 3.95 (ABq, J=12 Hz, 2H), 4.43 (m 1H), 6.03 (d, 1H, NH), 6.67 (s, 1H), 7.30 (A of ABq, J=8 Hz, 2H), 7.68 (B of ABq, J=8 Hz, 2H); LC/MS ($C_{22}H_{29}N_3O_2$): RT 5.45 min: m/z 397.95 (M+1); HPLC: RT 5.13 min, 99%

Compound 48

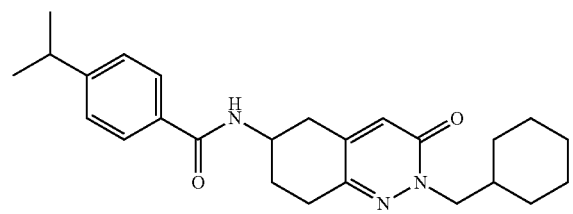

¹H NMR (CDCl₃, 400 MHz) δ 1.27 (d J=8 Hz, 6H), 1.80-1.95 (m, 4H+1H), 2.03 (m, 2H), 2.25 (m, 1H), 2.66 (two dd, J=1, 4, 8 Hz, 1H), 2.8-3.0 (set of m, 2H+1H+1H), 3.20 (two d, J=4, 16 Hz, 1H), 4.18 (ABq, J=12 Hz, 2H), 4.43 (m 1H), 6.03 (d, 1H, NH), 6.65 (s, 1H), 7.30 (A of ABq, J=8 Hz, 2H), 7.68 (B of ABq, J=8 Hz, 2H); LC/MS ($C_{23}H_{29}N_3O_2$): RT 5.67 min: m/z 380.05 (M+1); HPLC: RT 5.20 min, 96%

Compound 49

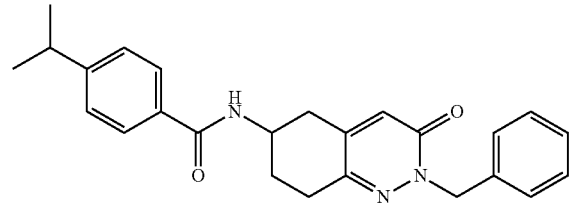

¹H NMR (CDCl₃, 400 MHz) δ 1.06 (m, 1H), 1.27 (overlapped d and m, 6H+1H), 1.4-1.8 (br, 8H), 1.90 (m, 1H), 2.25 (m, 1H), 2.66 (dd, J=1, 12 Hz, 1H), 2.8-3.0 (set of m, 2H+1H), 3.20 (dd, J=16, 4 Hz, 1H), 3.96 (d, J=7.5 Hz, 2H), 4.41 (m, 1H), 6.01 (d, 1H, NH), 6.66 (s, 1H), 7.30 (A of ABq, J=8 Hz, 2H), 7.69 (B of ABq, J=8 Hz, 2H); LC/MS ($C_{25}H_{33}N_3O_2$): RT 6.22 min: m/z 408.22 (M+1); HPLC: RT 5.85 min, >99%

Compound 50

¹H NMR (CD3OD, 400 MHz) δ 1.28 (d, J=8 Hz, 6H), 1.93 (m, 1H), 2.22 (m, 1H), 2.80 (m, 1H+1H), 2.95 (m, overlapped, 2H), 3.15 (dd, 1H), 4.31 (m, 1H), 5.30 (q like dd, J=8 Hz, 2H), 6.75 (s, 1H), 7.2~7.4 (set of m, 7H), 7.76 (B of ABq, J=8 Hz, 2H); LC/MS ($C_{25}H_{27}N_3O_2$): RT 5.67 min: m/z 402.10 (M+1); HPLC: RT 5.10 min, >99%

Compound 51

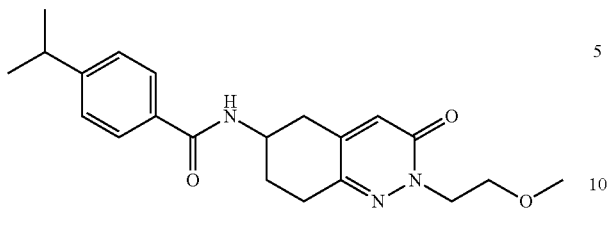

¹H NMR (DMSO-d6, 400 MHz) δ 1.21 (overlapped d and m, 6H), 1.88 (m, 1H), 2.25 (m, 1H), 2.66 (dd, J=1, 8 Hz, 1H), 2.8-3.0 (set of m, 2H+1H), 3.20 (dd, J=4, 16 Hz, 1H), 3.37 (s, 3H), 3.80 (t, J=8 Hz, 2H), 4.32 (m, 2H), 4.42 (m, 1H), 6.05 (d, 1H, NH), 6.67 (s, 1H), 7.29 (A of ABq, J=8 Hz, 2H), 7.69 (B of ABq, J=8 Hz, 2H); LC/MS ($C_{21}H_{27}N_3O_3$): RT 5.03 min: m/z 370.22 (M+1); HPLC: RT 4.39 min, >99%

Compound 53

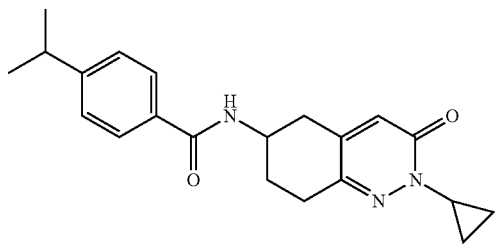

¹H NMR (CDCl₃, 400 MHz) δ 1.20 (two d, J=8 Hz, ratio 2:1, 6H), 1.5-2.2 (set of m, overlapped with H2O, 4.5H+1.5H+1H), 2.45 (m, 1H+1H), 2.87 and 3.28 (two dd, ratio 2:1, 1H), 2.94 (two m, 1H+1H), 4.15 and 4.70 (two m, ratio 2:1, 1H), 5.84 and 5.90 (two s, ratio 2:1, 1H), 6.03 and 6.17 (two brd, ratio 2:1, 1H), 7.29 (two d, ratio 2:1, J=8 Hz, 2H), 7.71 and 7.70 (two d, ratio 2:1, J=8 Hz, 2H): LC/MS (C21H25N3O2): RT 4.97 min: m/z 352.20 (M+1); HPLC: 4.29 min, >99%

Compound 54

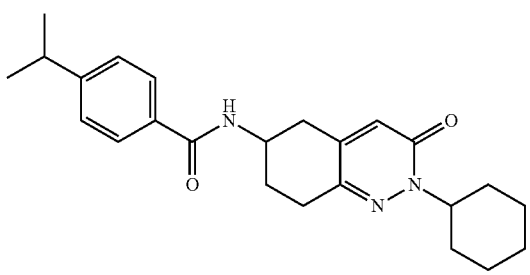

¹H NMR (CDCl₃, 400 MHz) δ 1.27 (d J=8 Hz, 6H+2H), 1.75 (m, overlapped, 4H), 1.80~1.95 (m, 3H+1H), 2.0-2.3 (set of m, 1H+1H), 2.5~2.7 (set of m, 1H), 2.8~3.0 (set of m, 2H+1H), 3.20 (two d, J=4, 16 Hz, 1H), 4.10 (two m, 0.5H), 4.49 (two m, 1H), 4.88 (m 0.5H), 6.03 (two d, 1H, NH), 6.65 (s, 1H), 7.30 (A of ABq, J=8 Hz, 2H), 7.68 (B of ABq, J=8 Hz, 2H); LC/MS ($C_{24}H_{31}N_3O_2$): RT 6.02 min: m/z 394.29 (M+1); HPLC: RT 5.86 min, >99%

Compound 55

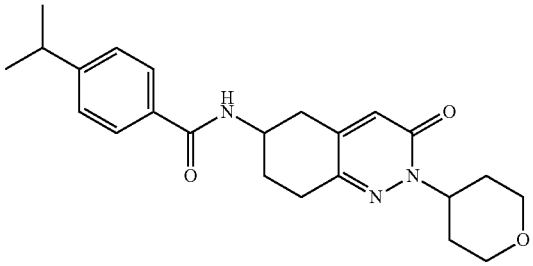

¹H NMR (CDCl₃, 400 MHz) δ 1.25 (set of d, 6H+6H), 1.4-1.7 (br, 3H), 1.75 (m, J=12 Hz, 1H), 1.9~2.1 (set of m, 2H), 2.7~3.0 (set of m, 2H+2H), 3.24 (dd, 1H) 3.57 (dt, 2H), 4.10 (dt, 2H), 4.42 and 5.16 (two m, 1H+1H), 6.00 (br d, 1H), 6.67 (s, 0.4H), 7.33 and 7.67 (AB of AB quartet, 2H+2H); LC/MS ($C_{23}H_{29}N_3O_3$): RT 5.10 min: m/z 396.05 (M+1); HPLC: RT 4.66 min, 98%

Compound 56

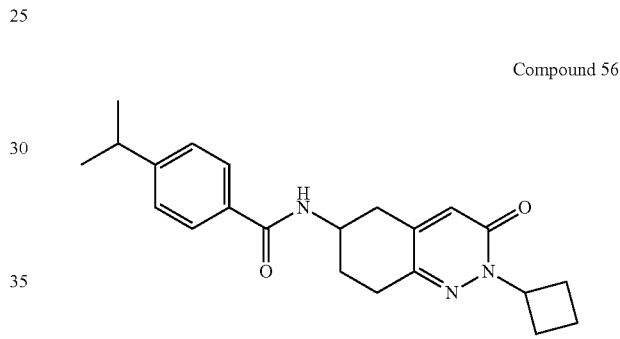

¹H NMR (CDCl₃, 400 MHz) δ 1.27 (d J=8 Hz, 6H), 1.80-1.95 (m, 2H+1H), 2.2-2.4 (set of m, 2H+1H), 2.45 (m, 2H), 2.66 (two dd, J=1, 4, 8 Hz, 1H), 2.8-3.0 (set of m, 2H+1H), 3.20 (two d, J=4, 16 Hz, 1H), 4.45 (m, 1H), 5.45 (m, 1H), 6.04 (d, 1H, NH), 6.62 (s, 1H), 7.30 (A of ABq, J=8 Hz, 2H), 7.68 (B of ABq, J=8 Hz, 2H); LC/MS ($C_{22}H_{27}N_3O_2$): RT 5.48 min: m/z 366.25 (M+1); HPLC: RT 5.21 min, 96%

Compound 58

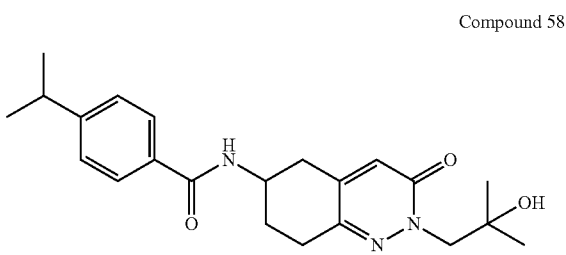

¹H NMR (CDCl₃, 400 MHz) δ 1.25 and 1.27 (d and s, J=8 Hz, 12H), 1.90 (m, 1H), 2.28 (m, 1H), 2.70 (two dd, J=1, 4, 8 Hz, 1H), 2.8-3.0 (set of m, 2H+1H), 3.25 (two d, J=4, 16 Hz, 1H), 4.25 (ABq, J=12 Hz, 2H), 4.43 (m 1H), 6.03 (d, 1H, NH), 6.75 (s, 1H), 7.30 (A of ABq, J=8 Hz, 2H), 7.68 (B of ABq, J=8 Hz, 2H); LC/MS ($C_{22}H_{29}N_3O_3$): RT 4.87 min: m/z 383.95 (M+1); HPLC: RT 4.29 min, 99%

Compound 59

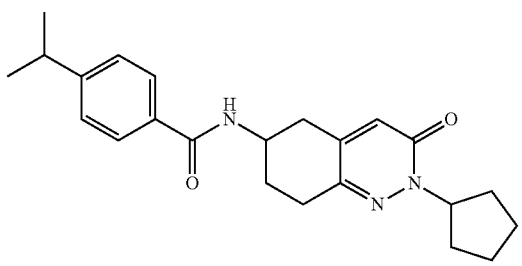

$^1$H NMR (CDCl$_3$, 400 MHz) δ 1.27 (d J=8 Hz, 6H+2H), 1.4~2.2 (set of m, 6H+2H), 2.8~3.0 (set of m, 2H+1H+1H), 3.20 (two d, J=4, 16 Hz, 1H), 4.4~4.7 (set of m, 1H+0.5H), 5.40 (m, 0.5H), 6.13 (two d, 1H, NH), 6.65 (s, 1H), 7.30 (m, 2H), 7.68 (m 2H): LC/MS (C$_{23}$H$_{29}$N$_3$O$_2$): RT 5.68 min: m/z 380.11 (M+1); HPLC: RT 5.34 min, >99%

Example 2 In Vitro Testing of DQ2 Inhibitory Compounds

Three commercially available analogues of the DQ2 binding molecules of the invention were tested for their ability to inhibit stimulation of T cell receptor (TCR) transductants in the presence of HLA-DQ2 expressing cells presenting known α-gliadin epitopes.

Using a previously published in vitro assay (Ostrov D, et al. Methyldopa blocks MHC class II binding to disease specific antigens in autoimmune diabetes. *J Clin Invest.* 2018:128(5)) we measured the ability of these DQ2 binding analogues to inhibit interleukin-2 (IL-2) secretion by TCR transductants stimulated by α-gliadin peptides presented by HLA-DQ2. Individual TCR transductants (recognizing α I-gliadin or α II-gliadin) were cultured with a gliadin peptide plus the small molecule analogues in the presence of HLA-DQ2 expressing K562 cells serving as antigen presenting cells. TCR transductants cultured with no gliadin peptide served as the negative control, and incubation with an anti-CD3 antibody (eBioscience; clone 2C11) served as a positive control for the TCR transductant. Secreted IL-2 in the culture supernatant was measured using a highly sensitive enzyme-linked immunosorbent assay (ELISA). A dose-response curve was generated for each of the tested analogs and the concentration at which the compound exhibited maximum % inhibition was determined. Assays for effects on cell viability and for specificity, assayed in the absence of gliadin peptide or in the presence of a stimulating anti-CD3 antibody, were performed. A=71-100%; B=41-70%; C=11-40%; D=0-10%, NT=Not tested.

| Number | Structure | MW | DQ2 IL2 Maximal % Inhibition (concentration in μM) |
|---|---|---|---|
| 1 | 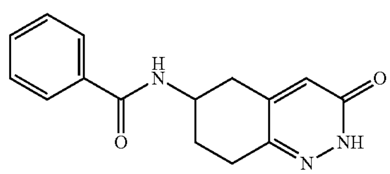 | 269.30 | C (50) |
| 2 | 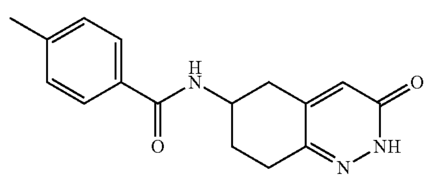 | 283.33 | C (100) |
| 3 | 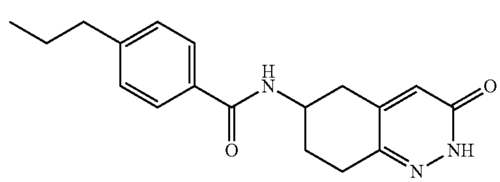 | 311.39 | B (100) |
| 4 | 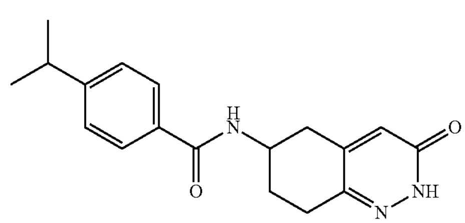 | 311.39 | A (200) |

-continued
| Number | Structure | MW | DQ2 IL2 Maximal % Inhibition (concentration in μM) |
|---|---|---|---|
| 5 | 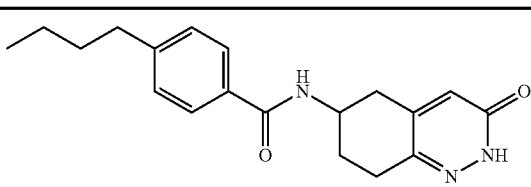 | 325.41 | D (50) |
| 6 | 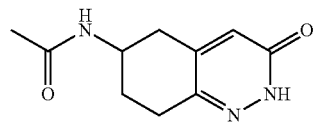 | 207.23 | C (50) |
| 7 | 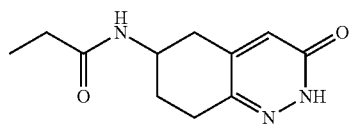 | 226.26 | D (200) |
| 8 | 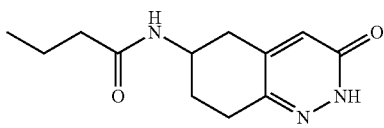 | 235.29 | D (200) |
| 9 | 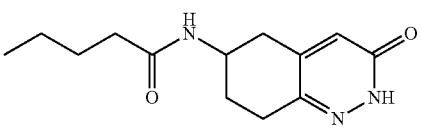 | 249.31 | C (100) |
| 10 | 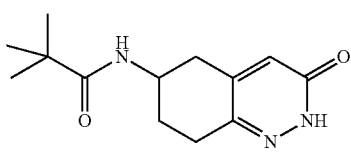 | 249.31 | D (200) |
| 11 | 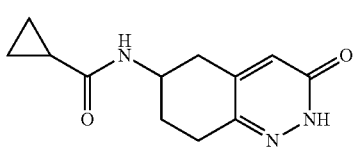 | 233.27 | D (200) |
| 12 | 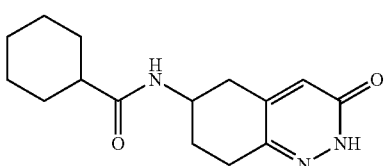 | 275.35 | C (0.1) |
| 13 | 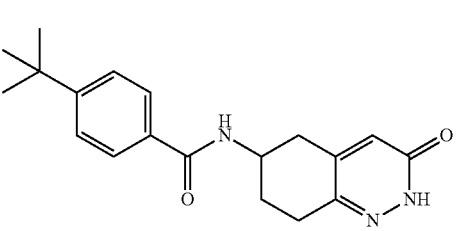 | 325.40 | D (0.1) |

-continued

| Number | Structure | MW | DQ2 IL2 Maximal % Inhibition (concentration in μM) |
|---|---|---|---|
| 14 | 4-cyclohexylbenzamide linked to 6-amino-2,5,6,7,8-tetrahydrocinnolin-3(2H)-one | 351.44 | B (200) |
| 15 | isobutyramide linked to 6-amino-2,5,6,7,8-tetrahydrocinnolin-3(2H)-one | 235/28 | C (100) |
| 16 | benzamide linked to 6-amino-2-methyl-5,6,7,8-tetrahydrocinnolin-3(2H)-one | 283.33 | B (100) |
| 17 | naphthalene-2-carboxamide linked to 6-amino-2-methyl-5,6,7,8-tetrahydrocinnolin-3(2H)-one | 333.38 | A (100) |
| 18 | acetamide linked to 6-amino-2-methyl-5,6,7,8-tetrahydrocinnolin-3(2H)-one | 221.26 | C (100) |
| 19 | cyclohexanecarboxamide linked to 6-amino-2-methyl-5,6,7,8-tetrahydrocinnolin-3(2H)-one | 289.37 | B (100) |
| 20 | 4-methylbenzamide linked to 6-amino-2-methyl-5,6,7,8-tetrahydrocinnolin-3(2H)-one | 297.35 | B (200) |
| 21 | 4-(trifluoromethyl)benzamide linked to 6-amino-2-methyl-5,6,7,8-tetrahydrocinnolin-3(2H)-one | 351.33 | A (100) |

-continued

| Number | Structure | MW | DQ2 IL2 Maximal % Inhibition (concentration in μM) |
|---|---|---|---|
| 22 | 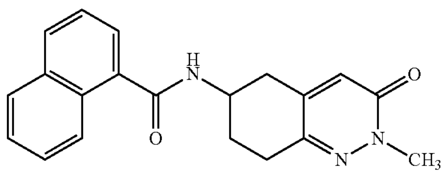 | 333.39 | C (200) |
| 23 | 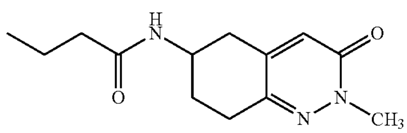 | 249.31 | C (100) |
| 24 | 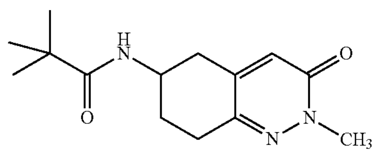 | 263.34 | C (100) |
| 25 | 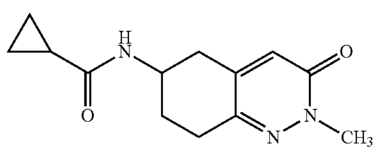 | 247.30 | C (200) |
| 26 | 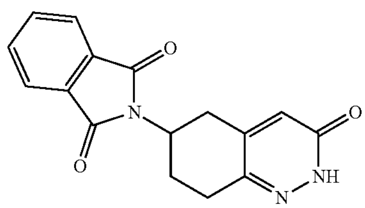 | 295.30 | C (200) |
| 27 | 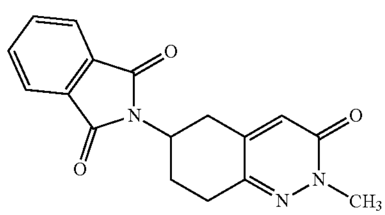 | 309.33 | C (200) |
| 28 | 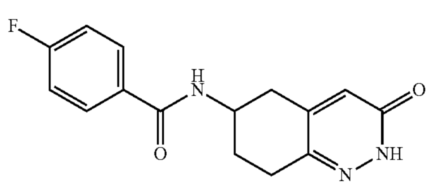 | 287.29 | C (200) |
| 29 | 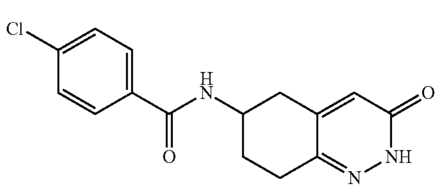 | 303.76 | B (200) |

-continued

| Number | Structure | MW | DQ2 IL2 Maximal % Inhibition (concentration in μM) |
|---|---|---|---|
| 30 | 4-Br-C6H4-C(=O)-NH-(5,6,7,8-tetrahydro-3-oxo-2H-cinnolin-6-yl) | 348.20 | C (200) |
| 31 | 4-I-C6H4-C(=O)-NH-(5,6,7,8-tetrahydro-3-oxo-2H-cinnolin-6-yl) | 395.20 | C (200) |
| 32 | 4-F-C6H4-C(=O)-NH-(5,6,7,8-tetrahydro-3-oxo-2-methyl-cinnolin-6-yl) | 301.32 | C (200) |
| 33 | 4-Cl-C6H4-C(=O)-NH-(5,6,7,8-tetrahydro-3-oxo-2-methyl-cinnolin-6-yl) | 317.77 | B (200) |
| 34 | 4-Br-C6H4-C(=O)-NH-(5,6,7,8-tetrahydro-3-oxo-2-methyl-cinnolin-6-yl) | 362.23 | A (200) |
| 35 | 4-I-C6H4-C(=O)-NH-(5,6,7,8-tetrahydro-3-oxo-2-methyl-cinnolin-6-yl) | 409.23 | B (200) |
| 36 | 4-Et-C6H4-C(=O)-NH-(5,6,7,8-tetrahydro-3-oxo-2-ethyl-cinnolin-6-yl) | 325.41 | B (200) |
| 37 | 4-Et-C6H4-C(=O)-NH-(5,6,7,8-tetrahydro-3-oxo-2-propyl-cinnolin-6-yl) | 339.44 | B (200) |

-continued
| Number | Structure | MW | DQ2 IL2 Maximal % Inhibition (concentration in μM) |
|---|---|---|---|
| 38 | 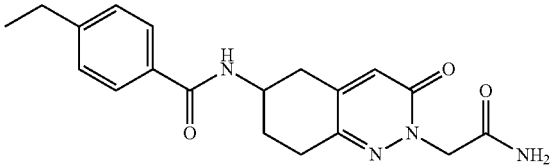 | 354.41 | A (200) |
| 39 | 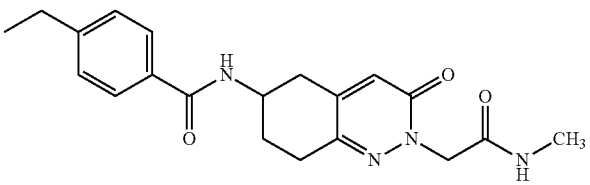 | 382.46 | NT |
| 40 | 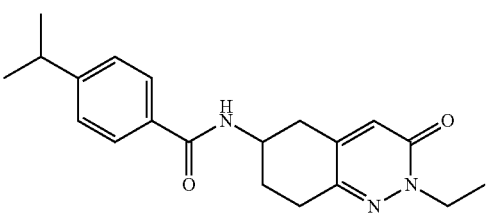 | 339.44 | B (200) |
| 41 | 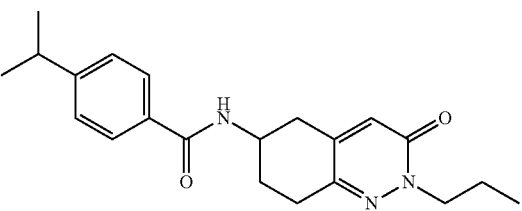 | 353.47 | A (200) |
| 42 | 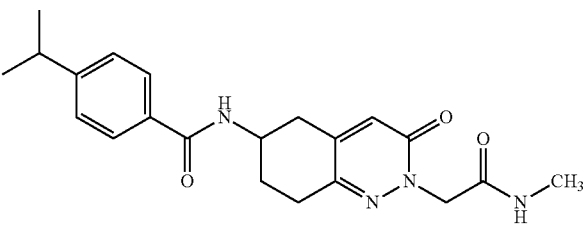 | 382.46 | A (200) |
| 43 | 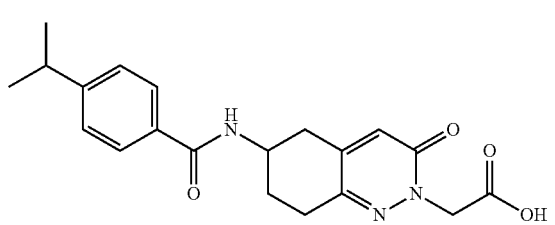 | 369.42 | A (200) |
| 44 | 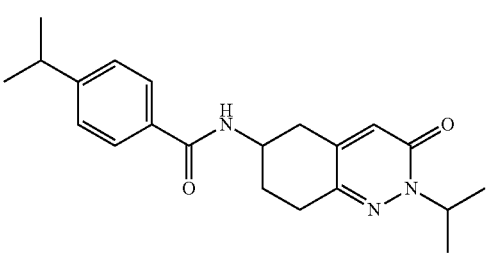 | 353.47 | A (200) |

-continued
| Number | Structure | MW | DQ2 IL2 Maximal % Inhibition (concentration in μM) |
|---|---|---|---|
| 45 | 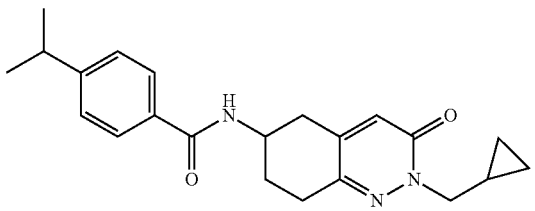 [SMILES: CC(C)c1ccc(C(=O)NC2CCc3nn(CC4CC4)c(=O)cc3C2)cc1] | 365.48 | A (200) |
| 46 | 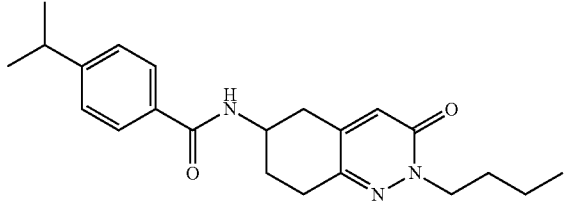 [SMILES: CCCCn1nc2c(cc1=O)CC(NC(=O)c1ccc(C(C)C)cc1)CC2] | 367.49 | B (200) |
| 47 | 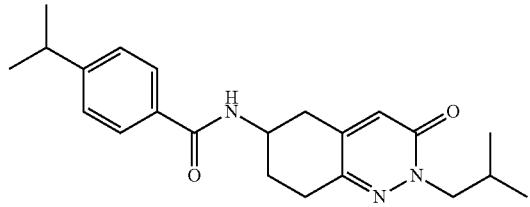 | 367.49 | NT |
| 48 | 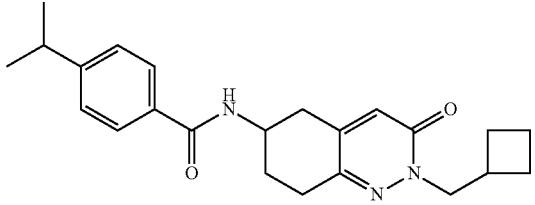 [SMILES: CC(C)c1ccc(C(=O)NC2CCc3nn(CC4CCC4)c(=O)cc3C2)cc1] | 379.50 | A (100) |
| 49 | 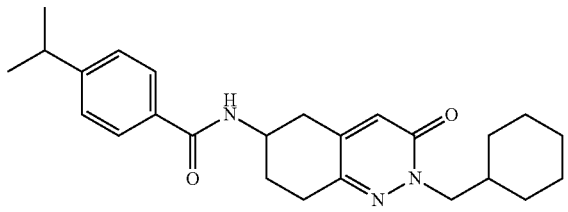 [SMILES: CC(C)c1ccc(C(=O)NC2CCc3nn(CC4CCCCC4)c(=O)cc3C2)cc1] | 407.56 | A (200) |
| 50 | 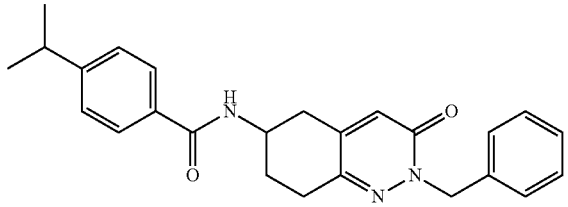 [SMILES: CC(C)c1ccc(C(=O)NC2CCc3nn(Cc4ccccc4)c(=O)cc3C2)cc1] | 401.51 | A (200) |

-continued

| Number | Structure | MW | DQ2 IL2 Maximal % Inhibition (concentration in μM) |
|---|---|---|---|
| 51 | 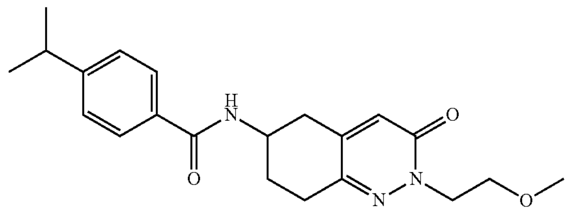 | 369.47 | B (200) |
| 52 | 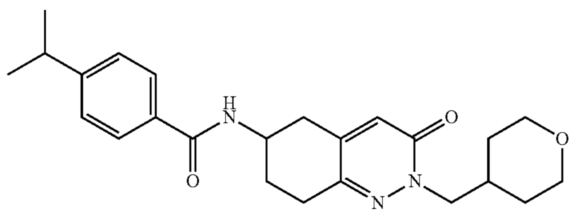 [SMILES: CC(C)c1ccc(C(=O)NC2CCc3nn(CC4CCOCC4)c(=O)cc3C2)cc1] | 409.53 | NT |
| 53 | 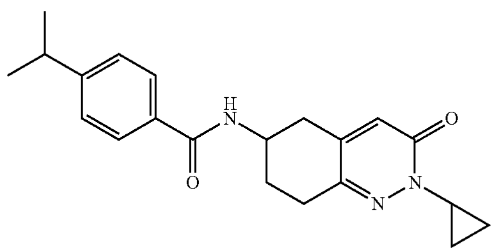 [SMILES: CC(C)c1ccc(C(=O)NC2CCc3nn(C4CC4)c(=O)cc3C2)cc1] | 351.45 | A (200) |
| 54 | 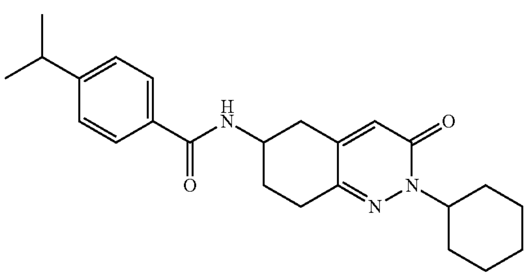 [SMILES: CC(C)c1ccc(C(=O)NC2CCc3nn(C4CCCCC4)c(=O)cc3C2)cc1] | 393.53 | A (200) |
| 55 | 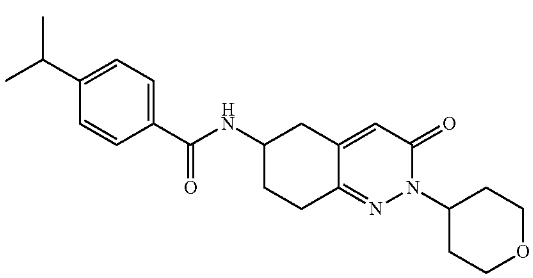 [SMILES: CC(C)c1ccc(C(=O)NC2CCc3nn(C4CCOCC4)c(=O)cc3C2)cc1] | 395.50 | A (200) |
| 56 | 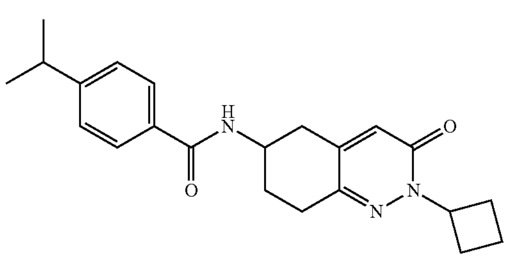 [SMILES: CC(C)c1ccc(C(=O)NC2CCc3nn(C4CCC4)c(=O)cc3C2)cc1] | 365.48 | A (200) |

TABLE 2-continued

| Number | Structure | MW | DQ2 IL2 Maximal % Inhibition (concentration in μM) |
|---|---|---|---|
| 57 | 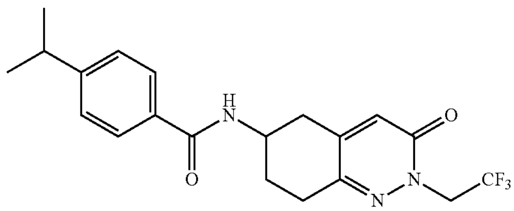 [SMILES: CC(C)c1ccc(C(=O)NC2CCc3nn(CC(F)(F)F)c(=O)cc3C2)cc1] | 393.41 | A (200) |
| 58 | 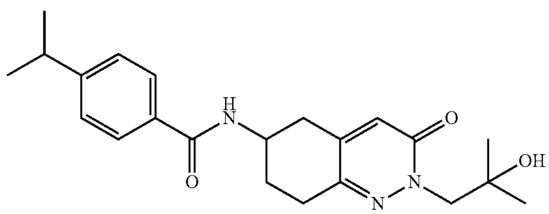 [SMILES: CC(C)c1ccc(C(=O)NC2CCc3nn(CC(C)(C)O)c(=O)cc3C2)cc1] | 383.49 | A (200) |
| 59 | 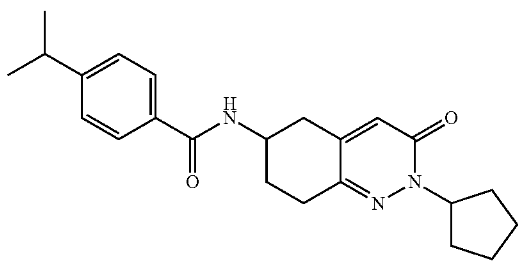 [SMILES: CC(C)c1ccc(C(=O)NC2CCc3nn(C4CCCC4)c(=O)cc3C2)cc1] | 379.50 | A (200) |

TABLE 2

| | Structure | DQ2 IL2 Maximal % Inhibition (concentration in μM) |
|---|---|---|
| 60 | 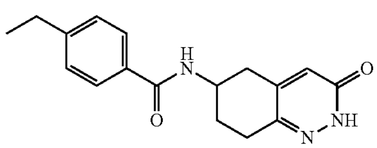 [SMILES: CCc1ccc(C(=O)NC2CCc3n[nH]c(=O)cc3C2)cc1] | A (200) |
| 61 | 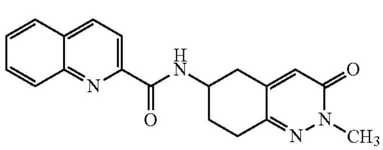 [SMILES: Cn1nc2c(cc1=O)CC(NC(=O)c1ccc3ccccc3n1)CC2] | A (200) |
| 62 | 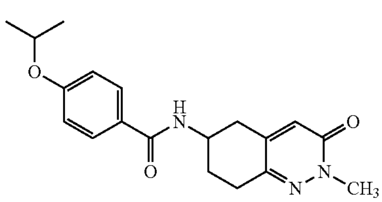 [SMILES: CC(C)Oc1ccc(C(=O)NC2CCc3nn(C)c(=O)cc3C2)cc1] | A (200) |
| 63 | | A (200) |

It will be apparent to those skilled in the art that many more modifications besides those already described are possible without departing from the inventive concepts herein. The inventive subject matter, therefore, is not to be restricted except in the scope of the appended claims.

What is claimed is:

1. A pharmaceutical composition comprising a compound of Formula (I),

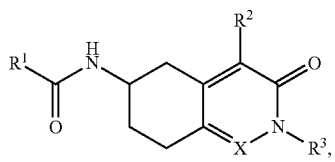 (I)

or a pharmaceutically acceptable salt thereof, wherein
  $R^1$ is H, optionally substituted $C_1$-$C_6$-alkyl; optionally substituted aryl; optionally substituted $C_3$-$C_7$-cycloalkyl; optionally substituted heterocyclyl; or optionally substituted heteroaryl;
  $R^2$ is H, optionally substituted $C_{1-6}$ alkyl, or $OR^4$ wherein $R^4$ is H or optionally substituted $C_{1-6}$ alkyl;
  $R^3$ is H, optionally substituted $C_1$-$C_6$-alkyl optionally substituted $C_3$-$C_8$-cycloalkyl; optionally substituted aryl; optionally substituted heteroaryl; optionally substituted 3 to 8 membered heterocyclyl; or —$(CH_2)_n$—Y, where n is 1-4 and Y is optionally substituted $C_3$-$C_8$-cycloalkyl; optionally substituted heterocyclyl; optionally substituted aryl; optionally substituted heteroaryl; optionally substituted $C_1$-$C_6$-alkoxy; —C(O)OH or —C(O)N($R^8$)$_2$;
  each $R^8$ is independently H or $C_1$-$C_6$-alkyl; and
X is N or $CR^5$; wherein $R^5$ is H or optionally substituted $C_{1-6}$ alkyl; and
a pharmaceutically acceptable carrier;
wherein
  each heteroaryl is selected from the group consisting of pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, and quinoxalinyl,
  each heterocyclyl is selected from the group consisting of 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, 2-azabicyclo[2.2.1]-heptyl, 8-azabicyclo[3.2.1]octyl, 5-azaspiro[2.5]octyl, 7-oxooxepan-4-yl, tetrahydropyranyl, and tetrahydrofuryl, and
  each optionally substituted group is optionally substituted with 1 or more substituents independently selected from the group consisting of halogen, $C_1$-$C_4$-alkyl, halo-$C_1$-$C_4$-alkyl, $C_2$-$C_4$-alkenyl, halo-$C_2$-$C_4$-alkenyl, $C_3$-$C_6$-cycloalkyl, $C_1$-$C_4$-alkoxy, halo-$C_1$-$C_4$-alkoxy, —CN, OH, $NH_2$, $C_1$-$C_4$-alkylamino, di($C_1$-$C_4$-alkyl)amino, and $NO_2$.

2. The pharmaceutical composition of claim 1 wherein $R^1$ is optionally substituted $C_1$-$C_4$-alkyl; optionally substituted phenyl, optionally substituted naphthyl, or optionally substituted quinolyl.

3. The pharmaceutical composition of claim 1, wherein:
  $R^1$ is H; $C_1$-$C_4$-alkyl; $C_{3-7}$ cycloalkyl; or

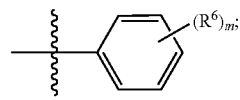

$R^2$ is H, $C_{1-4}$ alkyl, or $OR^4$;
  $R^3$ is H, $CH_3$, $CH_2CH_3$, $CH_2CH_2CH_3$, $CH(CH_3)_2$, $CH_2CH(CH_3)_2$; $C_3$-$C_6$-cycloalkyl; saturated 5-6-membered heterocyclyl; or —$(CH_2)_n$—Y, where n is 1 or 2; and Y is optionally substituted phenyl; $C_3$-$C_6$-cycloalkyl; saturated 5-6-membered heterocyclyl; C(O)OH or C(O)N($R^8$)$_2$, wherein each $R^8$ is independently H or methyl;
  $R^4$ is H, or $C_{1-4}$ alkyl;
  Each $R^6$ is independently halogen, $C_1$-$C_4$-alkyl, halo-$C_1$-$C_4$-alkyl; $C_1$-$C_4$-alkoxy, halo-$C_1$-$C_4$-alkoxy, or $C_{3-6}$ cycloalkyl;
  X is N or $CR^5$, where $R^5$ is H or $C_{1-4}$ alkyl; and
  m is 0 to 5.

4. The pharmaceutical composition of claim 3, wherein $R^1$ is methyl, ethyl, n-propyl, isopropyl, n-butyl, sec-butyl, t-butyl, cyclopropyl; cyclohexyl, or

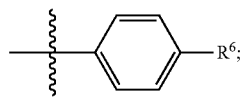

$R^6$ is halogen, trifluoromethyl; methyl, ethyl, n-propyl, isopropyl, n-butyl, sec-butyl, t-butyl, or cyclohexyl;
  $R^2$ is H, hydroxyl, methyl or methoxy;
  $R^3$ is H or $CH_3$; and
  X is N.

5. The pharmaceutical composition of claim 1, wherein the compound of Formula I is selected from the compounds set forth in the table below:

1

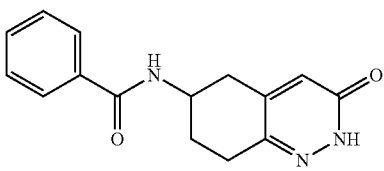 [SMILES: O=C(NC1CCc2n[nH]c(=O)cc2C1)c1ccccc1]

2

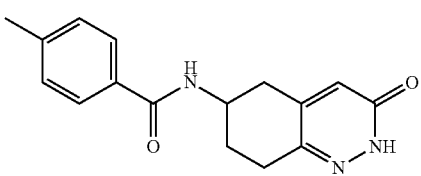 [SMILES: Cc1ccc(C(=O)NC2CCc3n[nH]c(=O)cc3C2)cc1]

-continued
3 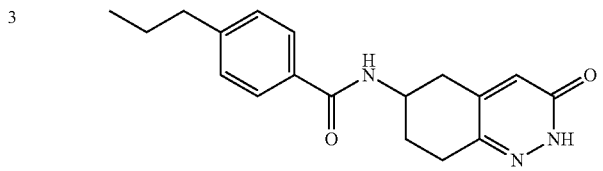
4 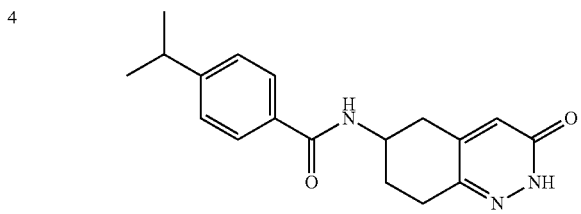
5 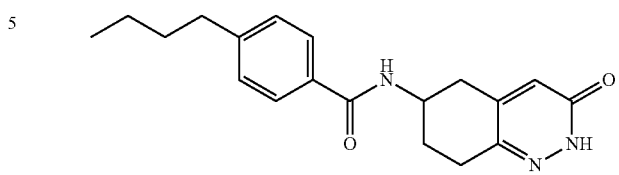
6 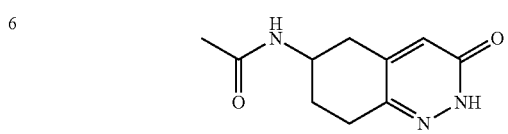
7 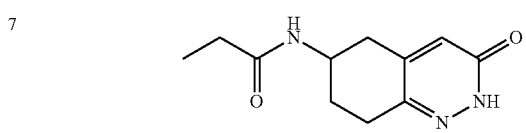
8 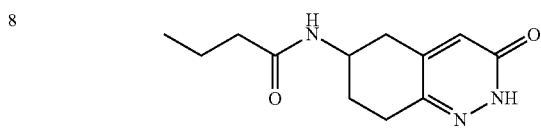
9 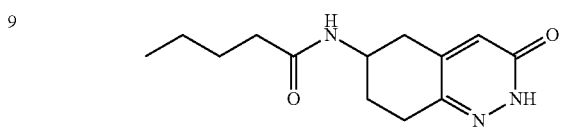
10 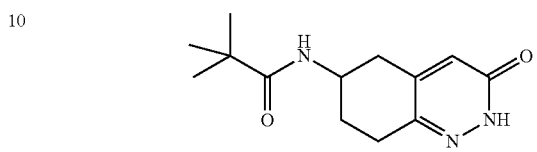
11 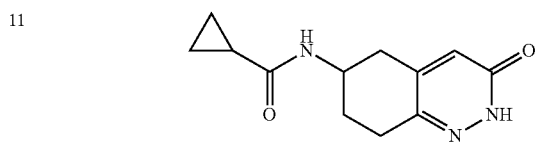
12 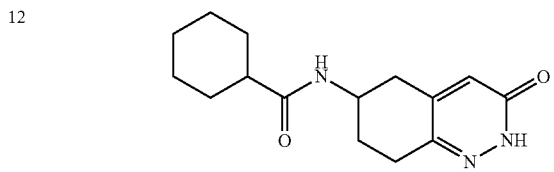

| | |
|---|---|
| 13 | 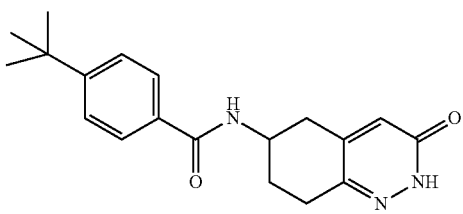 [SMILES: CC(C)(C)c1ccc(C(=O)NC2CCc3n[nH]c(=O)cc3C2)cc1] |
| 14 | 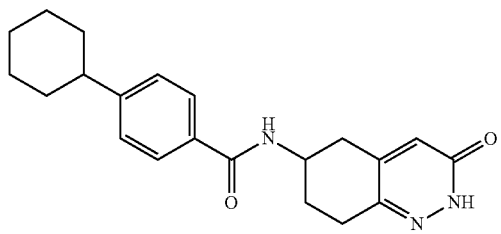 [SMILES: O=C(NC1CCc2n[nH]c(=O)cc2C1)c1ccc(C2CCCCC2)cc1] |
| 15 | 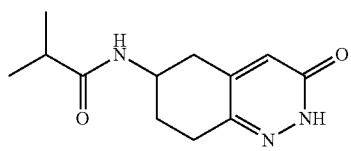 [SMILES: CC(C)C(=O)NC1CCc2n[nH]c(=O)cc2C1] |
| 16 | 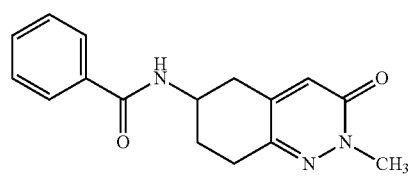 |
| 17 | 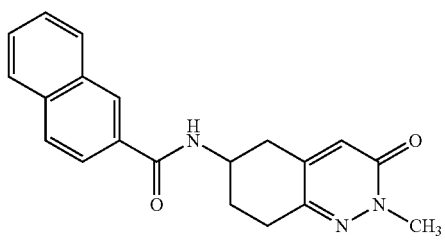 [SMILES: Cn1nc2c(cc1=O)CC(NC(=O)c1ccc3ccccc3c1)CC2] |
| 18 | 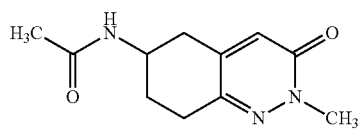 [SMILES: CC(=O)NC1CCc2nn(C)c(=O)cc2C1] |
| 19 | 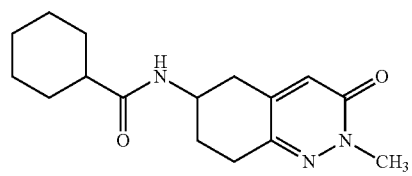 [SMILES: Cn1nc2c(cc1=O)CC(NC(=O)C1CCCCC1)CC2] |
| 20 | 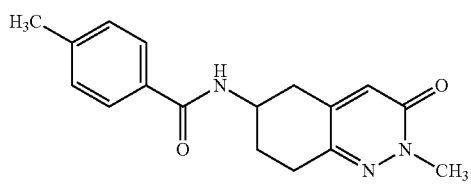 [SMILES: Cn1nc2c(cc1=O)CC(NC(=O)c1ccc(C(F)(F)F)cc1)CC2] |

-continued
| | |
|---|---|
| 21 | 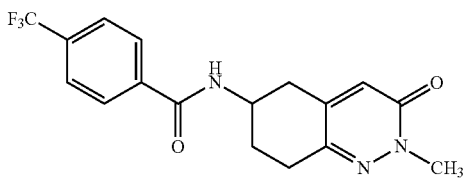 |
| 22 | 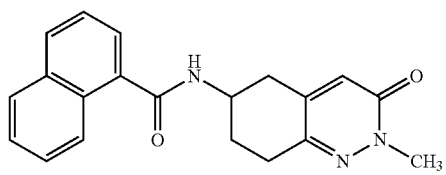 [SMILES: Cn1nc2c(cc1=O)CC(NC(=O)c1cccc3ccccc13)CC2] |
| 23 | 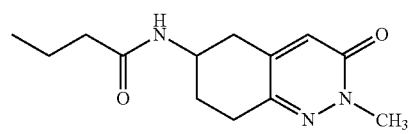 [SMILES: CCCC(=O)NC1CCc2nn(C)c(=O)cc2C1] |
| 24 | 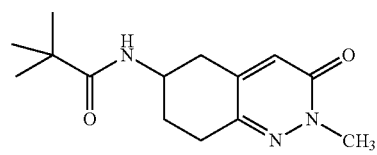 |
| 25 | 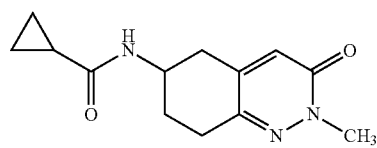 [SMILES: Cn1nc2c(cc1=O)CC(NC(=O)C1CC1)CC2] |
| 28 | 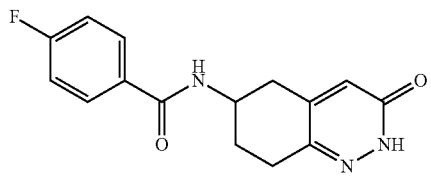 |
| 29 | 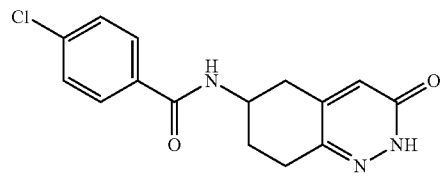 |
| 30 | 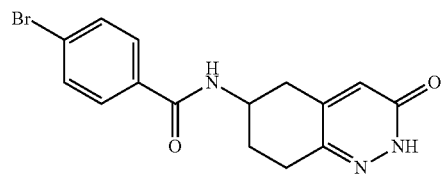 [SMILES: O=C(NC1CCc2n[nH]c(=O)cc2C1)c1ccc(Cl)cc1] |
| 31 | 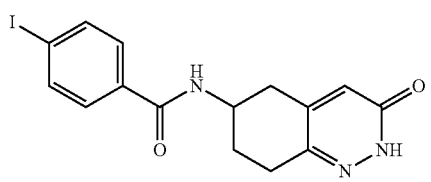 [SMILES: O=C(NC1CCc2n[nH]c(=O)cc2C1)c1ccc(I)cc1] |

-continued
| 32 | 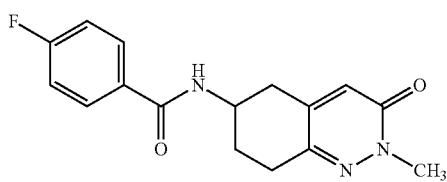 [SMILES: Cn1nc2c(cc1=O)CC(NC(=O)c1ccc(F)cc1)CC2] |
| 33 | 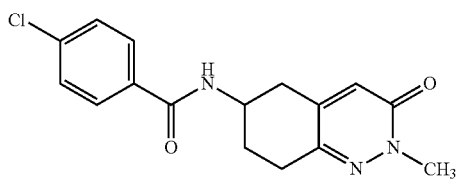 [SMILES: Cn1nc2c(cc1=O)CC(NC(=O)c1ccc(Cl)cc1)CC2] |
| 34 | 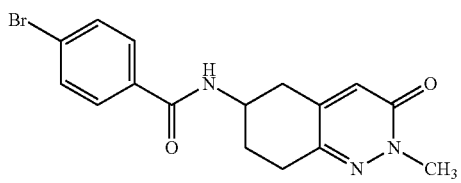 |
| 35 | 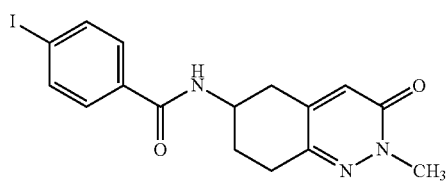 |
| 36 | 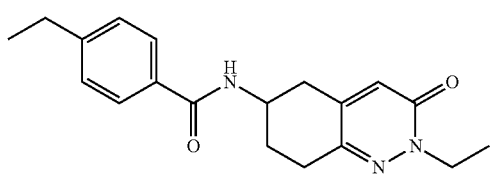 [SMILES: CCc1ccc(C(=O)NC2CCc3nn(CC)c(=O)cc3C2)cc1] |
| 37 | 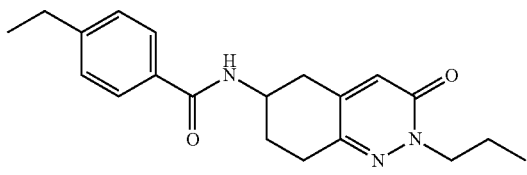 [SMILES: CCCn1nc2c(cc1=O)CC(NC(=O)c1ccc(CC)cc1)CC2] |
| 38 | 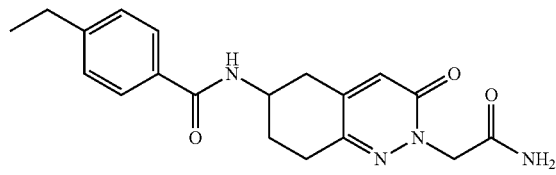 |
| 39 | 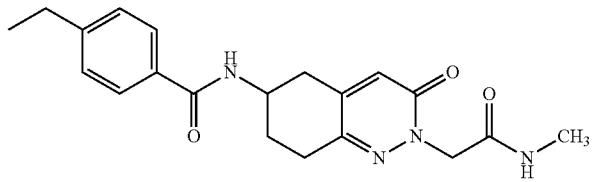 [SMILES: CCc1ccc(C(=O)NC2CCc3nn(CC(=O)NC)c(=O)cc3C2)cc1] |

-continued
| | |
|---|---|
| 40 | 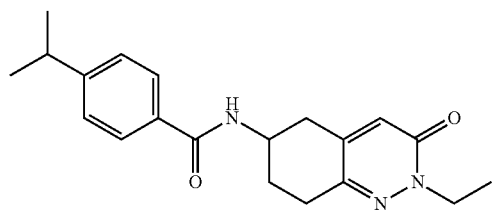 [SMILES: CCn1nc2c(cc1=O)CC(NC(=O)c1ccc(C(C)C)cc1)CC2] |
| 41 | 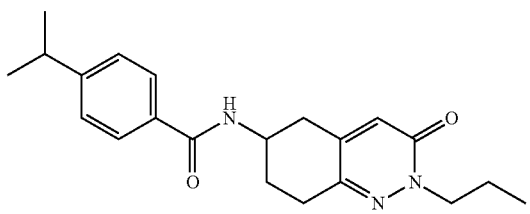 [SMILES: CCCn1nc2c(cc1=O)CC(NC(=O)c1ccc(C(C)C)cc1)CC2] |
| 42 | 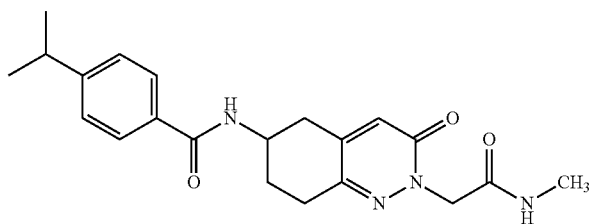 [SMILES: CNC(=O)Cn1nc2c(cc1=O)CC(NC(=O)c1ccc(C(C)C)cc1)CC2] |
| 43 | 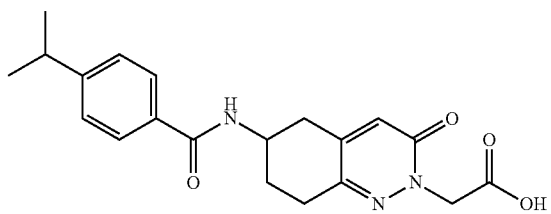 [SMILES: CC(C)c1ccc(C(=O)NC2CCc3nn(CC(=O)O)c(=O)cc3C2)cc1] |
| 44 | 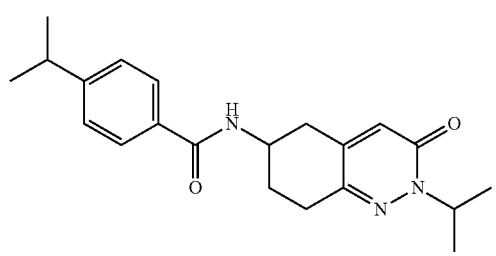 [SMILES: CC(C)c1ccc(C(=O)NC2CCc3nn(C(C)C)c(=O)cc3C2)cc1] |
| 45 | 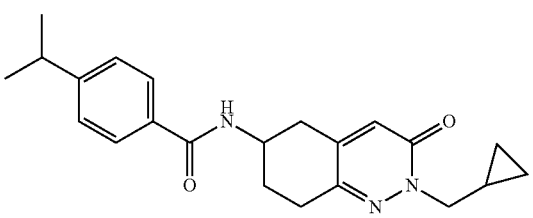 [SMILES: CC(C)c1ccc(C(=O)NC2CCc3nn(CC4CC4)c(=O)cc3C2)cc1] |
| 46 | 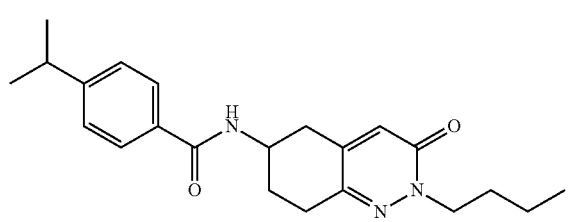 |

-continued
| | |
|---|---|
| 47 | 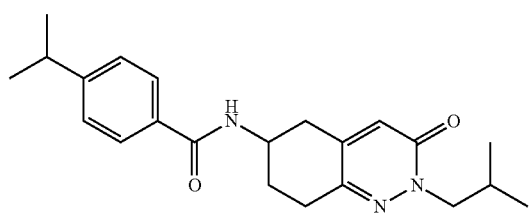 [SMILES: CC(C)Cn1nc2c(cc1=O)CC(NC(=O)c1ccc(C(C)C)cc1)CC2] |
| 48 | 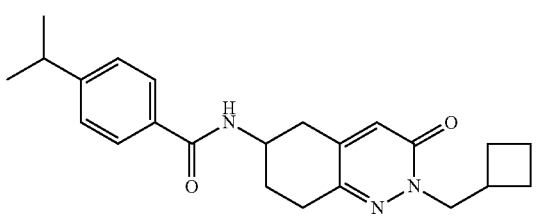 [SMILES: CC(C)c1ccc(C(=O)NC2CCc3nn(CC4CCC4)c(=O)cc3C2)cc1] |
| 49 | 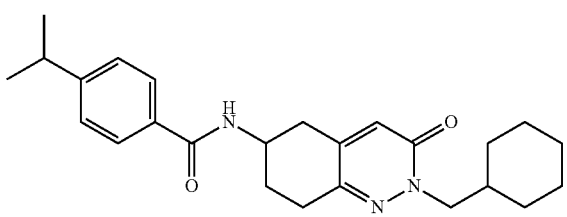 [SMILES: CC(C)c1ccc(C(=O)NC2CCc3nn(CC4CCCCC4)c(=O)cc3C2)cc1] |
| 50 | 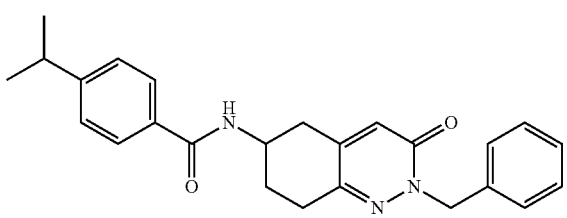 [SMILES: CC(C)c1ccc(C(=O)NC2CCc3nn(Cc4ccccc4)c(=O)cc3C2)cc1] |
| 51 | 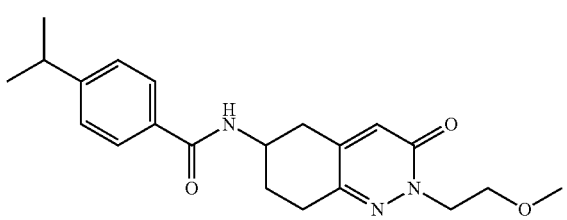 [SMILES: COCCn1nc2c(cc1=O)CC(NC(=O)c1ccc(C(C)C)cc1)CC2] |
| 52 | 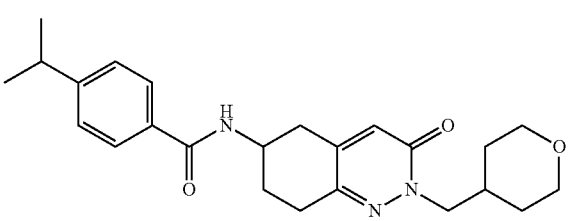 [SMILES: CC(C)c1ccc(C(=O)NC2CCc3nn(CC4CCOCC4)c(=O)cc3C2)cc1] |
| 53 | 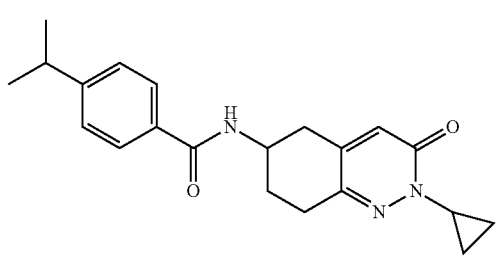 [SMILES: CC(C)c1ccc(C(=O)NC2CCc3nn(C4CC4)c(=O)cc3C2)cc1] |

-continued
| 54 | 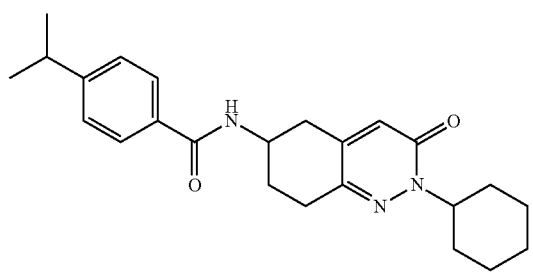 [SMILES: CC(C)c1ccc(C(=O)NC2CCc3nn(C4CCCCC4)c(=O)cc3C2)cc1] |
| --- | --- |
| 55 | 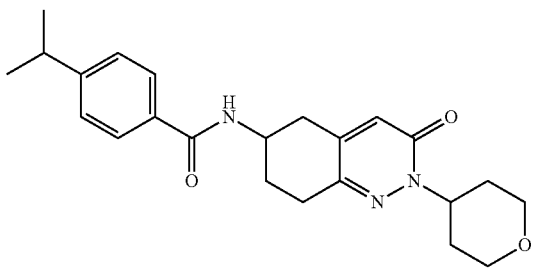 [SMILES: CC(C)c1ccc(C(=O)NC2CCc3nn(C4CCOCC4)c(=O)cc3C2)cc1] |
| 56 | 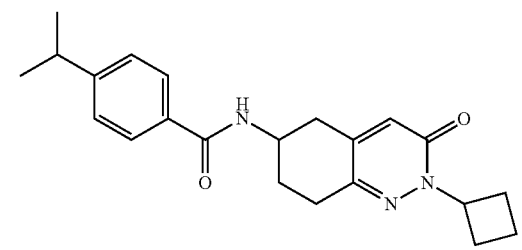 [SMILES: CC(C)c1ccc(C(=O)NC2CCc3nn(C4CCC4)c(=O)cc3C2)cc1] |
| 57 | 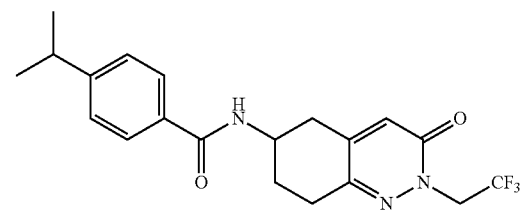 [SMILES: CC(C)c1ccc(C(=O)NC2CCc3nn(CC(F)(F)F)c(=O)cc3C2)cc1] |
| 58 | 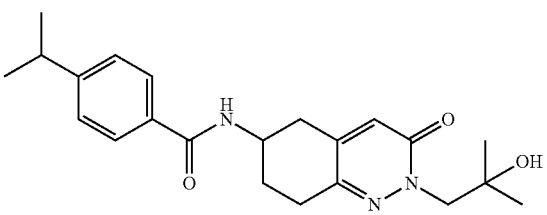 [SMILES: CC(C)c1ccc(C(=O)NC2CCc3nn(CC(C)(C)O)c(=O)cc3C2)cc1] |
| 59 | 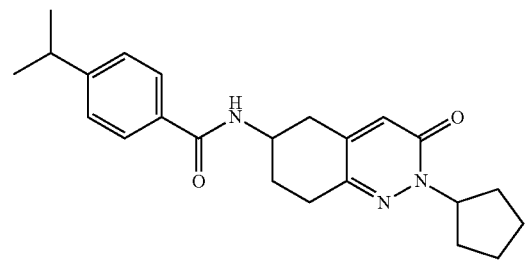 [SMILES: CC(C)c1ccc(C(=O)NC2CCc3nn(C4CCCC4)c(=O)cc3C2)cc1] |

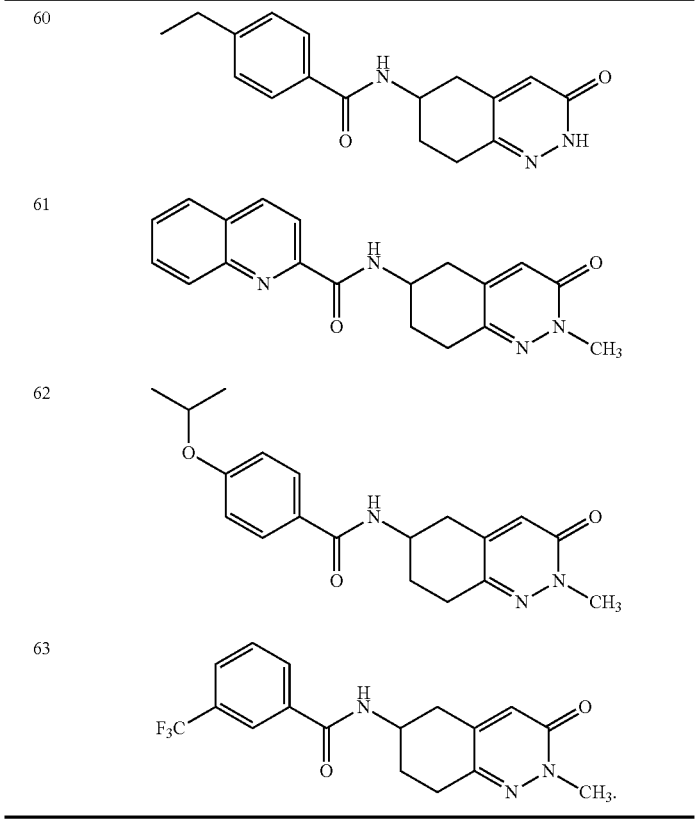

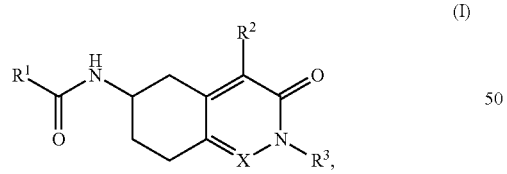

6. The pharmaceutical composition of claim 1, wherein the composition is formulated for oral or parenteral administration.

7. A method of treating an autoimmune disease selected from the group consisting of celiac disease, type 1 diabetes, Stiff-person syndrome, Addison's disease, Schmidt syndrome, and Myasthenia gravis in a subject in need thereof, comprising administering to the subject a therapeutically effective amount of a compound of Formula (I), (I)

or a pharmaceutically acceptable salt thereof, wherein
$R^1$ is H, optionally substituted $C_1$-$C_6$-alkyl; optionally substituted aryl; optionally substituted $C_3$-$C_7$-cycloalkyl; optionally substituted heterocyclyl; or optionally substituted heteroaryl;
$R^2$ is H, optionally substituted $C_{1-6}$ alkyl, or $OR^4$ wherein $R^4$ is H or optionally substituted $C_{1-6}$ alkyl;
$R^3$ is H, optionally substituted $C_1$-$C_6$-alkyl, optionally substituted $C_3$-$C_8$-cycloalkyl; optionally substituted aryl; optionally substituted heteroaryl; optionally substituted heterocyclyl; or —$(CH_2)_n$—Y, where n is 1-4 and Y is optionally substituted $C_3$-$C_8$-cycloalkyl; optionally substituted 3 to 8 membered heterocyclyl; optionally substituted aryl; optionally substituted heteroaryl; optionally substituted $C_1$-$C_6$-alkoxy; —C(O)OH or —C(O)N($R^8$)$_2$;
each $R^8$ is independently H or $C_1$-$C_6$-alkyl; and
X is N or $CR^5$; wherein $R^5$ is H or optionally substituted $C_{1-6}$ alkyl;
wherein
each heteroaryl is selected from the group consisting of pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, and quinoxalinyl,
each heterocyclyl is selected from the group consisting of 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, 2-azabicyclo[2.2.1]-heptyl, 8-azabicyclo[3.2.1]octyl, 5-azaspiro[2.5]octyl, 7-oxooxepan-4-yl, tetrahydropyranyl, and tetrahydrofuryl, and each optionally substituted group is optionally substituted with 1 or more substituents independently selected from the group consisting of halogen, $C_1$-$C_4$-alkyl, halo-$C_1$-$C_4$-alkyl, $C_2$-$C_4$-alkenyl, halo-$C_2$-$C_4$-alkenyl, $C_3$-$C_6$-cycloalkyl, $C_1$-$C_4$-alkoxy, halo-$C_1$-$C_4$-alkoxy, —CN, OH, $NH_2$, $C_1$-$C_4$-alkylamino, di($C_1$-$C_4$-alkyl)amino, and $NO_2$.

8. The method of claim 7, wherein $R^1$ is optionally substituted $C_1$-$C_4$-alkyl; optionally substituted phenyl, optionally substituted naphthyl, or optionally substituted quinolyl.

9. The method of claim 7, wherein:
R¹ is H; $C_1$-$C_4$-alkyl; $C_{3-7}$ cycloalkyl; naphthyl; or

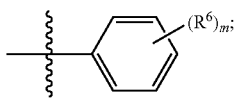

R² is H, $C_{1-4}$ alkyl, or OR⁴;
R³ is H, $CH_3$, $CH_2CH_3$, $CH_2CH_2CH_3$, or $CH(CH_3)_2$, $CH_2CH(CH_3)_2$; $C_3$-$C_6$-cycloalkyl; saturated 5-6-membered heterocyclyl; or —$(CH_2)_n$—Y, where n is 1 or 2; and Y is optionally substituted phenyl; $C_3$-$C_6$-cycloalkyl; saturated 5-6-membered heterocyclyl; C(O)OH or $C(O)(NR^8)_2$, where each R⁸ is independently H or methyl;
R⁴ is H, or $C_{1-4}$ alkyl;
Each R⁶ is independently halogen; $C_1$-$C_4$-alkyl, halo-$C_1$-$C_4$-alkyl; $C_1$-$C_4$-alkoxy, halo-$C_1$-$C_4$-alkoxy, or $C_{3-7}$ cycloalkyl;
X is N or CR⁵, wherein R⁵ is H or $C_{1-4}$ alkyl; and
m is 0 to 5.

10. The method of claim 9, wherein
R¹ is methyl, ethyl, n-propyl, isopropyl, n-butyl, sec-butyl; t-butyl; naphthyl, quinolyl, cyclopropyl, cyclohexyl; or

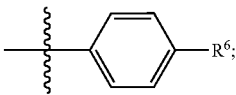

R⁶ is halogen, methyl, trifluoromethyl; ethyl, n-propyl, isopropyl, n-butyl; sec-butyl, t-butyl or cyclohexyl;

R² is H, hydroxyl, methyl or methoxy;
R³ is H or $CH_3$; and
X is N.

11. The method of claim 7, wherein the autoimmune disease is celiac disease and the administration alters the presentation of a gluten protein, a deaminated gluten protein, and/or fragments thereof, to T cells by DQ2 MHC class II molecules.

12. The method of claim 7, wherein the compound is administered orally to the subject.

13. The method of claim 7, wherein the subject has been determined to have anti-transglutaminase antibodies, antibodies against deamidated gliadin peptides, antibodies against acetylcholine receptor, antibodies against insulin (IAA), antibodies against beta cell-specific antigens, antibodies against glutamic acid decarboxylase (GAD), antibodies against insulinoma-associated antigen 2 (IA-2), antibodies against zinc transporter 8 (ZnT8), and/or anti-endomysium antibodies.

14. The method of claim 7, wherein the subject has been determined to have an HLA-DQ2 allele that presents a peptide to T cells, wherein the peptide is selected from the group consisting of: an insulin peptide, a gluten peptide, a beta cell-specific antigenic peptide, a glutamic acid decarboxylase 65 peptide, an insulinoma-associated antigen 2 peptide, a zinc transporter 8 peptide, an acetylcholine receptor peptide, and antigenic fragments thereof.

15. The method of claim 14, wherein the HLA-DQ2 is selected from the group consisting of: DQ2.5cis (DQA1*05:01-DQB1*02:01), DQ2.5trans (DQA1*05:05-DQB1*03:01/DQA1*02:01-DQB1*02:02), DQ2.2 (DQA1*02:01-DQB1*02:02), and DQ2.3 (DQA1*03:01-DQB1*02:01).

16. The method of claim 7, wherein the compound of Formula (I) is selected from the compounds set forth in the table below:

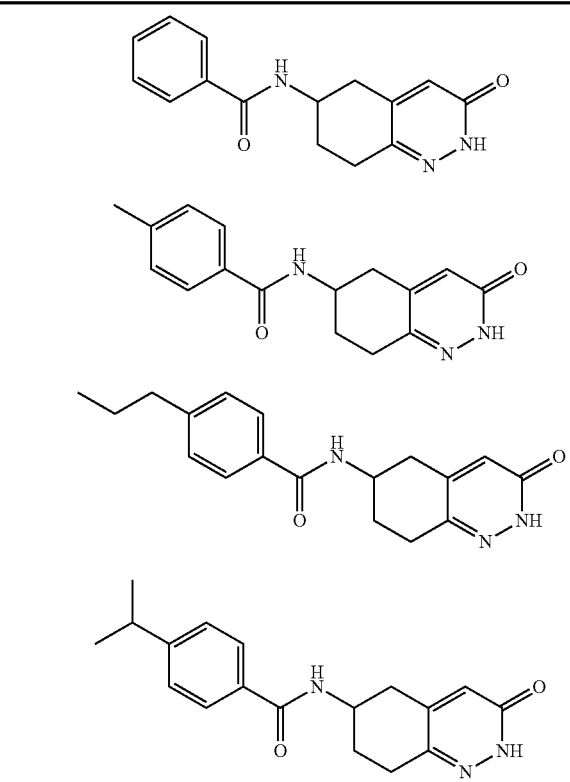

-continued
| 5 | 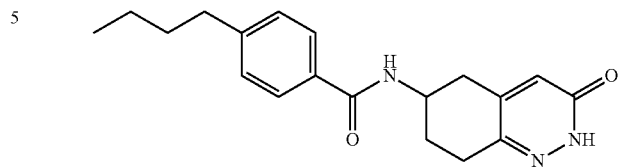 |
| --- | --- |
| 6 | 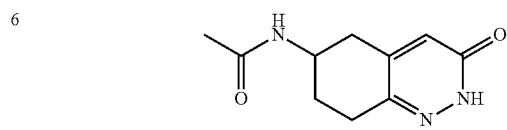 |
| 7 | 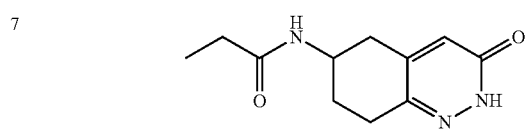 |
| 8 | 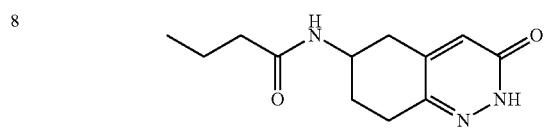 |
| 9 | 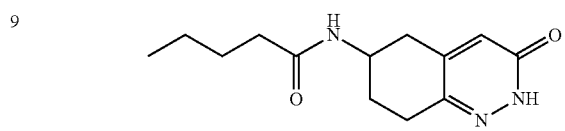 |
| 10 | 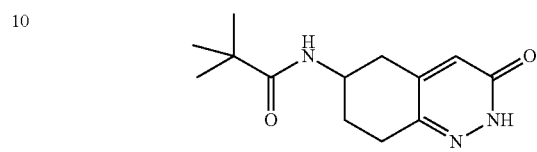 |
| 11 | 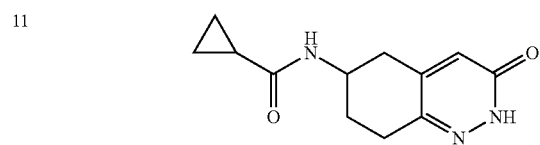 |
| 12 | 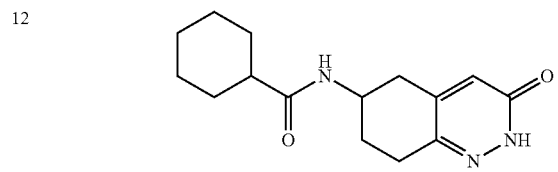 |
| 13 | 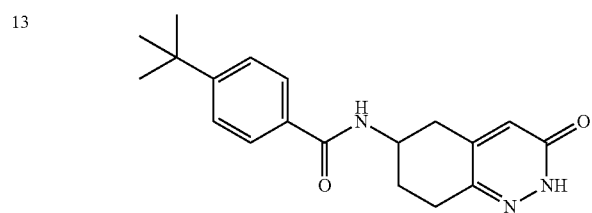 |

-continued
14 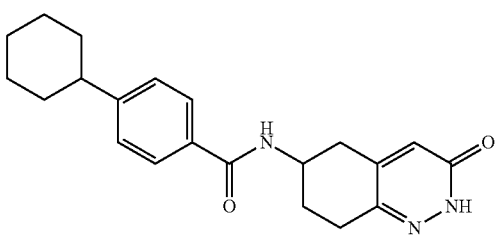 [SMILES: O=C(NC1CCc2n[nH]c(=O)cc2C1)c1ccc(C2CCCCC2)cc1]
15 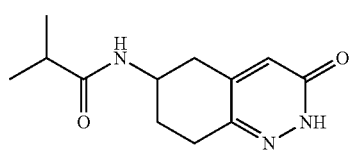 [SMILES: CC(C)C(=O)NC1CCc2n[nH]c(=O)cc2C1]
16 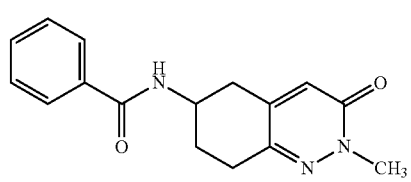 [SMILES: Cn1nc2c(cc1=O)CC(NC(=O)c1ccccc1)CC2]
17 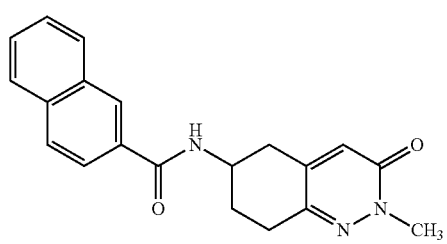 [SMILES: Cn1nc2c(cc1=O)CC(NC(=O)c1ccc3ccccc3c1)CC2]
18 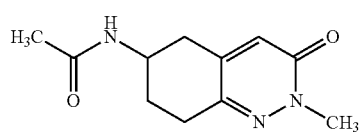 [SMILES: CC(=O)NC1CCc2nn(C)c(=O)cc2C1]
19 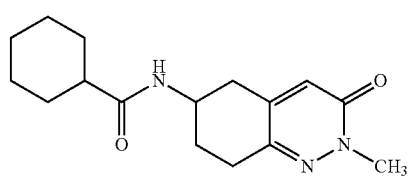 [SMILES: Cn1nc2c(cc1=O)CC(NC(=O)C1CCCCC1)CC2]
20 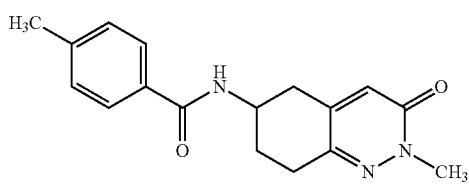
21 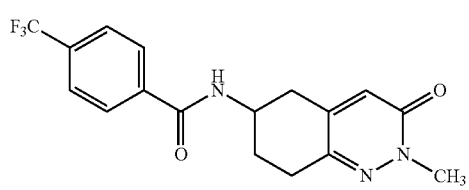 [SMILES: Cn1nc2c(cc1=O)CC(NC(=O)c1ccc(C(F)(F)F)cc1)CC2]

| | |
|---|---|
| 22 | 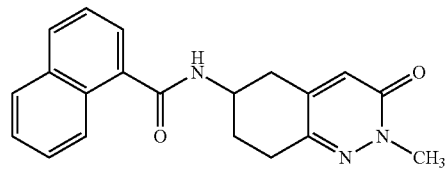 [SMILES: Cn1nc2c(cc1=O)CC(NC(=O)c1cccc3ccccc13)CC2] |
| 23 | 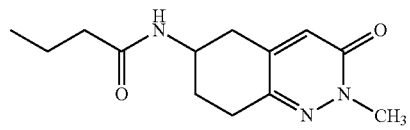 |
| 24 | 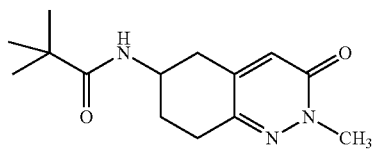 [SMILES: Cn1nc2c(cc1=O)CC(NC(=O)C(C)(C)C)CC2] |
| 25 | 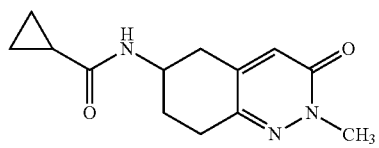 |
| 28 | 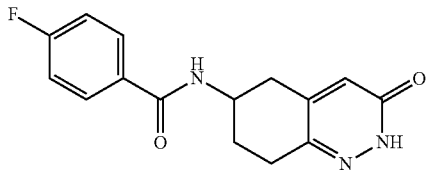 [SMILES: O=C(NC1CCc2n[nH]c(=O)cc2C1)c1ccc(F)cc1] |
| 29 | 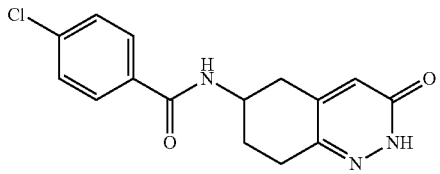 |
| 30 | 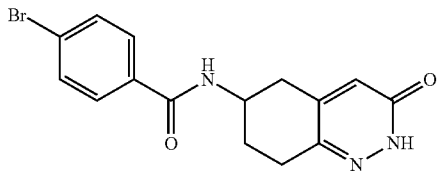 [SMILES: O=C(NC1CCc2n[nH]c(=O)cc2C1)c1ccc(Cl)cc1] |
| 31 | 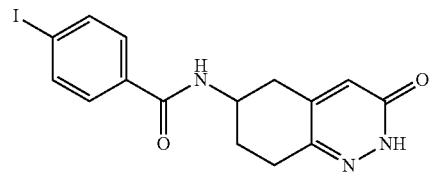 [SMILES: O=C(NC1CCc2n[nH]c(=O)cc2C1)c1ccc(I)cc1] |
| 32 | 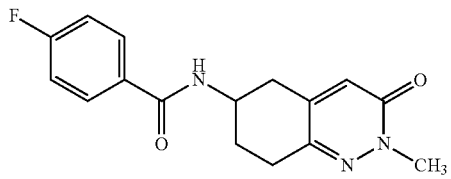 |

| | |
|---|---|
| 33 | 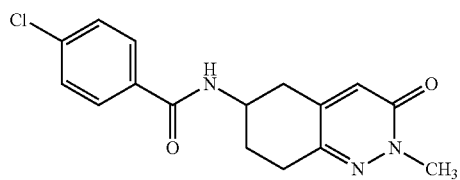 [SMILES: Cn1nc2c(cc1=O)CC(NC(=O)c1ccc(Cl)cc1)CC2] |
| 34 | 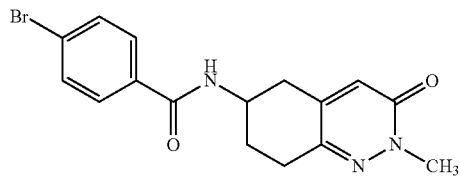 |
| 35 | 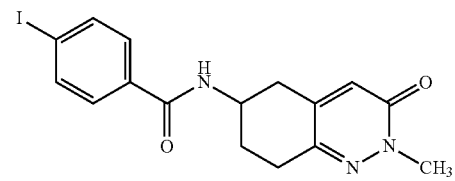 |
| 36 | 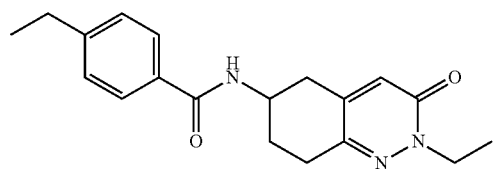 [SMILES: CCc1ccc(C(=O)NC2CCc3nn(CC)c(=O)cc3C2)cc1] |
| 37 | 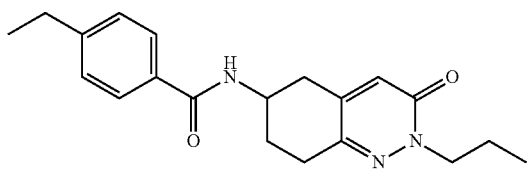 [SMILES: CCCn1nc2c(cc1=O)CC(NC(=O)c1ccc(CC)cc1)CC2] |
| 38 | 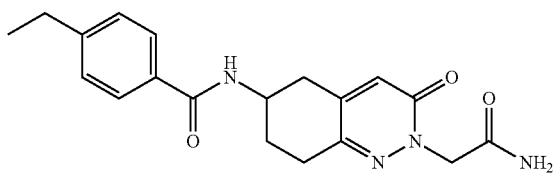 [SMILES: CCc1ccc(C(=O)NC2CCc3nn(CC(N)=O)c(=O)cc3C2)cc1] |
| 39 | 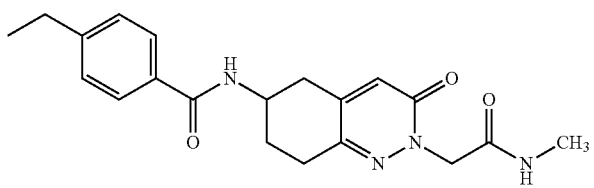 [SMILES: CCc1ccc(C(=O)NC2CCc3nn(CC(=O)NC)c(=O)cc3C2)cc1] |
| 40 | 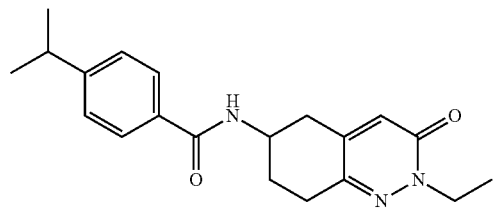 [SMILES: CCn1nc2c(cc1=O)CC(NC(=O)c1ccc(C(C)C)cc1)CC2] |

41 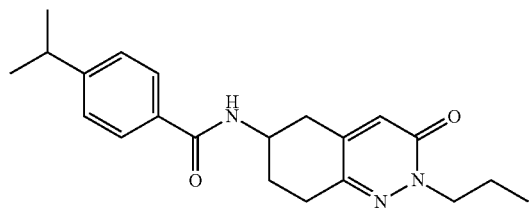 [SMILES: CCCn1nc2c(cc1=O)CC(NC(=O)c1ccc(C(C)C)cc1)CC2]
42 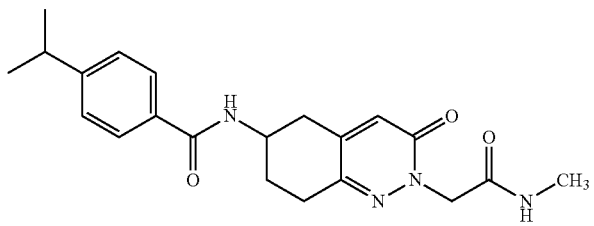 [SMILES: CNC(=O)Cn1nc2c(cc1=O)CC(NC(=O)c1ccc(C(C)C)cc1)CC2]
43 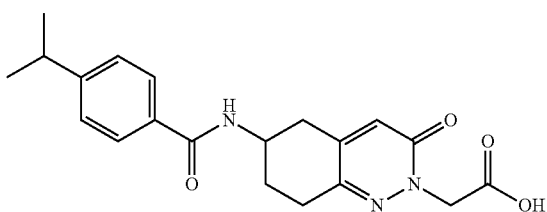 [SMILES: CC(C)c1ccc(C(=O)NC2CCc3nn(CC(=O)O)c(=O)cc3C2)cc1]
44 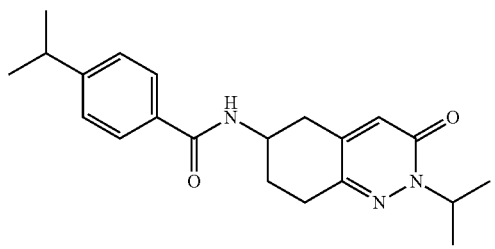 [SMILES: CC(C)c1ccc(C(=O)NC2CCc3nn(C(C)C)c(=O)cc3C2)cc1]
45 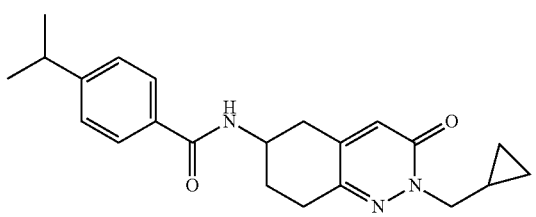 [SMILES: CC(C)c1ccc(C(=O)NC2CCc3nn(CC4CC4)c(=O)cc3C2)cc1]
46 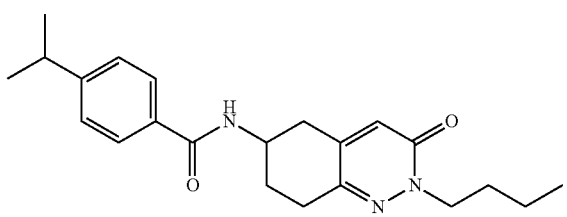
47 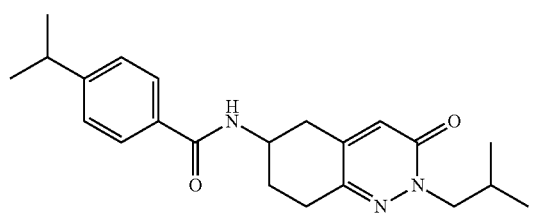 [SMILES: CC(C)Cn1nc2c(cc1=O)CC(NC(=O)c1ccc(C(C)C)cc1)CC2]

-continued
| 48 | 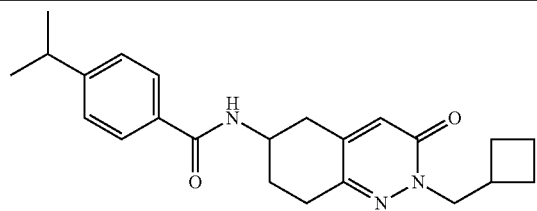 |
| --- | --- |
| 49 | 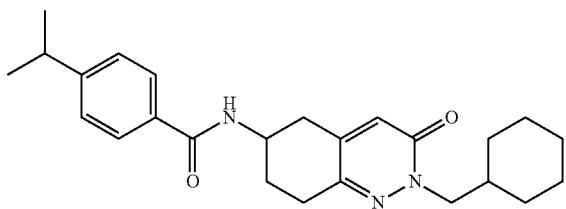 [SMILES: CC(C)c1ccc(C(=O)NC2CCc3nn(CC4CCCCC4)c(=O)cc3C2)cc1] |
| 50 | 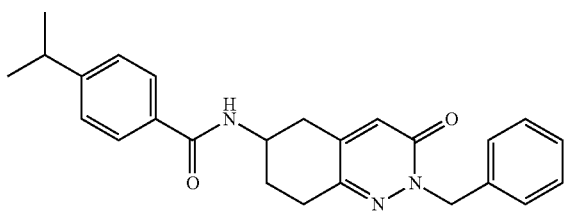 [SMILES: CC(C)c1ccc(C(=O)NC2CCc3nn(Cc4ccccc4)c(=O)cc3C2)cc1] |
| 51 | 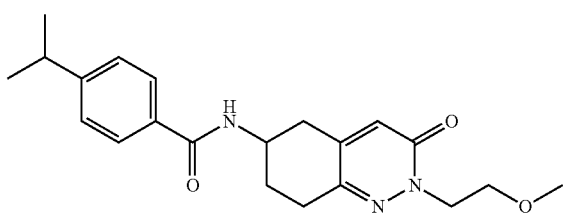 [SMILES: COCCn1nc2c(cc1=O)CC(NC(=O)c1ccc(C(C)C)cc1)CC2] |
| 52 | 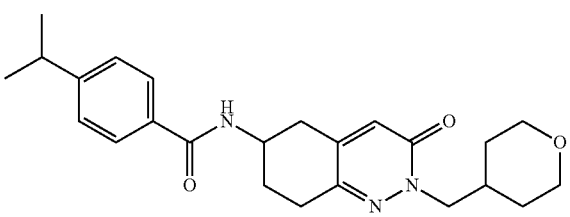 [SMILES: CC(C)c1ccc(C(=O)NC2CCc3nn(CC4CCOCC4)c(=O)cc3C2)cc1] |
| 53 | 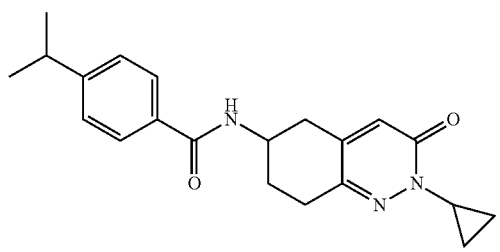 [SMILES: CC(C)c1ccc(C(=O)NC2CCc3nn(C4CC4)c(=O)cc3C2)cc1] |
| 54 | 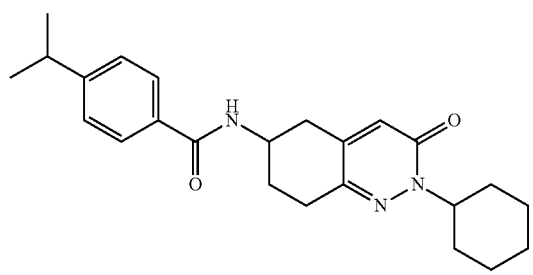 [SMILES: CC(C)c1ccc(C(=O)NC2CCc3nn(C4CCCCC4)c(=O)cc3C2)cc1] |

| 55 | 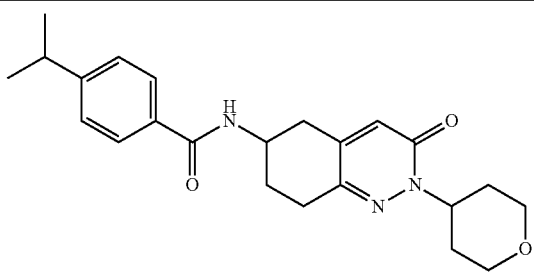 |
| 56 | 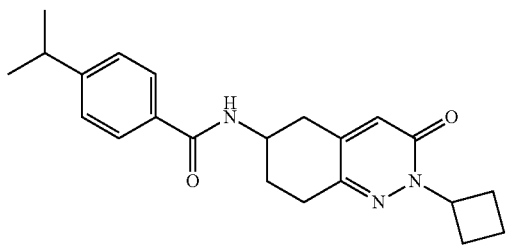 [SMILES: CC(C)c1ccc(C(=O)NC2CCc3nn(C4CCC4)c(=O)cc3C2)cc1] |
| 57 | 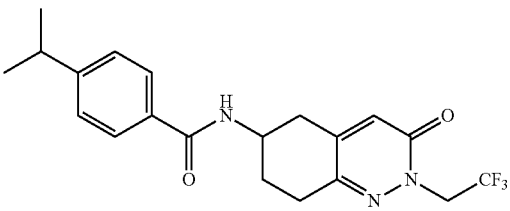 [SMILES: CC(C)c1ccc(C(=O)NC2CCc3nn(CC(F)(F)F)c(=O)cc3C2)cc1] |
| 58 | 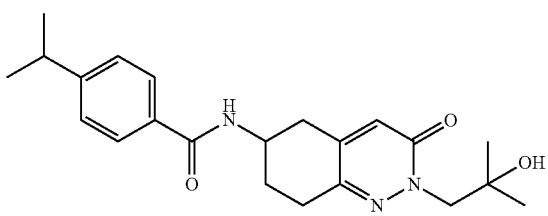 [SMILES: CC(C)c1ccc(C(=O)NC2CCc3nn(CC(C)(C)O)c(=O)cc3C2)cc1] |
| 59 | 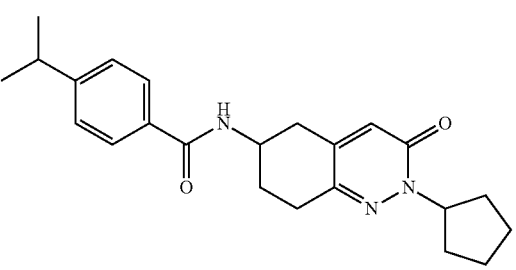 [SMILES: CC(C)c1ccc(C(=O)NC2CCc3nn(C4CCCC4)c(=O)cc3C2)cc1] |
| 60 | 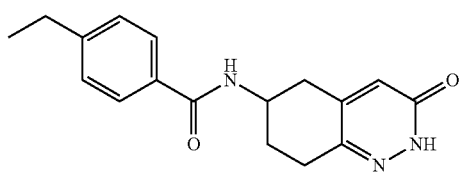 [SMILES: CCc1ccc(C(=O)NC2CCc3n[nH]c(=O)cc3C2)cc1] |
| 61 | 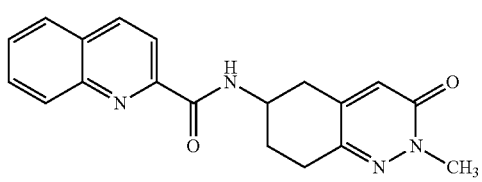 [SMILES: Cn1nc2c(cc1=O)CC(NC(=O)c1ccc3ccccc3n1)CC2] |

62

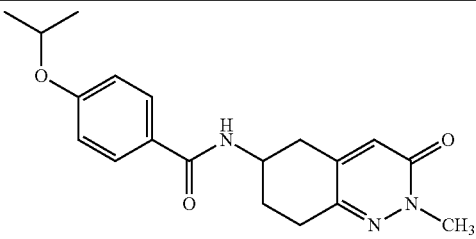

63

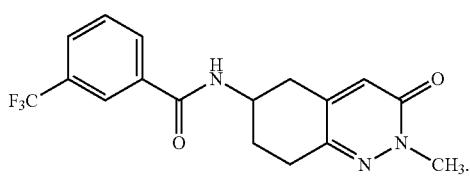 [SMILES: Cn1nc2c(cc1=O)CC(NC(=O)c1cccc(C(F)(F)F)c1)CC2]

17. A method of treating an autoimmune disease selected from the group consisting of celiac disease, type 1 diabetes (T1D), Stiff-person syndrome (SPS), Addison's disease (AD), Schmidt syndrome (SS), and Myasthenia gravis (MG), in a subject in need thereof, comprising the steps of:
(a) identifying a subject having anti-transglutaminase antibodies, antibodies against deamidated gliadin peptides, antibodies against acetylcholine receptor, and/or anti-endomysium antibodies; and
(b) administering to the subject a therapeutically effective amount of the pharmaceutical composition of claim 1.

* * * * *